US007482488B2

(12) United States Patent
Reddy et al.

(10) Patent No.: US 7,482,488 B2
(45) Date of Patent: Jan. 27, 2009

(54) ARYL AND HETEROARYL PROPENE AMIDES, DERIVATIVES THEREOF AND THERAPEUTIC USES THEREOF

(75) Inventors: M. V. Ramana Reddy, Upper Darby, PA (US); E. Premkumar Reddy, Villanova, PA (US)

(73) Assignee: Temple University - Of The Commonwealth System of Higher Education, Philadelphia, PA (US)

( * ) Notice: Subject to any disclaimer, the term of this patent is extended or adjusted under 35 U.S.C. 154(b) by 256 days.

(21) Appl. No.: 10/525,553

(22) PCT Filed: Aug. 28, 2003

(86) PCT No.: PCT/US03/26954

§ 371 (c)(1),
(2), (4) Date: Feb. 24, 2005

(87) PCT Pub. No.: WO2004/037751

PCT Pub. Date: May 6, 2004

(65) Prior Publication Data

US 2006/0167317 A1 Jul. 27, 2006

Related U.S. Application Data

(60) Provisional application No. 60/406,766, filed on Aug. 29, 2002.

(51) Int. Cl.
*C07C 233/05* (2006.01)
*A61K 31/65* (2006.01)
(52) U.S. Cl. .................. 564/167; 514/617; 514/622
(58) Field of Classification Search .......... 514/617, 514/622; 564/167
See application file for complete search history.

(56) References Cited

U.S. PATENT DOCUMENTS

| | | | |
|---|---|---|---|
| 3,891,685 A | 6/1975 | Hari et al. | 260/438.1 |
| 3,940,422 A | 2/1976 | Harita et al. | 260/340.5 |
| 3,975,435 A | 8/1976 | Nikawitz | 260/558 P |
| 3,988,358 A | 10/1976 | Heck | 260/465 D |
| 4,128,554 A | 12/1978 | Heck | 546/317 |
| 4,337,270 A | 6/1982 | Noda et al. | 424/310 |
| 4,835,312 A | 5/1989 | Itoh et al. | 564/205 |
| 5,461,075 A | 10/1995 | O'Neill et al. | 514/617 |
| 5,705,521 A * | 1/1998 | Abraham | 514/421 |
| 6,300,363 B1 | 10/2001 | Stevens et al. | 514/415 |
| 7,015,233 B2 | 3/2006 | Gomtsyan et al. | 514/322 |
| 2003/0158188 A1 | 8/2003 | Lee et al. | 514/228.2 |
| 2003/0158198 A1 | 8/2003 | Lee et al. | 514/241 |
| 2003/0195201 A1 | 10/2003 | Bo et al. | 517/227.5 |
| 2004/0087798 A1 | 5/2004 | Yamada | 546/336 |

FOREIGN PATENT DOCUMENTS

| | | |
|---|---|---|
| DE | 200110355 | 8/2001 |
| EP | 0147980 A2 | 7/1985 |
| EP | 1264820 | 12/2002 |
| JP | 63154663 A2 | 6/1988 |
| JP | 10096567 | 11/1998 |
| JP | 10330254 A2 | 12/1998 |
| JP | 09363359 | 6/1999 |
| JP | 10307760 | 4/2000 |
| JP | 2001-139550 * | 5/2001 |
| JP | 2001-139550 A | 5/2001 |
| JP | 2001139550 A2 | 5/2001 |
| WO | WO92/09285 | 6/1992 |
| WO | EP 0855387 A1 | 7/1998 |

OTHER PUBLICATIONS

Carter et al., Chemotherapy of Cancer, second edition, John Wiley & Sons, N.Y., N.Y., 1981, pp. 362-365.*
Alberghina et al., Reaction Kinetics of Cinnamoyl, β-2-Furylacryloyl, and β-2-Thienylacryloyl Chlorides with Anilines in Benzene, J. Org. Chem., vol. 43, No. 6, pp. 1121-1125, 1978.
Youcai, et al., Sythesis of 4-Pyridine-Acrylic Acid Derivatives, Acta Pharmaceutica Sinica, vol. XVI, No. 1, pp. 76-80, Jan. 1981.
Duran et al., Amides *para*hydroxycinnamiques: synthèse et propriétès inhibitrices vis-à-vis de l'alcool coniférylique déshydrogénase (CADH), Bulletin de la Société Chimique de France, 1987, No. 4, pp. 672-680.
Simonyan et al., Synthesis of Cinnamoyl Anilides and Study of Their Cholagogic Activity, Khim-Farm.Zh. (1991), 2S(12) 33-35.
Lamotte-Brasseur et al, PAF Receptor And "Cache-Oreilles" Effect. Simple PAF Antagonists, Lipids, vol. 26, No. 12, 1991.
Huang et al., Stereoselective Synthesis of (2Z)-Cinnamanilides via Desulfonylation of (2E)-α-Amido- α, β-Unsaturated Sulfones by Sodium Hydrogen Telluride, Heteroatom Chemistry, vol. 3, No. 5/6, 1992.
Blaakmeer et al., Isolation, Identification, And Synthesis Of Miriamides, New Hostmarkers From Eggs Of *Pieris Brassicae*, Journal of Natural Products, vol. 57, No. 1, pp. 90-99, Jan. 1994.
Blaakmeer et al., Structure-Activity Relationship of Isolated Avenanthramide Alkaloids And Synthesized Related Compounds As Oviposition Deterrents For *Pieris Brassicae*, Journal of Natural Products, vol. 57, No. 8, pp. 1145-1151, Aug. 1994.
Kim et al., Nucleophilic substitution reactions of cinnamoyl chlorides with anilines in acetonitrile and acetonitrile-methanol mixtures, J. Chem. Soc. Perkin Trans. 2, 1995, pp. 2257-2261.
Wang et al., Lewis Acid Catalyzed Reaction of Cinnamanilides: Competition of Intramolecular and Imtermolecular Friedel-Crafts Reaction, Synthesis, Jan. 1997, pp. 87-90.
Ali et al., Palladium(II)-catalyzed regioselective carbonylative coupling of aniline derivatives with terminal aryl acetylenes to give acrylamides under syngas conditions, Tet. Lett., 41 (2000), pp. 5761-5764.

(Continued)

*Primary Examiner*—Shailendra Kumar
(74) *Attorney, Agent, or Firm*—Daniel A. Monaco; Drinker Biddle & Reath LLP

(57) ABSTRACT

Compounds useful as antiproliferative agents, radioprotective agents and cytoprotective agents, including, for example, anticancer agents, are provided according to formula I: wherein ring A, ring B, ∼∼∼,X, $R^1$, $R^2$, $R^3$, a, and b are as defined herein.

6 Claims, No Drawings

OTHER PUBLICATIONS

Liu et al., Stereoselective Synthesis Of (2E)-Cinnamanilides *via* Desulfonylation Of (2E)-α-Amido- α, β-Unsaturated Sulfones By Samarium/Glacial Acetic Acid/Ethanol System, OPPI Briefs, vol. 33, No. 4, pp. 372-375, 2001.

Avanesyan et al., Phosphorus Oxychloride In Organic Synthesis. Part 2. Synthesis Of Cinnamic Acid Arylamides, Pharmaceutical Chemistry Journal, vol. 35, No. 2, 2001.

Patent Abstracts of Japan, Publication No. 10306024A, abstracting Hiroshi et al., Application No. 10096567, 1998.

Patent Abstracts of Japan, Publication No. 2001139550A, abstracting Teruo et al., Application No. 11326416, 2001.

Patent Abstracts of Japan, Publication No. 63154663A, abstracting Yoshihide et al., Application No. 61300878, 1998.

Patent Abstracts of Japan, Publication No. 11158068A, abstracting Hiroshi et al., Application No. 09363359, 1999.

Patent Abstracts of Japan, Publication No. 2000095690A, abstracting Hiroshi et al., Application No. 10307760, 2000.

Patent Abstracts of Japan, Publication No. 01139550A, abstracting Ito Satoru, Application No. 62297327, 1989.

Patent Abstracts of Japan, Publication No. 10330254A, abstracting Hiroshi et al., Application No. 10126586, 1998.

Chemical Abstracts Registry No. 371199-69-8, 1H-Indole-2-carboxylic acid, 6-fluoro-3-[(1-oxo-3-phenyl-2-propenyl)amino]-, ethyl ester (9CI), Registry Copyright 2005 ACS on STN, Entered STN: Nov. 21, 2001.

Chemical Abstracts Registry No. 330439-40-2, 1H-Indole-2-carboxylic acid, 5-bromo-3-[(1-oxo-3-phenyl-2-propenyl)amino]-, ethyl ester (9CI), Registry Copyright 2005 ACS on STN, Entered STN: Apr. 6, 2001.

Chemical Abstracts Registry No. 330439-38-8, 1H-Indole-2-carboxylic acid, 3-[(1-oxo-3-phenyl-2-propenyl)amino]-,ethyl ester (9CI), Registry Copyright 2005 ACS on STN, Entered STN: Apr. 6, 2001.

Chemical Abstracts Registry No. 304876-44-6, 1H-Indole-2-carboxylic acid, 5-methyl-3-[(1-oxo-3-phenyl-2-propenyl)amino]-,ethyl ester (9CI), Registry Copyright 2005 ACS on STN, Entered STN: Nov. 29, 2000.

Chemical Abstracts Registry No. 299409-11-3, 1H-Indole-2-carboxylic acid, 5-fluoro-3-[(1-oxo-3-phenyl-2-propenyl)amino]-, ethyl ester (9CI), Registry Copyright 2005 ACS on STN, Entered STN: Oct. 26, 2000.

Chemical Abstracts Registry No. 220268-76-8, 2-Propenamide, N-(2-benzoyl-6-chloro-1H-indol-3-yl)-3-[3-(trifluoromethyl)phenyl]-, (2E)- (9CI), Registry Copyright 2005 ACS on STN, Entered STN: Mar. 9, 1999.

Chemical Abstracts Registry No. 220267-12-9, 2-Propenamide, N-(2-benzoyl-6-chloro-1H-indol-3-yl)-3-phenyl- (9CI), Registry Copyright 2005 ACS on STN, Entered STN: Mar. 9, 1999.

Chemical Abstracts Registry No. 364370-57-0, 2-Propenamide, 3-(3-nitrophenyl)-N-(3-nitro-4-pyridinyl)- (9CI), Registry Copyright 2005 ACS on STN, Entered STN: Oct. 24, 2001.

Chemical Abstracts Registry No. 353537-92-5, 2-Propenamide, 3-(2,6-dichlorophenyl)-N-4-pyridinyl-, (2E)- (9CI), Registry Copyright 2005 ACS on STN, Entered STN: Aug. 29, 2001.

Chemical Abstracts Registry No. 352677-68-0, 2-Propenamide, 3-(2,6-dichlorophenyl)-N-4-pyridinyl- (9CI), Registry Copyright 2005 ACS on STN, Entered STN: Aug. 27, 2001.

Chemical Abstracts Registry No. 349426-18-2, 2-Propenamide, 3-(2-chlorophenyl)-N-4-pryidinyl- (9CI), Registry Copyright 2005 ACS on STN, Entered STN: Jul. 29, 2001.

Chemical Abstracts Registry No. 328269-34-7, 2-Propenamide, 3-(4-methoxyphenyl)-N-4-pyridinyl- (9CI), Registry Copyright 2005 ACS on STN, Entered STN: Mar. 21, 2001.

Chemical Abstracts Registry No. 321966-25-0, 2-Propenamide, 3-(3-nitrophenyl)-N-4-pyridinyl- (9CI), Registry Copyright 2005 ACS on STN, Entered STN: Feb. 19, 2001.

Chemical Abstracts Registry No. 321966-11-4, 2-Propenamide, 3-(3-iodophenyl)-N-4-pyridinyl- (9CI), Registry Copyright 2005 ACS on STN, Entered STN: Feb. 19, 2001.

Chemical Abstracts Registry No. 191327-40-9, 2-Propenamide, 3-phenyl-N-(2,3,5,6-tetrachloro-4-pyridinyl)-, (E)- (9CI), Registry Copyright 2005 ACS on STN, Entered STN: Jul. 18, 1997.

Chemical Abstracts Registry No. 155042-59-4, 2-Propenamide, 3-(3,4-dihydroxyphenyl)-N-4-pyridinyl-, (E)- (9CI) Registry Copyright 2005 ACS on STN, Entered STN: May 13, 1994.

Chemical Abstracts Registry No. 117906-33-9, 2-Propenamide, 3-[3,5-bis(1,1-dimethylethyl)-4-hydroxyphenyl]-N-4-pyridinyl- (9CI), Registry Copyright 2005 ACS on SYN, Entered STN: Dec. 9,1988.

Chemical Abstracts Registry No. 115499-66-6, 2-Propenamide, 3,3,-bis(4-methoxyphenyl)-N-4-pryidinyl- (9CI), Registry Copyright 2005 ACS on STN, Entered STN: Jul. 30, 1988.

Chemical Abstracts Registry No. 113985-22-1, 2-Propenamide, 3-(4-hydroxy-3-metoxyphenyl)-N-4-pyridinyl-, (E)- (9CI), Registry Copyright 2005 ACS on STN, Entered STN: Apr. 23, 1988.

Chemical Abstracts Registry No. 94822-47-6, Cinnamamide, 3,4,5-trimethoxy-N-4-pyridyl- (7CI), Registry Copyright 2005 ACS on STN, Entered STN: Feb. 17, 1985.

Chemical Abstracts Registry No. 85649-70-3, 2-Propenamide, 3-phenyl-N-4-pyridinyl- (9CI), Registry Copyright 2005 ACS on STN, Entered STN: Nov. 16, 1984.

Chemical Abstracts Registry No. 367957-14-0, 2-Propenamide, N-(3-chloro-4-methoxyphenyl)-3-(4-methoxyphenyl)- (9CI), Registry Copyright 2005 ACS on STN, Entered STN: Nov. 8, 2001.

Chemical Abstracts Registry No. 357177-82-3, 2-Propenamide, N-(3,4-dimethoxyphenyl)-3-(4-methoxyphenyl)- (9CI), Registry Copyright 2005 ACS on STN, Entered STN: Sep. 17, 2001.

Chemical Abstracts Registry No. 343783-76-6, Benzoic acid, 2-[[(2E)-3-(3,4-dimethoxyphenyl)-1-oxo-2-propenyl]amino]-4,5-dimethoxy-, ethyl ester (9CI), Registry Copyright 2005 ACS on STN, Entered STN: Jun. 28, 2001.

Chemical Abstracts Registry No. 340258-61-9, 2-Propenamide, N,3-bis(4-methoxyphenyl)-, (2E)- (9CI), Registry Copyright 2005 ACS on STN, Entered STN: Jun. 11, 2001.

Chemical Abstracts Registry No. 340258-44-8, 2-Propenamide, 3-(3,4-dimethoxyphenyl)-N-(4-methoxyphenyl)-, (2E)- (9CI), Registry Copyright 2005 ACS on STN, Entered STN: Jun. 11, 2001.

Chemical Abstracts Registry No. 339165-72-9, 2-Propenamide, 3-(3,4-dimethoxyphenyl)-N-(4-methoxyphenyl)- (9CI), Registry Copyright 2005 ACS on STN, Entered STN: Jun. 1, 2001.

Chemical Abstracts Registry No. 329778-90-7, 2-Propenamide, N-(2,4-dimethoxyphenyl)-3-(2,3,4-trimethoxyphenyl)- (9CI), Registry Copyright 2005 ACS on STN, Entered STN: Apr. 3, 2001.

Chemical Abstracts Registry No. 328269-11-0, 2-Propenamide, N,3-bis(4-methoxyphenyl)- (9CI), Registry Copyright 2005 ACS on STN, Entered STN: Mar. 21, 2001.

Chemical Abstracts Registry No. 312287-65-3, 2-Propenamide, N,3-bis(3,4-dimethoxyphenyl)- (9CI), Registry Copyright 2005 ACS on STN, Entered STN: Dec. 29, 2000.

Chemical Abstracts Registry No. 301229-71-0, 2-Propenamide, N-(2,4-dimethoxyphenyl)-3-(3,4-dimethoxyphenyl)- (9CI), Registry Copyright 2005 ACS on STN, Entered STN: Nov. 3, 2000.

Chemical Abstracts Registry No. 300672-85-9, 2-Propenamide, 3-(3,4-dimethoxyphenyl)-N-(4-methoxy-2-nitrophenyl)- (9CI), Registry Copyright 2005 ACS on STN, Entered STN: Nov. 1, 2000.

Chemical Abstracts Registry No. 188544-62-9, Benzamide, 2-[[(2E)-3-(3,4-dimethoxyphenyl)-1-oxo-2-propenyl]amino]-5-methoxy- (9CI), Registry Copyright 2005 ACS on STN, Entered STN: Apr. 22, 1997.

Chemical Abstracts Registry No. 188544-61-8, Benzamide, 2[[(2E)-3-(3,4-dimethoxyphenyl)-1-oxo-2-propenyl]amino]-4,5-dimethoxy- (9CI), Registry Copyright 2005 ACS on STN, Entered STN: Apr. 22, 1997.

Chemical Abstracts Registry No. 188544-52-7, Benzamide, 4,5-dimethoxy-2-[[(2E)-1-oxo-3-(3,4,5-trimethoxyphenyl)-2-propenyl]amino]- (9CI), Registry Copyright 2005 ACS on STN, Entered STN: Apr. 22, 1997.

Chemical Abstracts Registry No. 292051-77-5, 2-Propenamide, N-(2,4-dimethoxyphenyl)-3-(4-methoxyphenyl)- (9CI), Registry Copyright 2005 ACS on STN, Entered STN: Oct. 2, 2000.

Chemical Abstracts Registry No. 217185-45-0, Benzamide, 2-[[(2E)-3-(3,4-dimethoxyphenyl)-1-oxo-propenyl]amino]-N-(2- hydroxyethyl)-5-methoxy- (9CI), Registry Copyright 2005 ACS on STN, Entered STN: Jan. 15, 1999.
Chemical Abstracts Registry No. 188544-51-6, Benzamide, 2-[[(2E)-3-(3,4-dimethoxyphenyl)-1-oxo-2-propenyl]amino]-(2-hydroxyethyl)-4,5-dimethoxy- (9CI), Registry Copyright 2005 ACS on STN, Entered STN: Apr. 22, 1997.
Chemical Abstracts Registry No. 153566-05-3, Benzoic acid, 2-[[3-(3,4-dimethoxyphenyl)-1-oxo-2-propenyl]amino]3,5-dimethoxy-, (E)- (9CI), Registry Copyright 2005 ACS on STN, Entered STN: Mar. 10, 1994.
Chemical Abstracts Registry No. 153566-03-1, Benzoic acid, 2-[[3-(3,4-dimethoxyphenyl)-1-oxo-2-propenyl]amino]-3,5-dimethoxy-, methyl ester, (E)- (9CI), Registry Copyright 2005 ACS on STN, Entered STN: Mar. 10, 1994.
Chemical Abstracts Registry No. 153566-02-0, Benzoic acid, 3,5-dimethoxy-2-[[1-oxo-3-3(3,4,5-trimethoxyphenyl)-2-propenyl]amino]-, methyl ester, (E)- (9CI), Registry Copyright 2005 ACS on STN, Entered STN: Mar. 10, 1994.
Chemical Abstracts Registry No. 72909-54-7, Benzoic acid, 2-[[3-(3,4-dimethoxyphenyl)-1-oxo-2-propenyl]amino]4,5-dimethoxy-, methyl ester (9CI), Registry Copyright 2005 ACS on STN, Entered STN: Nov. 16, 1984.
Chemical Abstracts Registry No. 72909-48-9, Benzoic acid, 2-[[3-(3,4-dimethoxyphenyl)-1-oxo-2-propenyl]amino]-4,5-dimethoxy- (9CI), Registry Copyright 2005 ACS on STN, Entered STN: Nov. 16, 1984.
Chemical Abstracts Registry No. 4658-59-7, 2-Propenamide, N,3-bis(3,4,5-trimethoxyphenyl)- (9CI), Registry Copyright 2005 ACS on STN, Entered STN: Nov. 16, 1984.
Chemical Abstracts Registry No. 327973-42-2, 2-Propenamide, 3-(3,4-dimethoxyphenyl)-N-4-pyridinyl- (9CI), Registry Copyright 2005 ACS on STN, Entered STN: Mar. 19, 2001.
Chemical Abstracts Registry No. 153566-04-2, Benzoic acid, 3,5-dimethoxy-2-[[1-oxo-3-(3,4,5-trimethoxyphenyl)-2-propenyl]amino]-, (E)- (9CI), Registry Copyright 2005 ACS on STN, Entered STN: Mar. 10, 1994.

Derwent Record Abstract, Novel m-diaminophenyl acrylamide derivatives or their physiologically compatible, water soluble salts are useful for the production of hair coloring formulations, DE20111037, Oct. 4, 2001.
Derwent Record Abstract, Use or new of known N-acyl-anthranilic acid derives—for control of insects, esp cabbage white butterfiles, by determining oviposition, NL9202078, Jun. 16, 1994.
Chemical Abstracts Registry No. 472981-92-3, 3-(4-chlrophenyl)-N-(3-methoxyphenyl)-2-propenamide, SB-366791, Entered STN Nov. 11, 2002.
"New Products for Cell Signaling and Neuroscience", *Celltransmissions*, 2002, 18(2), 14.
J. G. Breitenbucher, et al., "The TRPV1 Vanilloid Receptor: A Target for Therapeutic Intervention", in A. M. Doherty (Ed.), *Annual Reports in Medicinal Chemistry*, vol. 40, Elsevier (2005), p. 185-98.
J. B. Davis, et al., "Identification of a potent and selective antagonist of vaniloid receptor-1, SB-366791." *Soc. Neurosci. Abstr.* 910.5 (2001).
J. B. Davis, et al., "The Vanilloid Receptor and Vanilloid Receptor-Like Genes: A Hot Topic Getting Hotter", Celltransmissions, 2002, 18(2), 3-9.
C.J. Fowler, et al., "Inhibition of C6 glicoma cell proliferation by anandamide, 1-arachidonoylglycerol, and by a water soluble phosphate ester of anandamide: variability in response and involvement of arachidonic acid", Biochem. Pharmacol., 2003, 66, 757-67.
H.K. Rami, et al., "Identification of SB-366791, a potent and selective antagonist of vanilloid receptor-1," *Drugs of the Future*, 2002, 27 (Supp. A), 411.
*Chem. Abs.* 135:288586, abstracting DE 20110355, 2001.
*Chem. Abs.* 59:28307, abstracting Terada et al., Nippon Kagaku Zasshi, 1962, 63, 490-92.
Beilstein Crossfire Database Registry No. 2755456, 1963.
Beilstein Crossfire Database Registry No. 7434217, 1995.
Schultz et al., *J. Pharm. Sci.*, 1963, 52, 503.
Kim et al., *J. Chem. Soc., Perkin Trans. 2*, 1995, 2257-62.

* cited by examiner

ARYL AND HETEROARYL PROPENE AMIDES, DERIVATIVES THEREOF AND THERAPEUTIC USES THEREOF

This application is a 371 of PCT/US03126954, filed 08/28/2003.

FIELD OF THE INVENTION

The invention relates to compositions and methods for the treatment of proliferative disorders, including but not limited to cancer. The invention further relates to compositions that afford protection from the cytotoxic effects of ionizing radiation and of cytotoxic chemotherapeutic agents.

BACKGROUND OF THE INVENTION

Aryl and Heteroaryl Propene Amides

Cancer remains a leading cause of mortality in the United States and in the world. To be useful, a new chemotherapeutic agent should have a wide spectrum of activity and significant therapeutic index.

Aryl and heteroaryl propene amides have been prepared by reacting substituted aromatic acryloyl halides (such as cinnamoyl chlorides) with amino-substituted aromatic compounds (Kim et al., *J. Chem. Soc. Perkin Trans. 2*, 1995, p2257 describes reaction of cinnamoyl chlorides with anilines Alberghina et al., *J. Org. Chem.*, Vol. 43, No. 6, 1978, p1122 describes reaction of furylacryloyl and thienylacryloyl chlorides with anilines.). Another route to aryl and heteroaryl propene amides involves reaction of an aromatic vinylhalide (preferably a bromide or iodide) with an aromatic amine using palladium catalysis (U.S. Pat. No. 3,988,358).

Certain propene amides have shown activity in treatment of atherosclerosis (Japanese patent 2001139550). Certain propene amides have also shown biological activity as inhibitors of oviposition in several herbivorous insect species (Blaakmeer et al, *Journal of Natural Products*, Vol. 57, No. 1, pg. 90, 1994, and Vol. 57, No. 8, pg. 1145). Some substituted cinnamanilides have demonstrated bacteriostatic properties (U.S. Pat. No. 3,975,435). Certain ortho-acyl -substituted cinnamanilides have been shown to inhibit the proliferation of vascular intimal cells which occurs incident to vascular stenosis (EP 0 855 387 A1). Other ortho acyl cinnamanilides have demonstrated biological activity as antiallergy agents (U.S. Pat. No. 4,337,270). N-imidazolyl cinnamides bearing an ortho-acyl substituent have been investigated as neovascularization inhibitors (Japanese patent applications 09363359 and 10307760). Other related compounds, N-indolylcinnamides having an ortho acyl substituent, have been shown to possess activity as COX-2 inhibitors (U.S. Pat. No. 6,300,363 B1). At least one cinnamanilide has been shown to be an antagonist at the platelet-activating factor (PAF) receptor (Lamotte-Brasseur et al., *Lipids,* Vol. 26, No. 12, 1991, p1167). Also N-pyridyl cinnamides have demonstrated antagonist activity of the enzyme CADH (Duran et al., *Bull. Soc. Chim. Fr.,* 1987, No. 4, 1987, p 672).

Cell antiproliferative agents, and anticancer therapeutics in particular, are needed which are useful in inhibiting proliferation of and/or killing cancer cells. In particular, such agents are needed which are selective in the killing of proliferating cells such as tumor cells, but not normal cells. Antineoplastic agents are needed which are effective against a broad range of tumor types.

Ionizing Radiation Health Risks

Ionizing radiation has an adverse effect on cells and tissues, primarily through cytotoxic effects. In humans, exposure to ionizing radiation occurs primarily through therapeutic techniques (such as anticancer radiotherapy) or through occupational and environmental exposure.

A major source of exposure to ionizing radiation is the administration of therapeutic radiation in the treatment of cancer or other proliferative disorders. Depending on the course of treatment prescribed by the treating physician, multiple doses may be received by a subject over the course of several weeks to several months.

Therapeutic radiation is generally applied to a defined area of the subject's body which contains abnormal proliferative tissue, in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment.

There are also some treatments that require exposure of the subject's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Numerous methods have been designed to reduce normal tissue damage while still delivering effective therapeutic doses of ionizing radiation. These techniques include brachytherapy, fractionated and hyperfractionated dosing, complicated dose scheduling and delivery systems, and high voltage therapy with a linear accelerator. However, such techniques only attempt to strike a balance between the therapeutic and undesirable effects of the radiation, and full efficacy has not been achieved.

For example, one treatment for subjects with metastatic tumors involves harvesting their hematopoietic stem cells and then treating the subject with high doses of ionizing radiation. This treatment is designed to destroy the subject's tumor cells, but has the side effect of also destroying their normal hematopoietic cells. Thus, a portion of the subject's bone marrow (containing the hematopoietic stem cells), is removed prior to radiation therapy. Once the subject has been treated, the autologous hematopoietic stem cells are returned to their body.

However, if tumor cells have metastasized away from the tumor's primary site, there is a high probability that some tumor cells will contaminate the harvested hematopoietic cell population. The harvested hematopoietic cell population may also contain neoplastic cells if the subject suffers from cancers of the bone marrow such as the various French-American-British (FAB) subtypes of acute myelogenous leukemias (AML), chronic myeloid leukemia (CML), or acute lymphocytic leukemia (ALL). Thus, the metastasized tumor cells or resident neoplastic cells must be removed or killed prior to reintroducing the stem cells to the subject. If any living tumorigenic or neoplastic cells are reintroduced into the subject, they can lead to a relapse.

Prior art methods of removing tumorigenic or neoplastic cells from harvested bone marrow are based on a whole-population tumor cell separation or killing strategy, which typically does not kill or remove all of the contaminating malignant cells. Such methods include leukopheresis of mobilized peripheral blood cells, immunoaffinity-based selection or killing of tumor cells, or the use of cytotoxic or photosensitizing agents to selectively kill tumor cells. In the best case, the malignant cell burden may still be at 1 to 10 tumor cells for every 100,000 cells present in the initial harvest (Lazarus et al. *J. of Hematotherapy,* 2(4):457-66, 1993).

Thus, there is needed a purging method designed to selectively destroy the malignant cells present in the bone marrow, while preserving the normal hematopoietic stem cells needed for hematopoietic reconstitution in the transplantation subject.

Exposure to ionizing radiation can also occur in the occupational setting. Occupational doses of ionizing radiation may be received by persons whose job involves exposure (or potential exposure) to radiation, for example in the nuclear power and nuclear weapons industries. Military personnel stationed on vessels powered by nuclear reactors, or soldiers required to operate in areas contaminated by radioactive fallout, risk similar exposure to ionizing radiation. Occupational exposure may also occur in rescue and emergency personnel called in to deal with catastrophic events involving a nuclear reactor or radioactive material. Other sources of occupational exposure may be from machine parts, plastics, and solvents left over from the manufacture of radioactive medical products, smoke alarms, emergency signs, and other consumer goods. Occupational exposure may also occur in persons who serve on nuclear powered vessels, particularly those who tend the nuclear reactors, in military personnel operating in areas contaminated by nuclear weapons fallout, and in emergency personnel who deal with nuclear accidents. Environmental exposure to ionizing radiation may also result from nuclear weapons detonations (either experimental or during wartime), discharges of actinides from nuclear waste storage and processing and reprocessing of nuclear fuel, and from naturally occurring radioactive materials such as radon gas or uranium. There is also increasing concern that the use of ordnance containing depleted uranium results in low-level radioactive contamination of combat areas.

Radiation exposure from any source can be classified as acute (a single large exposure) or chronic (a series of small low-level, or continuous low-level exposures spread over time). Radiation sickness generally results from an acute exposure of a sufficient dose, and presents with a characteristic set of symptoms that appear in an orderly fashion, including hair loss, weakness, vomiting, diarrhea, skin burns and bleeding from the gastrointestinal tract and mucous membranes. Genetic defects, sterility and cancers particularly bone marrow cancer) often develop over time. Chronic exposure is usually associated with delayed medical problems such as cancer and premature aging. An acute a total body exposure of 125,000 millirem may cause radiation sickness. Localized doses such as are used in radiotherapy may not cause radiation sickness, but may result in the damage or death of exposed normal cells.

For example, an acute total body radiation dose of 100,000-125,000 millirem (equivalent to 1 Gy) received in less than one week would result in observable physiologic effects such as skin burns or rashes, mucosal and GI bleeding, nausea, diarrhea and/or excessive fatigue. Longer term cytotoxic and genetic effects such as hematopoietic and immunocompetent cell destruction, hair loss (alopecia), gastrointestinal, and oral mucosal sloughing, venoocclusive disease of the liver and chronic vascular hyperplasia of cerebral vessels, cataracts, pneumonites, skin changes, and an increased incidence of cancer may also manifest over time. Acute doses of less than 10,000 millirem (equivalent to 0.1 Gy) typically will not result in immediately observable biologic or physiologic effects, although long term cytotoxic or genetic effects may occur.

A sufficiently large acute dose of ionizing radiation, for example 500,000 to over 1 million millirem (equivalent to 5-10 Gy), may kill a subject immediately. Doses in the hundreds of thousands of millirems may kill within 7 to 21 days from a condition called "acute radiation poisoning." Reportedly, some of the Chernobyl firefighters died of acute radiation poisoning, having received acute doses in the range of 200,000-600,000 millirem (equivalent to 2-6 Gy). Acute doses below approximately 200,000 millirem do not result in death, but the exposed subject will likely suffer long-term cytotoxic or genetic effects as discussed above.

Acute occupational exposures usually occur in nuclear power plant workers exposed to accidental releases of radiation, or in fire and rescue personnel who respond to catastrophic events involving nuclear reactors or other sources of radioactive material. Suggested limits for acute occupational exposures in emergency situations were developed by the Brookhaven National Laboratories, and are given in Table 1.

TABLE 1

| Whole Body Conditions for Dose Limit | Activity Required | Conditions for Exposure |
|---|---|---|
| 10,000 millirem* | Protect property | Voluntary, when lower dose not practical |
| 25,000 millirem | Lifesaving Operation; Protect General Public | Voluntary, when lower dose not practical |
| >25,000 millirem | Lifesaving operation; Protect large population | Voluntary, when lower dose not practical, and the risk has been clearly explained |

*100,000 millirem equals one sievert (Sv). For penetrating radiation such as gamma radiation, one Sv equals approximately one Gray (Gy). Thus, the dosage in Gy can be estimated as 1 Gy for every 100,000 millirem.

A chronic dose is a low level (i.e., 100-5000 millirem) incremental or continuous radiation dose received over time. Examples of chronic doses include a whole body dose of ~5000 millirem per year, which is the dose typically received by an adult working at a nuclear power plant. By contrast, the Atomic Energy Commission recommends that members of the general public should not receive more than 100 millirem per year. Chronic doses may cause long-term cytotoxic and genetic effects, for example manifesting as an increased risk of a radiation-induced cancer developing later in life. Recommended limits for chronic exposure to ionizing radiation are given in Table 2.

TABLE 2

| Organ or Subject | Annual Occupational Dose in millirem |
|---|---|
| Whole Body | 5000 |
| Lens of the Eye | 15,000 |
| Hands and wrists | 50,000 |
| Any individual organ | 50,000 |
| Pregnant worker | 500/9 months |
| Minor (16-18) receiving training | 100 |

By way of comparison, Table 3 sets forth the radiation doses from common sources.

TABLE 3

| Sources | Dose In Millirem |
|---|---|
| Television | <1/yr |
| Gamma Rays, Jet Cross Country | 1 |

TABLE 3-continued

| Sources | Dose In Millirem |
|---|---|
| Mountain Vacation - 2 week | 3 |
| Atomic Test Fallout | 5 |
| U.S. Water, Food & Air (Average) | 30/yr |
| Wood | 50/yr |
| Concrete | 50/yr |
| Brick | 75/yr |
| Chest X-Ray | 100 |
| Cosmic Radiation (Sea Level) | 40/yr (add 1 millirem/100 ft elev.) |
| Natural Background San Francisco | 120/yr |
| Natural Background Denver | 50/yr |
| Atomic Energy Commission Limit For Workers | 5000/yr |
| Complete Dental X-Ray | 5000 |
| Natural Background at Pocos de Caldras, Brazil | 7000/yr |
| Whole Body Diagnostic X-Ray | 100,000 |
| Cancer Therapy | 500,000 (localized) |
| Radiation Sickness-Nagasaki | 125,000 (single doses) |
| $LD_{50}$ Nagasaki & Hiroshima | 400,000-500,000 (single dose) |

Chronic doses of greater than 5000 millirem per year (0.05 Gy per year) may result in long-term cytotoxic or genetic effects similar to those described for persons receiving acute doses. Some adverse cytotoxic or genetic effects may also occur at chronic doses of significantly less than 5000 millirem per year. For radiation protection purposes, it is assumed that any dose above zero can increase the risk of radiation-induced cancer (i.e., that there is no threshold). Epidemiologic studies have found that the estimated lifetime risk of dying from cancer is greater by about 0.04% per rem of radiation dose to the whole body.

While anti-radiation suits or other protective gear may be effective at reducing radiation exposure, such gear is expensive, unwieldy, and generally not available to public. Moreover, radioprotective gear will not protect normal tissue adjacent a tumor from stray radiation exposure during radiotherapy. What is needed, therefore, is a practical way to protect subjects who are scheduled to incur, or are at risk for incurring, exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Pharmaceutical radioprotectants offer a cost-efficient, effective and easily available alternative to radioprotective gear. However, previous attempts at radioprotection of normal cells with pharmaceutical compositions have not been entirely successful. For example, cytokines directed at mobilizing the peripheral blood progenitor cells confer a myeloprotective effect when given prior to radiation (Neta et al., Semin. Radiat. Oncol. 6:306-320, 1996), but do not confer systemic protection. Other chemical radioprotectors administered alone or in combination with biologic response modifiers have shown minor protective effects in mice, but application of these compounds to large mammals was less successful, and it was questioned whether chemical radioprotection was of any value (Naisin, J. R., Bacq and Alexander Award Lecture. "Chemical radioprotection: past, present, and future prospects", Int J Radiat Biol. 73:443-50, 1998). Pharmaceutical radiation sensitizers, which are known to preferentially enhance the effects of radiation in cancerous tissues, are clearly unsuited for the general systemic protection of normal tissues from exposure to ionizing radiation.

What is needed are therapeutic agents to protect subjects who have incurred, or are at risk for incurring exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Protection from Toxic Side Effects of Experimental Chemotherapy

Experimental chemotherapy has been the mainstay of treatment offered to patients diagnosed with surgically unresectable advanced cancers, or cancers refractory to standard chemotherapy and radiation therapy. Of the more effective classes of drugs, curative properties are still limited. This is because of their relatively narrow therapeutic index, restricted dosage, delayed treatments and a relatively large proportion of only partial tumor reductions. This state is usually followed by recurrence, increased tumor burden, and drug resistant tumors.

Several cytoprotective agents have been proposed to enhance the therapeutic index of anticancer drugs. For methotrexate toxicity, such agents include asparaginase, leucovorum factor, thymidine, and carbipeptidase. Because of the extensive use of anthracyclines, specific and non-specific cytoprotective agents have been proposed which have varying degrees of efficacy; included are corticosteroids, desrazoxane and staurosporin. The latter is of interest in that it includes a G1/S restriction blockade in normal cells. (Chen et al., Proc AACR 39:4436A, 1998).

Cisplatin is widely used and has a small therapeutic index which has spurred investigation and search of cytoprotectants. Among the cytoprotectants for cisplatin with clinical potential are mesna, glutathione, sodium thiosulfate, and amifostine (Griggs, Leuk. Res. 22 Suppl 1:S27-33, 1998; List et al., Semin. Oncol. 23(4 Suppl 8):58-63, 1996; Taylor et al., Eur. J Cancer 33(10):1693-8, 1997). None of these or other proposed cytoprotectants such as oxonic acid for fluoropyrimidine toxicity, or prosaptide for paclitaxel PC12 cell toxicity, appears to function by a mechanism which renders normal replicating cells into a quiescent state.

What is needed are effective cytoprotective agents which are effective in protecting animals, inclusive of humans, from the cytotoxic side effects of chemotherapeutic agents.

The aryl and heteroaryl propene amide compounds of the present invention inhibit tumor cell proliferation by inducing tumor cell death without killing normal cells at therapeutically useful concentrations. The compounds of the present invention are effective against a broad range of tumor types. Without wishing to be bound by any theory, it is believed that the compounds affect the Mitogen Activated Protein Kinase (MAPK) signal transduction pathway, thereby affecting tumor cell growth and viability.

SUMMARY OF THE INVENTION

It is an object of the invention to provide compounds, pharmaceutical compositions and therapeutic methods. The biologically active compounds are in the form of aryl and heteroaryl propene amides, and salts thereof.

It is an object of the invention to provide compounds, compositions and methods for the treatment and/or prevention of cancer and other proliferative disorders.

It is an object of the invention to provide compounds which are selective in killing tumor cells but not normal cells at therapeutically useful concentrations.

It is an object of the invention to provide compounds, compositions and methods for inducing neoplastic cells to selectively undergo apoptosis.

It is a further object of this invention to provide compounds, compositions and methods which enable prophylactic treatment of proliferative disorders.

It is a further object of this invention to provide compounds compositions and methods for protecting normal cells and tissues from the cytotoxic and genetic effects of exposure to ionizing radiation, in subjects who have incurred, will in the future incur, or are at risk for incurring exposure to ionizing radiation.

The exposure to ionizing radiation may occur in controlled doses during the treatment of cancer and other proliferative disorders, or may occur in uncontrolled doses beyond the norm accepted for the population at large during high risk activities or environmental exposures.

It is an object of the invention to provide compositions and methods for protecting individuals from the cytotoxic side effects of chemotherapeutic agents, particularly mitotic phase cell cycle inhibitors and topoisomerase inhibitors, used in the treatment of cancer and other proliferative disorders.

It is an object of the invention provide a method for treating cancer or other proliferative disorder which reduces or eliminates cytotoxic effects on normal cells.

It is an object of the invention to enhance the effects of chemotherapeutic agents, particularly mitotic phase cell cycle inhibitors and topoisomerase inhibitors, used for the treatment of cancer or other proliferative disorders.

It is an object of the present invention to provide a therapeutic program for treating cancer or other proliferative disorder which includes administration of a cytoprotective compound prior to administration of a chemotherapeutic agent, which cytoprotective compound induces a reversible cycling quiescent state in non-tumored tissues.

It is an object of the invention to provide a method for safely increasing the dosage of chemotherapeutic agents, particularly mitotic phase cell cycle inhibitors and topoisomerase inhibitors, used in the treatment of cancer and other proliferative disorders.

In one aspect, the invention is directed to novel compounds of formula I:

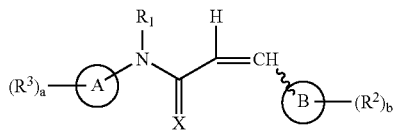

wherein:

ring A and ring B are independently selected from the group consisting of aryl and heteroaryl, provided that ring A is other than pyridyl, quinazolyl or naphthyridyl;

X is O or S, preferably O;

$R^1$ is independently selected from the group consisting of —$R^4$; —$SO_2(C_1-C_6)$alkyl; $C(=O)R^4$; —$C(=O)OR^4$; —$C(=O)O(C_1-C_6)$alkylenearyl, preferably —$C(=O)O(CH_2)$aryl; —$OR^4$; —$(C_2-C_6)$alkynyl; —$(C_3-C_6)$heteroalkenyl; —$(C_2-C_6)$alkylene-$OR^4$; substituted aryl; unsubstituted aryl; substituted heteroaryl; unsubstituted heteroaryl; substituted aryl$(C_1-C_3)$alkyl; unsubstituted aryl$(C_1-C_3)$ alkyl; substituted heteroaryl$(C_1-C_3)$alkyl and unsubstituted heteroaryl $(C_1-C_3)$alkyl;

each $R^2$ is independently selected from —$OR^4$; halogen, preferably fluorine; —C≡N; —$CO_2R^4$; —$C(=O)NR^4_2$; —$C(=NR^4)NR^4_2$; —$O(C_1-C_3)$alkylene -$CO_2R^4$; —$(C_2-C_6)$—$OR^4$; phosphonato; —$NR^4_2$; —$NHC(=O)(C_1-C_6)$ alkyl; sulfamyl; carbarnyl; —$OC(=O)(C_1-C_3)$alkyl, preferably —$OC(=O)CH_3$; —$O(C_2-C_6)$—$N((C_1-C_6)$alkyl$)_2$, preferably —$O(C_2-C_6)$—$N(CH_3)_2$; —$S(C_1-C_3)$alkyl; —$S(=O)(C_1-C_3)$alkyl; and —$SO_2(C_1-C_3)$alkyl;

b is 1, 2, 3, 4 or 5;

provided that when B is phenyl, $R^2$ is other than 2,3-di-$OR^4$, and 3,4-di-$OR^4$; and provided that when $R^3$ is halogon, $R^2$ is not chlorine, bromine or iodine;

∼∼∼ indicates a single bond, whereby the compounds of formula I may be in either the E or the Z conformation;

each $R^3$ is independently selected from halogen; $(C_1-C_6)$ alkyl; —$OR^4$; —C≡N; —$C(=NR^4)NR^4_2$; —$O(C_1-C_3)$ alkylene-$CO_2R^4$; —$(C_1-C_6)$—$OR^4$; nitro; phosphonato; —$NHC(=O)(C_1-C_6)$alkyl; sulfamyl; —$OC(=O)(C_1-C_3)$ alkyl, preferably —$OC(=O)CH_3$; —$O(C_2-C_6)$—$N((C_1-C_6)$ alkyl$)_2$, preferably —$O(C_2-C_6)$—N $(CH_3)_2$; and (i) or (ii) below:

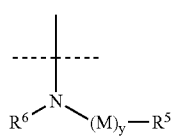

(i)

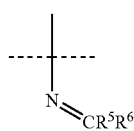

(ii)

wherein:

each M is a bivalent connecting group independently selected from the group consisting of —$(C_1-C_6)$alkylene-, —$(CH_2)_d$- V—$(CH_2)_e$-, —$(CH_2)_f$- W—$(CH_2)_g$- and -Z-;

each y is independently selected from the group consisting of 0 and 1;

each V is independently selected from the group consisting of arylene, heteroarylene, —C(=O)—, —$C(=O)(C_1-C_6)$ perfluoroalkylene, —C(=O)—, —C(=S)—, —S(=O)—, —$SO_2$—, —$C(=O)NR^4$—, —$C(=S)NR^4$— and —$SO_2NR^4$—;

each W is independently selected from the group consisting of —$NR^4$—, —O— and —S—;

each d is independently selected from the group consisting of 0, 1 and 2, preferably from 0 and 1;

each e is independently selected from the group consisting of 0, 1 and 2, preferably from 0 and 1;

each f is independently selected from the group consisting of 1, 2 and 3, preferably from 1 and 2;

each g is independently selected from the group consisting of 0, 1 and 2, preferably from 0 and 1;

—Z— is 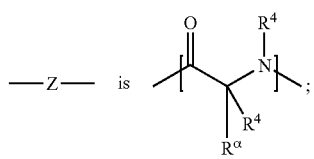;

wherein the absolute stereochemistry of -Z- is S or R, or a mixture of S and R;

each $R^\alpha$ is independently selected from the group consisting of —H, —($C_1$-$C_6$) alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl); and includes compounds wherein $R^\alpha$ and $R^4$ combine to form a 5-, 6- or 7-membered heterocyclic or carbocyclic ring;

a is 1, 2 or 3;

provided that when A is phenyl, $R^3$ is other than 3,4,5-tri-$OR^4$, and when $R^2$ is 4-methoxy, $R^3$ is other than 4-methoxy;

$R^4$ is independently selected from the group consisting of —H, —($C_1$-$C_6$) alkyl, substituted —($C_1$-$C_6$)alkyl, —($C_2$-$C_6$) alkenyl, substituted —($C_2$-$C_6$)alkenyl and heteroalkyl, wherein two $R^4$ groups may together form a heterocycle;

each $R^5$ is independently selected from the group consisting of —$R^4$; unsubstituted aryl; substituted aryl; substituted heterocyclic; unsubstituted heterocyclic; —$CO_2R^4$; —C(=O)$NR^4_2$; —C(=NH)—$NR^4_2$; —($C_1$-$C_6$)perfluoroalkyl; —$CF_2$Cl; —P(=O)($OR^4$)$_2$; —OP(=O)($OR^4$)$_2$; —$CR^4R^7R^8$ and a monovalent peptidyl moiety with a molecular weight of less than 1000, preferably with a molecular weight of less than 800, more preferably with a molecular weight of less than 600, most preferably with a molecular weight of less than 400; provided that when y is 0 and $R^5$ is —$CO_2R^4$, then $R^4$ is not —H;

each $R^6$ is independently selected from the group consisting of —H, —($C_1$-$C_6$)alkyl, and aryl($C_1$-$C_3$)alkyl, each $R^7$ is independently selected from the group consisting of —H, —($C_1$-$C_6$)alkyl, —C(=O)$R^8$, —$OR^4$, —$SR^4$, —OC(=O)($CH_2$)$_2$$CO_2R^6$, guanidino, $NR^4_2$, —$NR^4_3{}^+$, —$N^+$($CH_2CH_2OR^5$)$_3$, halogen, phenyl, substituted phenyl, heterocyclyl, and substituted heterocyclyl; and each $R^8$ is independently selected from the group consisting of $R^\alpha$, halogen, —$NR^4_2$ and heterocycles containing two nitrogen atoms;

wherein the substituents for the substituted aryl and substituted heterocyclic groups comprising or included within Ar, $R^1$, $R^5$ $R^6$, $R^7$ and $R^\alpha$ are independently selected from the group consisting of halogen; ($C_1$-$C_6$) alkyl; ($C_1$-$C_6$)alkoxy; —$NO_2$; —C≡N; —C(=O)O($C_1$-$C_3$)alkyl; —$OR^4$; —($C_2$-$C_6$) -$OR^4$; phosphonato; —$NR_2$; —NHC(=O)($C_1$-$C_6$)alkyl; sulfamyl; carbamyl; —OC(=O)($C_1$-$C_3$)alkyl, preferably —OC(=O)$CH_3$; —O($C_2$-$C_6$)—N(($C_1$-$C_6$) alkyl)$_2$, preferably —O($C_2$-$C_6$)—N($CH_3$)$_2$; and ($C_1$-$C_3$)perfluoroalkyl; or a salt of such a compound.

When $R^5$ is a monovalent peptidyl moiety, the attachment point on the peptidyl moiety may be via a carboxyl group or through an amino group. Further, the carboxyl or amino groups may be either terminal carboxyl/amino groups or may be side chain groups such as, for example, the side chain amino group of lysine or the side chain carboxyl group of aspartic acid. The attachment point on the peptidyl moiety will correlate with the particular selection of the M tether. Thus, for $R^5$ as a peptidyl moiety of molecular weight less than 1000, it is provided that:

(1) when V is —C(=O)—, —C(=S)—, —S(=O)—or —$SO_2$—, and e is 0, then the peptidyl moiety is coupled to M through the peptide's amino terminus or through a sidechain amino group to form an amide, thioamide, sulfinamide or sulfonamide, respectively;

(2) when V is —C(=O)NR—, —$SO_2NR^4$—, or —$NR^4$—, and e is 0, then the peptidyl moiety is coupled to M through the peptide's carboxy terminus or through a sidechain carboxyl group to form an imide, sulfonimide, or carboxamide, respectively; and (3) when W is —S— or —O—, and g is 0, then the peptidyl moiety is coupled to M through the peptide's carboxy terminus or through a sidechain carboxyl group to form a carbothioic acid ester or a carboxylic ester, respectively.

According to one sub-embodiment of the compounds of the invention, there is provided a compound, wherein -Z- is:

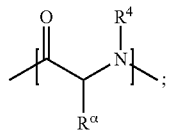

wherein the absolute stereochemistry of -Z- is either S or R; and each $R^\alpha$ is independently selected from the group consisting of —H, —$CH_3$, —$(CH_2)_3$—N—C($NH_2$)(—NH), —$CH_2$C(=O)$NH_2$, —$CH_2$COOH, —$CH_2$SH, —$(CH_2)$2C(=O)—$NH_2$, —$(CH_2)_2$COOH, —$CH_2$-(2-imidazolyl), —CH($CH_3$)—$CH_2CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2CH_3$; and includes compounds wherein $R^\alpha$ and $R^4$ combine to form a 5-, 6- or 7-membered heterocyclic ring.

Such compounds include, for example, (E)-N-(4-methoxy-3-nitrophenyl)-3-(3,4,5-trimethoxyphenyl)-2-propenamide;

(E)-N-(4-methoxy-3-aminophenyl)-3-(3,4,5-trimethoxyphenyl)-2-propenamide;

(E)-N-(4-methoxy-3-nitrophenyl)-3-(2,3,4,5,6-pentafluorophenyl)-2-propenamide;

(E)-N-(4-bromophenyl)-3-(3-methoxy-4-fluorophenyl)-2-propenamide;

(E)-N-(4-bromophenyl)-3-(3-cyano-4-fluorophenyl)-2-propenamide;

(E)-N-(4-bromophenyl)-3-(3-carboxy-4-fluorophenyl)-2-propenamide;

(E)-N-(4-methoxy-3- nitrophenyl)-3-(3-fluoro-4-nitrophenyl)-2-propenamide;

(E)-N-(4-bromophenyl)-3-(2,4-difluorophenyl)-2-propenamide;

(E)-N-(4-methoxy-3-aminophenyl)-3-(3-fluoro-4-aminophenyl)-2-propenamide; and salts thereof.

According to a preferred sub-embodiment, there is provided a compound of formula I, wherein each V is independently selected from the group consisting of —C(=O)—, —C(=S)—, —S(=O)—, —$SO_2$—, —C(=O)$NR^4$—, —C(=S)$NR^4$— and —$SO_2NR^4$—.

According to a more preferred sub-embodiment, there is provided a compound of formula I, wherein $R^2$ is independently selected from —$OR^4$; —C≡N; —$CO_2R^4$; —C(=O)$NR^4_2$; —C(=$NR^4$)$NR^4_2$; —O($C_1$-$C_3$) alkylene-$CO_2R^4$; —($C_2$-$C_6$)—$OR^4$; phosphonato; —$NR^4_2$; —NHC(=O)($C_1$-$C_6$)alkyl; sulfamyl; carbamyl; —OC(=O)($C_1$-$C_3$)alkyl, preferably —OC(=O)$CH_3$; —O($C_2$-$C_6$)—N(($C_1$-$C_6$)alkyl)$_2$, preferably —O($C_2$-$C_6$)—N($CH_3$)$_2$; —S($C_1$-$C_3$)alkyl; —S(=O)($C_1$-$C_3$)alkyl; and —$SO_2$($C_1$-$C_3$)alkyl;

provided that when B is phenyl, $R^2$ is other than 2,3-di-$OR^4$, 3,4-di-$OR^4$, 3,4,5-tri-$OR^4$;

b is 1, 2, or 3; and
each $R^7$ is independently selected from the group consisting of —H, —$(C_1-C_6)$alkyl and —$(C_1-C_6)$acyl.

Such compounds include, for example, (E)-N-(4-methoxy-3-trifluoroacetamidophenyl)-3-(2,4,6-trimethoxyphenyl)-2-propenamide; and salts thereof.

According to a further preferred sub-embodiment, there is provided a compound of formula I, wherein each $R^5$ is independently selected from the group consisting of —$R^4$; unsubstituted aryl; substituted aryl; substituted heterocyclic; unsubstituted heterocyclic; —$CO_2R^4$; —$C(=O)NR^4_2$; —$C(=NH)$—$NR^4_2$; and a monovalent peptidyl moiety with a molecular weight of less than 1000, preferably with a molecular weight of less than 800, more preferably with a molecular weight of less than 600, most preferably with a molecular weight of less than 400; provided that when y is 0 and $R^5$ is —$CO_2R^4$, then $R^4$ is not —H; and wherein the substituents for the substituted aryl and substituted heterocyclic groups comprising or included within Ar, $R^1$, $R^5$ and $R^\alpha$ are independently selected from the group consisting of halogen; $(C_1-C_6)$alkyl; $(C_1-C_6)$alkoxy; —$NO_2$; —$C\equiv N$; —$C(=O)O(C_1-C_3)$alkyl; —$OR^4$; —$(C_2-C_6)$—$OR^4$; phosphonato; —$NR^4_2$; —$NHC(=O)(C_1-C_6)$alkyl; sulfamyl; carbamyl; —$OC(=O)(C_1-C_3)$alkyl, preferably —$OC(=O)CH_3$; —$O(C_2-C_6)$—$N((C_1-C_6)$alkyl$)_2$, preferably —$O(C_2-C_6)$—$N(CH_3)_2$; and $(C_1-C_3)$perfluoroalkyl; or a salt of such a compound.

According to another sub-embodiment of the compounds of the invention, there is provided a compound, wherein one $R^3$ substituent, designated $R^{3p}$, is positioned in a substitution orientation relative to the

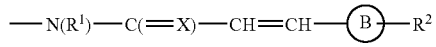

moiety which is closest to the planar angle formed by a para substituent in a six-membered aromatic ring and forms a planar angle with the

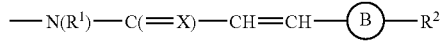

moiety of between about 135° and about 180°; or a salt of such a compound.

In such embodiments:
$R^{3p}$ is selected from the group consisting of halogen; $(C_1-C_6)$alkyl; $(C_1-C_6)$alkoxy; —$C\equiv N$; —$C(=O)NR^4_2$; —$C(=NR^4)NR^4_2$; —$(C_1-C_3)$alkylene-$CO_2R^4$; —$OR^4$; —$(C_2-C_6)$—$OR^4$; phosphonato; —$NR^4_2$; —$NHC(=O)(C_1-C_6)$alkyl; sulfamyl; —$OC(=O)(C_1-C_3)$alkyl, preferably —$OC(=O)CH_3$; —$O(C_2-C_6)$—$N((C_1-C_6)$alkyl$)_2$, preferably —$O(C_2-C_6)$—$N(CH_3)_2$; and $(C_1-C_3)$perfluoroalkyl.

Ring A, Ring B, X, M, d, e, f, g, V, W, Z, $R^1$, $R^2$, $R^4$, $R^5$, $R^6$, $R^7$, a, b, y, $R^\alpha$, and any remaining $R^3$ substituents are as defined above for formula I.

Such compounds include, for example:
(E)-N-(4-methoxyphenyl)-3-(2,4,6-trimethoxyphenyl)-2-propenamide;
(E)-N-(4-methoxyphenyl)-3-(2,6-dimethoxyphenyl)-2-propenamide;
(E)-N-(3-hydoxy-4-methoxyphenyl)-3-(2,4,6-trimethoxyphenyl)-2-propenamide; and salts thereof According to another sub-embodiment, a compound of formula I is provided wherein at least one $R^3$ substituent, designated $R^{3m}$ is positioned in a substitution orientation relative to that of the

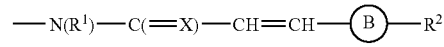

moiety which is closest to the dihedral angle formed by a meta substituent in a six-membered aromatic ring and forms a planar angle with the

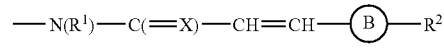

moiety of between about 90° and about 145°.

Each $R^{3m}$ is selected from the group consisting of nitro and (i) and (ii) below:

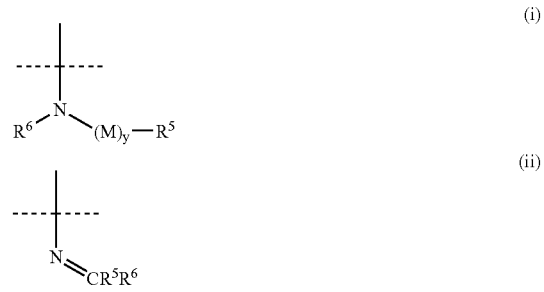

Ring A, Ring B, X, M, d, e, f, g, V, W, Z, $R^1$, $R^2$, $R^4$, $R^5$, $R^6$, $R^7$, a, b, y, $R^\alpha$, and any remaining $R^3$ substituents are as defined for formula I above.

In one sub-embodiment of compounds of the invention, a compound of formula I is provided wherein ring A is phenyl, and wherein ring B, and M, d, e, f, g, V, W, Z, $R^1$, $R^2$, $R^3$, $R^{3m}$, $R^{3p}$, $R^4$, $R^5$, $R^6$, $R^7$, a, b, y and $R^\alpha$ are as defined, as for formula I above; or a salt of such a compound.

In another sub-embodiment of compounds of the invention, a compound of formula I is provided wherein ring B is phenyl, and wherein ring A, and M, d, f, g, V, W, Z, $R^1$, $R^2$, $R^3$, $R^{3m}$, $R^{3p}$, $R^4$, $R^5$, $R^6$, $R^7$, a, b, y and $R^\alpha$ are as defined as for formula I above; or a salt of such a compound.

In a further sub-embodiment thereof, a compound of formula I is provided wherein ring A and ring B are phenyl, or a salt of such a compound.

In another embodiment of the invention, a compound of formula I, and salts thereof, is provided wherein at least one $R^2$ substituent designated $R^{2o}$, is located at a position on ring B, ortho to the

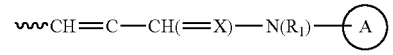

moiety; and wherein X, M, d, e, f, g, V, W, Z, $R^1$, $R^2$, $R^3$, $R^{3m}$, $R^{3p}$, $R^4$, $R^5$, $R^6$, $R^7$, a, b, y and $R^\alpha$ are as defined as for formula I above.

In another embodiment of the invention, there is provided a compound according to the formula Ia:

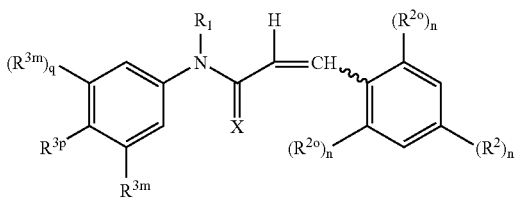

wherein q is 0 or 1;

n is independently selected from 0 and 1; wherein the sum of n is selected from 1, 2 and 3; and X, $R^1$, $R^2$, $R^{2o}$, $R^{3m}$ and $R^{3p}$ are as defined as for formula I above;

or a salt thereof,

In a sub-embodiment thereof, there are provided a compound wherein each $R^{3m}$ is independently selected from the group consisting of (i) and (ii) below:

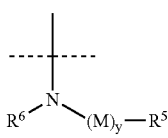

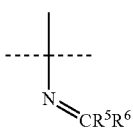

$R^{3p}$ is selected from the group consisting of halogen; ($C_1$-$C_6$)alkyl; ($C_1$-$C_6$)alkoxy; —C≡N; —C(=O)$NR^4_2$; —C(=$NR^4$)$NR^4_2$; —O($C_1$-$C_3$)alkylene-$CO_2R^4$; —$OR^4$; —($C_2$-$C_6$)—$OR^4$; phosphonato; —$NR^4_2$; —NHC(=O)($C_1$-$C_6$)alkyl; sulfamyl; —OC(=O)($C_1$-$C_3$)alkyl, preferably —OC(=O)$CH_3$; —O($C_2$-$C_6$)—N(($C_1$-$C_6$)alkyl)$_2$, preferably —O($C_2$-$C_6$)—N($CH_3$)$_2$; and ($C_1$-$C_3$)perfluoroalkyl;

each $R^{2o}$ is independently selected from the group consisting of ($C_1$-$C_6$)alkoxy; —$NR^4_2$; —OC(=O)($C_1$-$C_3$)alkyl, preferably —OC(=O)$CH_3$; and —O($C_2$-$C_6$)—N(($C_1$-$C_6$) alkyl)$_2$, preferably —O($C_2$-$C_6$)—N($CH_3$)$_2$;

$R^2$ is selected from the group consisting of halogen, ($C_1$-$C_6$)alkyl, ($C_1$-$C_6$)alkoxy, —$NR^4_2$, —C≡N, —$CO_2R^4$, —C(=O)$NR^4_2$, —C(=$NR^4$)$NR^4_2$, and perfluoro($C_1$-$C_3$) alkyl; and X, M, d, e, f, g, V, W, Z, $R^1$, $R^4$, $R^5$, $R^6$, $R^7$, $R^8$, a, b, y, n, q and $R^\alpha$ are as defined above for formula I;

or a salt of such a compound.

Such compounds include, for example, (E)-N-(4-methoxy-3-aminophenyl)-3-(2,4,6-trimethoxyphenyl)-2-propenamide, and salts thereof In a further sub-embodiment of compounds of the invention, a compound of the formula Ie, below, and salts thereof is provided:

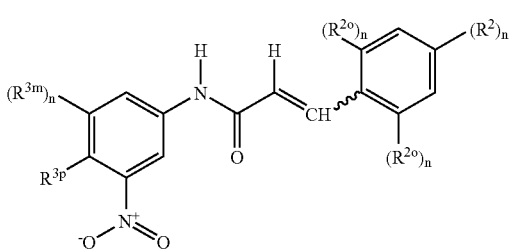

wherein ~~~$R^2$, $R^{2o}$, $R^3$m, $R^{3p}$, q and n are as defined above for formula I.

Such compounds include:

(E)-N-(4-methoxy-3-nitrophenyl)-3-(2,4,6-trimethoxyphenyl)-2-propenamide, and salts thereof.

In another embodiment of compounds of the present invention, there is provided a compound of formula I

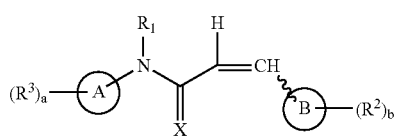

wherein:

X is S, and

Ring A, Ring B, $R^1$, $R^2$, $R^3$ a and b substituents are as defined above for formula I;

or a salt of such a compound.

In a sub-embodiment thereof, there is provided a compound of formula Is

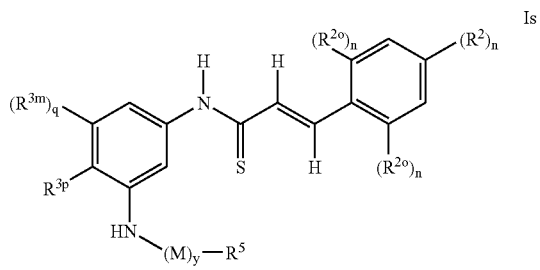

wherein $R^2$, $R^{2o}$, n, $R^{3p}$, $R^{3m}$, M, y, and $R^5$ are as defined above for formula Ic;

or a salt of such a compound.

According to other embodiments of the invention, processes for preparing compounds according to formula I are provided.

In one such embodiment, a process for preparing a compound of formula I, or a salt thereof, wherein the olefin double bond is in the E conformation, is provided comprising:

(1) coupling a compound of formula II:

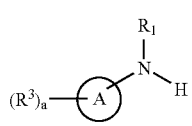

wherein A, $R^1$, $R^3$, and a are defined as for formula I above; with an alkyl ester of a malonic acid halide:

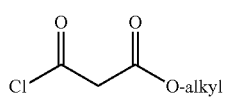

to yield a carboxylic ester compound of formula III:

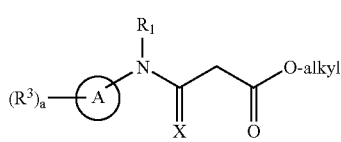

(2) hydrolyzing the carboxylic ester compound of formula III to form a carboxylic acid compound of formula IV:

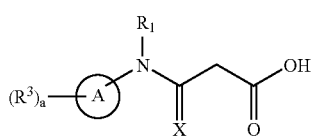

(3) coupling of the caboxylic acid compound of formula IV with an aromatic aldehyde of formula V:

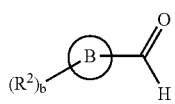

wherein $R^2$, B and b are defined as in formula I above; in an acidic solvent or acidic solvent mixture, particularly glacial acetic acid at elevated temperature to form a compound of formula I or a salt of such a compound.

In the aforesaid process, certain malonic acid halides, particularly malonic acid chlorides, used in the initial acylation step, are available commercially and are also readily prepared by methods known to one of skill in the art. These methods include reaction of the precursor malonic acid mono ester with a chlorinating agent such as thionyl chloride, phosphorous pentachloride or phosphorous trichloride. Other acid halides are also synthetically accessible, including acid fluorides via reaction with, for example, hexafluoroacetone and acid bromides via; reaction with, for example, thionyl bromide. The alkyl ester moiety of the alkyl malonic acid halide is preferably a ($C_1$-$C_{10}$)alkyl ester, more preferably a ($C_1$-$C_6$) alkyl ester, most preferably a commercially available reagent such as, for example, a methyl or ethyl ester.

The depiction of the malonic acid halide reagent shows a chlorine residue as the leaving group. In addition to acid chlorides as shown, other leaving groups are possible and useful in this method including for example, fluorides, bromides and mixed anhydrides. The acid chloride is preferred.

The hydrolysis of step 2 is performed in an aqueous base such as, for example lithium hydroxide, sodium hydroxide or potassium hydroxide. The solvent medium may be aqueous or a mixture of water and a water-miscible organic solvent such as ethanol or tetrahydrofuran (THF).

According to a further embodiment of the invention, a process for preparing a compound of formula I, or a salt thereof, is provided comprising:

(1) halogenating a carboxylic acid of formula VI with a halogenating agent:

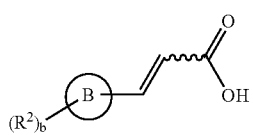

to form an acid halide of formula VII:

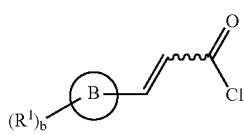

(2) coupling the acid halide VII to an aromatic amino compound of formula II

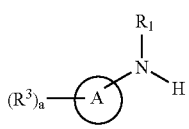

to form an amide compound of formula I or a salt of such a compound.

The acid halide VII may be an acid fluoride, an acid chloride or an acid bromide. In addition, other activated carboxylic acids are useful in this method, including for example mixed anhydrides and/or the use of a catalyzing reagent such as 4-dimethyl amino pyridine (DMAP).

The carboxylic acid (and the intermediate acid halide of formula VII) is shown in formula VI as being either in the E or the Z conformation, thus this process is capable of producing compounds of formula I in which the olefin double bond is in either the E or the Z conformation.

In the step 2 coupling of the acid halide VII with the aromatic amine II, an acid scavenger such as, for example, triethyl amine (TEA) or diisopropylethyl amine (DIPEA) is generally used to react with the byproduct acid formed in the reaction, i.e., hydrochloric acid (HCl) in the instance of reaction with an acid chloride.

For the synthesis of an acid halide such as VII, suitable halogenating agents include thionyl chloride, thionyl bromide, phosphorous pentachloride, phosphorous oxychloride and hexafluoroacetone.

According to another embodiment of the invention, a process for preparing a compound of formula I, or a salt thereof, is provided, comprising:

reacting an aromatic amino compound of formula II

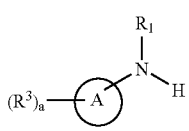

with a carboxylic acid compound of formula VI:

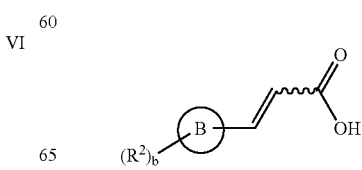

and an amide coupling agent, to form a compound of formula I or a salt of such a compound.

In the aforesaid process of coupling compounds of formula II to compounds of formula VI, "amide coupling reagents" are compounds used to couple unactivated carboxylic acid moieties to amino groups, such as the aromatic amino moiety of a compound of formula I wherein —$R^{3m}$ is $NH_2$ (i.e., wherein —$R^{3m}$ is formula (i), y is 0, $R^4$ is —H and $R^5$ is $R^4$=—H). Such amide coupling reagents include for example, reagents such as, for example, diisopropyl carbodiimide (DIC), dicyclohexyl carbodiimide (DCC) and O-(7-azabenzotriazol-1-yl)-N,N,N',N'-tetramethyluronium hexafluoro-phosphate (HATU).

Also, the aromatic propionic acid is shown in formula VI as being either in the E- or the Z-conformation. This process is therefore capable of producing compounds of formula I in which the olefin double bond is in either the E or the Z conformation.

Additionally, in the aforesaid process of coupling compounds of formula II to compounds of formula VI, certain functional groups which would be sensitive to the reaction conditions may be protected by protecting groups. The term "protecting group" refers to a derivative of a chemical functional group which is employed to derivatize chemical functionalities which would otherwise be incompatible with the conditions of a desired reaction. The protecting group renders such a functional group stable to the desired reaction conditions and may later be removed to regenerate the de-protected functionality. One example of the use of protecting groups is in the common reaction of the amino group of a first amino acid with the carboxyl group of a second amino acid to form an amide bond. However, since each reactant contains both an amino and a carboxylate functional group, the reaction between them is (1) nonspecific as to which amino group will react with which carboxyl group, and (2) subject to polymerization since the product of the reaction still contains both reactive moieties. A protecting group on the carboxylate of the first amino acid and a protecting group acid on the amino group of the second amino acid will serve to limit the reagents to the single desired reaction of the amino group of the first amino acid with the carboxylic acid of the second amino acid and yields a product which will not react further because both of the remaining reactive moieties are blocked by protecting groups which may be subsequently be selectively removed. The present reaction would reflect such a need for a protecting group if substitution on the A- or the B-ring included, for example, an amino group, or a carboxyl group in addition to those desired to effect coupling to form the targeted propene amide backbone.

Any chemical functionality that is a structural component of any of the reagents used to synthesize compounds of this invention may be optionally protected with a chemical protecting group if such a protecting group is useful in the synthesis of compounds of this invention. Appropriate protecting groups for amine functionalities include, for example, such moieties as tert-butoxy carbonyl (t-Boc), benzyl, 9-fluorenylmethoxycarbonyl (Fmoc) or benzyloxycarbonyl (CBZ). Appropriate protecting groups for carboxyl groups include, for example tert-butyl esters. Techniques for selecting, incorporating and removing chemical protecting groups may be found in "Protecting Groups In Organic Synthesis" by Theodora Green, the entire disclosure of which is incorporated herein by reference.

In addition to use of a protecting group, sensitive functional groups may be introduced as synthetic precursors to the functional group desired in the final product. An example of this is an aromatic nitro (—$NO_2$) group. The aromatic nitro group goes not undergo any of the nucleophilic reactions of an aromatic amino group. However, the nitro group is essentially a protected amino group because it is readily reduced to the amino group under mild conditions that are selective for the nitro group over most other functional groups.

According to another embodiment of the invention, pharmaceutical compositions are provided, comprising a pharmaceutically acceptable carrier and a compound according to formula I:

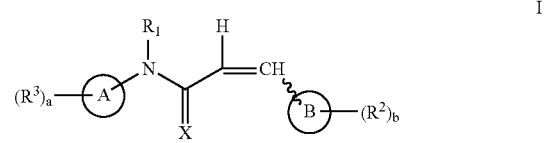

wherein:
ring A ring B, $R^1$, $R^2$, $R^3$, X, a and b are as described above for Formula I; or a salt of such a compound.

In another embodiment of compounds of the invention, there is provided a conjugate of the formula, I-L-Ab or Ic-L-Ab;
wherein,
I and Ic are compounds of formula I and formula Ic as defined herein;
Ab is an antibody; and
-L- is a single covalent bond or a linking group covalently linking said compound to said antibody.

In yet another embodiment of the invention, a conjugate of the formula I-L-Ab is provided wherein I is a compound of formula I; Ab is an antibody; and -L- is a single bond or a linking group covalently linking said compound of formula I to said antibody.

In a sub-embodiment thereof, a conjugate of the formula Ic-L-Ab is provided wherein Ic is a compound of formula Ic; Ab is an antibody; and -L- is a single bond or a linking group covalently linking said compound of formula Ic to said antibody.

In a preferred sub-embodiment of the aforesaid conjugates of the formulae I-L-Ab and Ic-L-Ab, said antibody (Ab) is a monoclonal antibody or a monospecific polyclonal antibody.

In a more preferred sub-embodiment of the aforesaid conjugates of the formulae I-L-Ab and Ic-L-Ab, the aforesaid antibody (Ab) is a tumor-specific antibody.

In yet a further embodiment of the present invention, there is provided a compound of formula I derivatized as a substrate for a β-lactanase enzyme.

A pharmaceutical composition is additionally provided as described supra, comprising a pharmaceutically acceptable carrier and at least one conjugate according to formulae I-L-Ab or fc-L-Ab.

According to another embodiment of the invention, there is provided a method of treating an individual for a proliferative disorder, particularly cancer, comprising administering to the individual an effective amount of at least one compound of formula I':

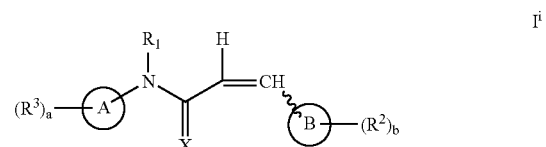

wherein:
ring A and ring B are independently selected from the group consisting of aryl and heteroaryl;

X is O or S, preferably O;

$R^1$ is independently selected from the group consisting of —$R^4$, —$SO_2(C_1$-$C_6)$alkyl, $C(=O)R^4$, —$C(=O)OR^4$, —$C(=O)O(C_1$-$C_6)$alkylenearyl, —$OR^4$, —$(C_2$-$C_6)$alkynyl, —$(C_3$-$C_6)$heteroalkenyl, —$(C_2$-$C_6)$alkylene-$OR^4$, substituted aryl, unsubstituted aryl, substituted heteroaryl, unsubstituted heteroaryl, substituted aryl$(C_1$-$C_3)$alkyl, unsubstituted aryl$(C_1$-$C_3)$alkyl, substituted heteroaryl$(C_1$-$C_3)$alkyl and unsubstituted heteroaryl$(C_1$-$C_3)$alkyl;

$R^2$ is independently selected from $(C_1$-$C_6)$alkyl; halogen; —$OR^4$; —$C\equiv N$; —$NO_2$; —$CO_2R^4$; —$C(=O)NR^4{}_2$; $C(=NR^4)NR^4{}_2$; —$O(C_1$-$C_3)$alkylene-$CO_2R^4$; —$(C_2$-$C_6)$— $OR^4$; phosphonato; —$NR_4{}^2$; —$NHC(=O)(C_1$-$C_6)$alkyl; sulfamyl; carbamyl; —$OC(=O)(C_1$-$C_3)$alkyl, preferably —$OC(=O)CH_3$; —$O(C_2$-$C_6)$—$N((C_1$-$C_6)$alkyl$)_2$, preferably —$O(C_2$-$C_6)$—$N(CH_3)_2$; —$S(C_1$-$C_3)$alkyl; —$S(=O)(C_1$-$C_3)$alkyl; and —$SO_2(C_1$-$C_3)$alkyl;

b is 1, 2, 3, 4 or 5; and

~~~ indicates a single bond, whereby the compounds of formula I may be in either the E or the Z conformation;

$R^3$ is independently selected from halogen; $(C_1$-$C_6)$alkyl; —$OR^4$; —$C\equiv N$; —$C(=NR^4)NR^4{}_2$; —$O(C_1$-$C_3)$alkylene-$CO_2R^4$; —$(C_1$-$C_6)$—$OR^4$; nitro; phosphonato; —$NHC(=O)$ $(C_1$-$C_6)$alkyl; sulfamyl; —$OC(=O)(C_1$-$C_3)$alkyl, preferably —$OC(=O)CH_3$; —$O(C_2$-$C_6)$—$N((C_1$-$C_6)$alkyl$)_2$, preferably —$O(C_2$-$C_6)$—$N(CH_3)_2$; $(C_1$-$C_3)$perfluoroalkyl; and (i) or (ii) below:

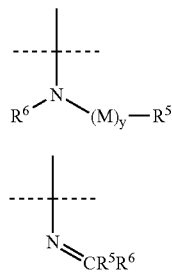

wherein:

each M is a bivalent connecting group independently selected from the group consisting of —$(C_1$-$C_6)$alkylene-, —$(CH_2)_d$—V—$(CH_2)_e$—, —$(CH_2)_f$—W—$(CH_2)_g$— and -Z-;

each y is independently selected from the group consisting of 0 and 1;

each V is independently selected from the group consisting of arylene, heteroarylene, —$C(=O)$—, —$C(=O)(C_1$-$C_6)$ perfluoroalkylene, —$C(=O)$—, —$C(=S)$—, —$S(=O)$—, —$SO_2$—, —$C(=O)NR^4$—, —$C(=S)NR^4$— and —$SO_2NR^4$—;

each W is independently selected from the group consisting of —$NR^4$—, —O— and —S—;

each d is independently selected from the group consisting of 0, 1 and 2, preferably from 0 and 1;

each e is independently selected from the group consisting of 0, 1 and 2, preferably from 0 and 1;

each f is independently selected from the group consisting of 1, 2 and 3, preferably from 1 and 2;

each g is independently selected from the group consisting of 0, 1 and 2, preferably from 0 and 1;

—Z— is 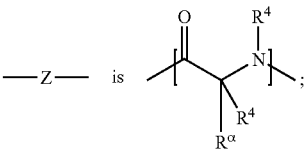

wherein the absolute stereochemistry of -Z- is S or R, or a mixture of S and R;

each $R^\alpha$ is independently selected from the group consisting of —H, —$(C_1$-$C_6)$alkyl, —$(CH_2)_3$—NH—$C(NH_2)$ $(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$—(2-imidazolyl), —$(CH_2)_4$—$NH_2$, —$(CH_2)_2$—S—$CH_3$, phenyl, $CH_2$-phenyl, —$CH_2$—OH, —$CH(OH)$—$CH_3$, —$CH_2$-(3-indolyl), —$CH_2$-(4-hydroxyphenyl); and includes compounds wherein $R^\alpha$ and $R^4$ combine to form a 5-, 6- or 7-membered heterocyclic or carbocyclic ring;

a is 1, 2 or 3;

$R^4$ is independently selected from the group consisting of —H, —$(C_1$-$C_6)$alkyl, substituted —$(C_1$-$C_6)$alkyl, —$(C_2$-$C_6)$ alkenyl, substituted —$(C_2$-$C_6)$alkenyl and heteroalkyl wherein two $R^4$ groups may together form a heterocycle;

each $R^5$ is independently selected from the group consisting of —$R^4$; unsubstituted aryl; substituted aryl; substituted heterocyclic; unsubstituted heterocyclic; —$CO_2R^4$; —$C(=O)NR^4{}_2$; —$C(=NH)$—$NR^4{}_2$; —$(C_1$-$C_6)$perfluoroalkyl; —$CF_2Cl$; —$P(=O)(OR^4)_2$; —$OP(=O)(OR^4)_2$; —$CR^4R^7R^8$; and a monovalent peptidyl moiety with a molecular weight of less than 1000, preferably with a molecular weight of less than 800, more preferably with a molecular weight of less than 600, most preferably with a molecular weight of less than 400; provided that when y is 0 and $R^5$ is —$CO_2R^4$; then $R^4$ is not —H;

each $R^6$ is independently selected from the group consisting of —H, —$(C_1$-$C_6)$alkyl, and aryl$(C_1$-$C_3)$alkyl, each $R^7$ is independently selected from the group consisting of —H, —$(C_1$-$C_6)$alkyl, —$C(=O)R^8$, —$OR^4$, —$SR^4$, —$OC(=O)(CH_2)_2CO_2R^6$, guanidino, $NR^4{}_2$, —$NR^4{}_3{}^+$, —$N^+$ $(CH_2CH_2OR^5)_3$, halogen, phenyl, substituted phenyl, heterocyclyl, and substituted heterocyclyl; and each $R^8$ is independently selected from the group consisting of $R^\alpha$, halogen, —$NR^4{}_2$ and heterocycles containing two nitrogen atoms;

wherein the substituents for the substituted aryl and substituted heterocyclic groups comprising or included within Ar, $R^1$, $R^5$ $R^6$, $R^7$ and $R^\alpha$ are independently selected from the group consisting of halogen; $(C_1$-$C_6)$alkyl; $(C_1$-$C_6)$alkoxy; —$NO_2$; —$C\equiv N$; —$C(=O)O(C_1$-$C_3)$alkyl; —$OR^4$; —$(C_2$-$C_6)$—$OR^4$; phosphonato; —$NR^4{}_2$; —$NHC(=O)(C_1$-$C_6)$ alkyl; sulfamyl; carbamyl; —$OC(=O)(C_1$-$C_3)$alkyl, preferably —$OC(=O)CH_3$; —$O(C_2$-$C_6)$—$N((C_1$-$C_6)$alkyl$)_2$, preferably —$O(C_2$-$C_6)$—$N(CH_3)_2$; and $(C_1$-$C_3)$perfluoroalkyl; or a salt of such a compound.

According to preferred embodiment of the above method of treating an individual for a proliferative disorder, particularly cancer, -Z- is:

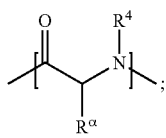

wherein the absolute stereochemistry of -Z- is either S or R; and each $R^\alpha$ is independently selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2CH_3$, —$CH_2$CH($CH_3)_2$, —$(CH_2)_4$—$NH_2$, —$(CH_2)_2$—S—$CH_3$, phenyl, —$CH_2$-phenyl, —$CH_2$—CH(OH)—$CH_3$, —$CH_2$-(3-indolyl), —$CH_2$-(4-hydroxyphenyl), —CH($CH_3)_2$ and —$CH_2CH_3$; and includes compounds wherein $R^\alpha$ and $R^4$ combine to form a 5-, 6- or 7-membered heterocyclic ring;

b is 1, 2 or 3;

each $R^7$ is independently selected from the group consisting of —H, —$(C_1-C_6)$alkyl and —$(C_1-C_6)$acyl;

each V is independently selected from the group consisting of —C(=O)—, —C(=S)—, —S(=O, —$SO_2$—, —C(=O)$NR^4$—, —C(=S)$NR^4$— and —$SO_2NR^4$—;

each $R^5$ is independently selected from the group consisting of —$R^4$, unsubstituted aryl, substituted aryl, substituted heterocyclic, unsubstituted heterocyclic, —$CO_2R^4$, —C(=O)$NR^4_2$, —C(=NH)—$NR^4_2$, and a monovalent peptidyl moiety with a molecular weight of less than 1000; provided that when y is 0 and $R^5$ is —$CO_2R^4$; then $R^4$ is not —H; and wherein the substituents for the substituted aryl and substituted heterocyclic groups comprising or included within Ar, $R^1$, $R^5$ and $R^\alpha$ are independently selected from the group consisting of halogen, —$(C_1-C_6)$alkyl, —$(C_1-C_6)$alkoxy, —$NO_2$, —C≡N, —C(=O)O$(C_1-C_3)$alkyl, —$OR^4$, —$(C_2-C_6)$—$OR^4$, phosphonato, —$NR^4_2$, —NHC(=O)$(C_1-C_6)$alkyl, sulfamyl, carbamyl, —OC(=O)$(C_1-C_3)$alkyl, —$O(C_2-C_6)$—N$((C_1-C_6)$alkyl$)_2$ and —$(C_1-C_3)$perfluoroalkyl; or a salt of such a compound.

According to another embodiment, a method of treating an individual for a proliferative disorder, particularly cancer, is provided, comprising administering to said individual an effective amount of at least one conjugate of the formula I-L-Ab or Ic-L-Ab, as described herein, alone or in combination with a pharmaceutically acceptable carrier.

According to a further embodiment of the invention, a method of inducing apoptosis of tumor cells in an individual afflicted with cancer is provided, comprising administering to the individual an effective amount of at least one compound of formula $I^{ii}$ as described below, alone or in combination with a pharmaceutically acceptable carrier.

According to another embodiment of inducing apoptosis of cancer cells, more preferably tumor cells, in an individual afflicted with cancer is provided, comprising administering to said individual an effective amount of at least one conjugate of the formula I-L-Ab, or Ic-L-Ab, as described herein, alone or in combination with a pharmaceutically acceptable carrier.

According to another embodiment of the invention, a method of inhibiting the growth of tumor cells in an individual afflicted with cancer is provided, comprising administering to the individual an effective amount of at least one compound of formula $I^{ii}$ as described below, alone or in combination with a pharmaceutically acceptable carrier.

According to another embodiment of the invention, a method of inhibiting growth of tumor cells in an individual afflicted with cancer is provided comprising administering to said individual an effective amount of at least one conjugate of the formula I-L-Ab or Ic-L-Ab, as described herein, alone or in combination with a pharmaceutically acceptable carrier.

According to another embodiment of the invention, a method of reducing or eliminating the effects of ionizing radiation on normal calls in an individual who has incurred or is at risk for incurring exposure to ionizing radiation, is provided. This method comprises administering to the individual either prior to, or after the exposure to ionizing radiation, at least one aryl or heteroaryl propene amide of formula $I^{ii}$ as described below, alone or in combination with a pharmaceutically acceptable carrier.

According to a sub-embodiment thereof, there is provided a method of safely increasing the dosage of therapeutic ionizing radiation used in the treatment of cancer or another proliferative disorder, comprising administering an effective amount of at least one radioprotective compound of formula $I^{ii}$ as described below, alone or in combination with a pharmaceutically acceptable carrier. This radioprotective compound induces a temporary radioresistant phenotype in the normal tissue of the individual.

According to another sub-embodiment thereof, there is provided a method for treating a subject who has incurred, or is at risk for incurring remediable radiation damage from exposure to ionizing radiation. This method comprises administering an effective amount of at least one radioprotective compound of formula $I^{ii}$ as described below, either prior to, or after the individual incurs remediable radiation damage from exposure to ionizing radiation.

According to another embodiment of the invention, a method of reducing or eliminating the effects of ionizing radiation on normal calls in an individual who has incurred or is at risk for incurring exposure to ionizing radiation, is provided. This method comprises administering to the individual either prior to, or after the exposure to ionizing radiation, an effective amount of at least one conjugate of the formula I-L-Ab or Ic-L-Ab, as described herein.

According to a sub-embodiment thereof, there is provided a method of safely increasing the dosage of therapeutic ionizing radiation used in the treatment of cancer or another proliferative disorder, comprising administering an effective amount of at least one conjugate of the formula I-L-Ab or Ic-L-Ab, as described herein, alone or in combination with a pharmaceutically acceptable carrier. This radioprotective compound induces a temporary radioresistant phenotype in the normal tissue of the individual.

According to another sub-embodiment thereof, there is provided a method for treating a subject who has incurred, or is at risk for incurring remediable radiation damage from exposure to ionizing radiation. This method comprises administering an effective amount of at least one conjugate of the formula I-L-Ab or Ic-L-Ab, as described herein, either prior to, or after the individual incurs remediable radiation damage from exposure to ionizing radiation.

According to another embodiment of the invention, there is provided a method of treating an individual for a proliferative disorder, particularly cancer, comprising:

(1) administering to the individual an effective amount of at least one radioprotective compound of formula $I^{ii}$ as described below; and (2) administering an effective amount of therapeutic ionizing radiation.

According to another embodiment of the invention, there is provided a method of treating an individual for a proliferative disorder, particularly cancer, comprising:

(1) administering to the individual administering an effective amount of at least one conjugate of the formula I-L-Ab or Ic-L-Ab as described herein; and (2) administering an effective amount of therapeutic ionizing radiation.

According to another embodiment of the invention, there is provided a method of reducing the number of malignant cells in the bone marrow of an individual, comprising (1) removing a portion of the individual's bone marrow, (2) administering an effective amount of at least one radioprotective compound of formula $I^{ii}$ as described below, to the removed bone marrow;

(3) irradiating the removed bone marrow with an effective amount of ionizing radiation; and (4) replacing the removed bone marrow with the treated bone marrow.

According to another embodiment of the invention, there is provided a method of reducing the number of malignant cells in the bone marrow of an individual, comprising (1) removing a portion of the individual's bone marrow, (2) administering an effective amount of at least one conjugate of the formula I-L-Ab or Ic-L-Ab, as described herein, to the removed bone marrow;

(3) irradiating the removed bone marrow with an effective amount of ionizing radiation; and (4) replacing the removed bone marrow with the treated bone marrow.

According to another embodiment of the invention, there is provided a method for protecting an individual from cytotoxic side effects of the administration of a cytotoxic agent, particularly a mitotic phase cell cycle inhibitor or a topoisomerase inhibitor, comprising administering to the individual, in advance of the administration of the cytotoxic agent, an effective amount of at least one cytoprotective compound of formula $I^{ii}$ as described below;

wherein the mitotic phase cell cycle inhibitor or topoisomerase inhibitor is not a compound of formula $I^{ii}$.

According to a sub-embodiment thereof, there is provided the above described method wherein the cytotoxic agent is a mitotic cell phase inhibitor, particularly selected from vinca alkaloids, taxanes, naturally occurring macrolides, colchicine and derivatives of colchicine.

More particularly, the mitotic cell phase inhibitor is selected from paclitaxel and Vincristine. Paclitaxel is an antimitotic drug presently used as an initial treatment for ovarian, breast and lung cancer, with moderate success. Vincrisitin is a well-established anti-mitotic drug widely used for the treatment of breast cancer, Hodgkin's lymphoma and childhood cancers.

According to another sub-embodiment thereof, there is provided the above described method wherein the cytotoxic agent is a topoisomerase, particularly selected from the group consisting of camptothecin, etoposide and mitoxanthrone.

According to another embodiment of the invention, there is provided a method of treating an individual for a proliferative disorder, particularly cancer, comprising:

(1) administering to the individual an effective amount of at least one cytoprotective compound of formula $I^{ii}$ as described below, and (2) administering an effective amount of at least one mitotic cell phase inhibitor or topoisomerase inhibitor after administration of the cytoprotective compound of formula $I^{ii}$.

According to another embodiment of the invention, there is provided a method of treating an individual for a proliferative disorder, particularly cancer, comprising:

(1) administering to the individual an effective amount of at least one conjugate of the formula I-L-Ab or Ic-L-Ab, as described herein, and (2) administering an effective amount of at least one mitotic cell phase inhibitor or topoisomerase inhibitor after administration of the cytoprotective compound of formula $I^{ii}$.

For the aforementioned therapeutic methods of treatment and methods of using radioprotective or cytoprotective compounds of the present invention, the administered compound is a compound according to formula $I^{ii}$, wherein:

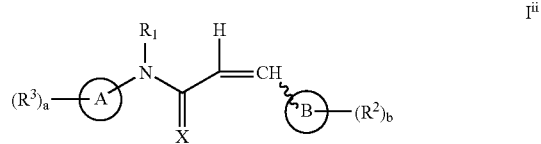

$I^{ii}$ wherein:

ring A and ring B are independently selected from the group consisting of aryl and heteroaryl;

X is O or S, preferably O;

$R^1$ is independently selected from the group consisting of —$R^4$, —$SO_2(C_1$-$C_6)$alkyl, —C(=O)$R^4$, —C(=O)O$R^4$, —C(=O)O($C_1$—$C_6$)alkylenearyl, —O$R^4$, —($C_2$-$C_6$)alkynyl, —($C_3$-$C_6$)heteroalkenyl, —($C_2$-$C_6$)alkylene-O$R^4$, substituted aryl, unsubstituted aryl, substituted heteroaryl, unsubstituted heteroaryl, substituted aryl($C_1$-$C_3$)alkyl, unsubstituted aryl($C_1$-$C_3$)alkyl, substituted heteroaryl($C_1$-$C_3$)alkyl and unsubstituted heteroaryl($C_1$-$C_3$)alkyl;

$R^2$ is independently selected from —($C_1$-$C_6$)alkyl; halogen; —O$R^4$; —C≡N; —$NO_2$; —$CO_2R^4$; —C(=O)$NR^4_2$; —C(=$NR^4$)$NR^4_2$; —O($C_1$-$C_3$)alkylene-$CO_2R^4$; —($C_1$-$C_6$)—O$R^4$; phosphonato; —$NR^4_2$; —NHC(=O)($C_1$-$C_6$)alkyl; sulfamyl; carbamyl; —OC(=O)($C_1$-$C_3$)alkyl, preferably —OC(=O)$CH_3$; —O($C_2$-$C_6$)—N(($C_1$-$C_6$)alkyl)$_2$, preferably —O($C_2$-$C_6$)—N($CH_3$)$_2$; —S($C_1$-$C_3$)alkyl; —S(=O)($C_1$-$C_3$)alkyl; —($C_1$-$C_3$)perfluoroalkyl; and —$SO_2$($C_1$-$C_3$)alkyl;

b is 1, 2, 3, 4 or 5; and

∿∿∿ indicates a single bond, whereby the compounds of formula I may be in either the E or the Z conformation;

$R^3$ is independently selected from halogen; —($C_1$-$C_6$)alkyl; —O$R^4$; —C≡N; —C(=O)$NR^4_2$; —C(=O)O$R^4$; —C(=$NR^4$)$NR^4_2$; —O($C_1$-$C_3$)alkylene-$CO_2R^4$; —($C_1$-$C_6$)—O$R^4$; nitro; phosphonato; —NHC(=O)($C_1$-$C_6$)alkyl; sulfamyl; carbamyl; —OC(=O)($C_1$-$C_3$)alkyl, preferably —OC(=O)$CH_3$; —O($C_2$-$C_6$)—N(($C_1$-$C_6$)alkyl)$_2$, preferably —O($C_2$-$C_6$)—N($CH_3$)$_2$; —($C_1$-$C_3$)perfluoroalkyl; and (i) or (ii) below:

(i)

-continued

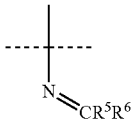
(ii)

wherein:

each M is a bivalent connecting group independently selected from the group consisting of —($C_1$-$C_6$)alkylene-, —$(CH_2)_d$—V—$(CH_2)_e$—, —$(CH_2)_f$—W—$(CH_2)_g$— and -Z-;

each y is independently selected from the group consisting of 0 and 1;

each V is independently selected from the group consisting of arylene, heteroarylene, —C(=O)—, —C(=O)($C_1$-$C_6$) perfluoroalkylene, —C(=O)—, —C(=S)—, —S(=O)—, —$SO_2$—, —C(=O)$NR^4$—, —C(=S)$NR^4$— and —$SO_2NR^4$—;

each W is independently selected from the group consisting of —$NR^4$—, —O— and —S—;

each d is independently selected from the group consisting of 0, 1 and 2, preferably from 0 and 1;

each e is independently selected from the group consisting of 0, 1 and 2, preferably from 0 and 1;

each f is independently selected from the group consisting of 1, 2 and 3, preferably from 1 and 2;

each g is independently selected from the group consisting of 0, 1 and 2, preferably from 0 and 1;

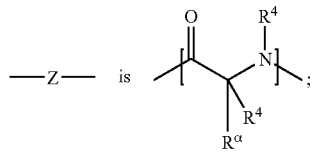

wherein the absolute stereochemistry of -Z- is S or R, or a mixture of S and R;

each $R^\alpha$ is independently selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl); and includes compounds wherein $R^\alpha$ and $R^4$ combine to form a 5-, 6- or 7-membered heterocyclic or carbocyclic ring;

a is 1, 2 or 3;

$R^4$ is independently selected from the group consisting of —H, —($C_1$-$C_6$)alkyl, substituted —($C_1$-$C_6$)alkyl, —($C_2$-$C_6$) alkenyl, substituted —($C_2$-$C_6$)alkenyl and heteroalkyl wherein two $R^4$ groups may together form a heterocycle;

each $R^5$ is independently selected from the group consisting of —$R^4$; unsubstituted aryl; substituted aryl; substituted heterocyclic; unsubstituted heterocyclic; —$CO_2R^4$; —C(=O)$NR^4_2$; —C(=NH)—$NR^4_2$; —($C_1$-$C_6$)perfluoroalkyl; —$CF_2$Cl; —P(=O)($OR^4$)$_2$; —OP(=O)($OR^4$)$_2$; —$CR^4R^7R^8$; and a monovalent peptidyl moiety with a molecular weight of less than 1000, preferably with a molecular weight of less than 800, more preferably with a molecular weight of less than 600, most preferably with a molecular weight of less than 400; provided that when y is 0 and $R^5$ is —$CO_2R^4$; then $R^4$ is not —H;

each $R^6$ is independently selected from the group consisting of —H, —($C_1$-$C_6$)alkyl, and aryl($C_1$-$C_3$)alkyl, each $R^7$ is independently selected from the group consisting of —H, —($C_1$-$C_6$)alkyl, —C(=O)$R^8$, —$OR^4$, —$SR^4$, —OC(=O)($CH_2$)$_2CO_2R^6$, guanidino, —$NR^4_2$, —$NR^4_3{}^+$, —$N^+(CH_2CH_2OR^5)_3$, halogen, phenyl, substituted phenyl, heterocyclyl, and substituted heterocyclyl; and each $R^8$ is independently selected from the group consisting of $R^\alpha$, halogen, —$NR^4_2$ and heterocycles containing two nitrogen atoms;

wherein the substituents for the substituted aryl and substituted heterocyclic groups comprising or included within Ar, $R^1$, $R^5$ $R^6$, $R^7$ and $R^\alpha$ are independently selected from the group consisting of halogen; —($C_1$-$C_6$)alkyl; —($C_1$-$C_6$)alkoxy; —$NO_2$; —C≡N; —C(=O)O($C_1$-$C_3$)alkyl; —$OR^4$; —($C_2$-$C_6$)—$OR^4$; phosphonato; —$NR^4_2$; —NHC(=O)($C_1$-$C_6$)alkyl; sulfamyl; carbamyl; —OC(=O)($C_1$-$C_3$)alkyl, preferably —OC(=O)$CH_3$; —O($C_2$-$C_6$)—N(($C_1$-$C_6$) alkyl)$_2$, preferably —O($C_2$-$C_6$)—N($CH_3$)$_2$; and —($C_1$-$C_3$) perfluoroalkyl; or a salt of such a compound.

For the aforementioned therapeutic methods of treatment and methods of using radioprotective or cytoprotective compounds of the present invention, the administered compound is a compound according to formula $I^{ii}$, wherein:

According to one preferred embodiment of a compound according to formula $I^{ii}$, -Z- is:

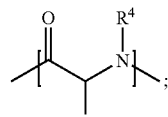

wherein the absolute stereochemistry of -Z- is either S or R; and each $R^\alpha$ is independently selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2CH_3$, —$CH_2$CH($CH_3$)$_2$, —$(CH_2)_4$—$NH_2$, —$(CH_2)_2$—S—$CH_3$, phenyl, —$CH_2$-phenyl, —$CH_2$—CH(OH)—$CH_3$, —$CH_2$-(3-indolyl), —$CH_2$-(4-hydroxyphenyl), —CH($CH_3$)$_2$ and —$CH_2CH_3$; and includes compounds wherein $R^\alpha$ and $R^4$ combine to form a 5-, 6- or 7-membered heterocyclic ring;

b is 1, 2 or 3;

each $R^7$ is independently selected from the group consisting of —H, —($C_1$-$C_6$)alkyl and —($C_1$-$C_6$)acyl;

each V is independently selected from the group consisting of —C(=O)—, —C(=S)—, —S(=O)—, —$SO_2$—, —C(=O)$NR^4$—, —C(=S)$NR^4$— and —$SO_2NR^4$—;

each $R^5$ is independently selected from the group consisting of —$R^4$, unsubstituted aryl, substituted aryl, substituted heterocyclic, unsubstituted heterocyclic, —$CO_2R^4$, —C(=O)$NR^4_2$, —C(=NH)—$NR^4_2$, and a monovalent peptidyl moiety with a molecular weight of less than 1000; provided that when y is 0 and $R^5$ is —$CO_2R^4$; then $R^4$ is not —H; and wherein the substituents for the substituted aryl and substituted heterocyclic groups comprising or included within Ar, $R^1$, $R^5$ and $R^\alpha$ are independently selected from the group consisting of halogen, —($C_1$-$C_6$)alkyl, —($C_1$-$C_6$)alkoxy, —$NO_2$, —C≡N, —C(=O)O($C_1$-$C_3$)alkyl, —$OR^4$, —($C_2$-$C_6$)—$OR^4$, phosphonato, —$NR^4_2$, —NHC(=O)($C_1$-$C_6$)

alkyl, sulfamyl, carbamyl, —OC(=O)($C_1$-$C_3$)alkyl, —O($C_2$-$C_6$)—N(($C_1$-$C_6$)alkyl)$_2$ and —($C_1$-$C_3$)perfluoroalkyl; or a salt of such a compound.

The propene amides of the invention are characterized by isomerism resulting from the presence of an olefinic double bond. This isomerism is commonly referred to as cis-trans isomerism, but the more comprehensive naming convention employs E and Z designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, NY, 4$^{th}$ ed., 1992, p. 127-138, the entire contents of which is incorporated herein by reference. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher ranking groups are on opposite sides of the double bond, is designated E (for the German word "entgegen", which means "opposite"). Both E and Z conformations are included in the scope of the compounds of the present invention. The E conformation is preferred.

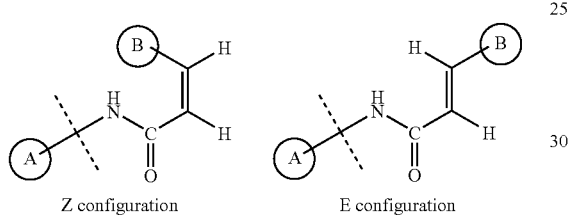

Z configuration       E configuration

The preferred compounds of the present invention have a particular spatial arrangement of substituents on the aromatic rings, which is related to the structure activity relationship demonstrated by the compound class. Often such substitution arrangement is denoted by a numbering system, however numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

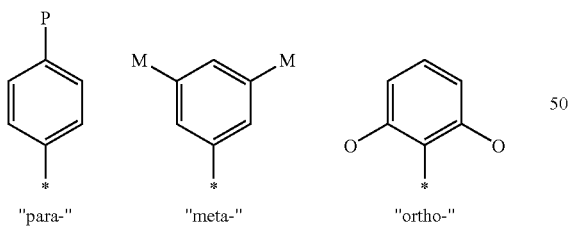

"para-"      "meta-"      "ortho-"

Since aromatic rings are essentially planar, these designations essentially define geometric positions on a six-membered ring that could be communicated geometrically, i.e., the ortho substituent forms a planar angle of 60° with the substituent to which it is being referenced. Likewise, a meta substituent defines a 120° planar angle and a para substituent defines a 180° angle.

To designate substituent patterns in a general way for any planar ring system, the ortho-meta-para nomenclature is only descriptive for six-membered monocycles, i.e., there is no "para" substituent on a five-membered aromatic ring or a bicyclic ring. However, definition of a planar angle or a range of planar angles between two substituents is a convention which will readily communicate a particular substitution pattern that is independent of the particular ring involved. Thus, a para substituent in a six-membered aromatic ring is closely approximated in other planar mono- or bicyclic rings by any substituent which, with the reference substituent forms a planar angle of between about 144° and about 180°. Likewise, a meta substituent in a six-membered aromatic ring is approximated in other planar mono- or bicyclic rings by any substituent which, with the reference substituent forms a planar angle of between about 90° and about 144°. Several examples of substituent patterns which could be communicated in this way are depicted below.

(a)

(b)

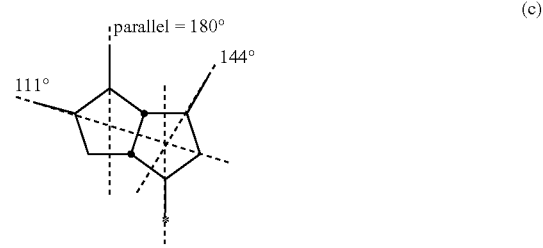

(c)

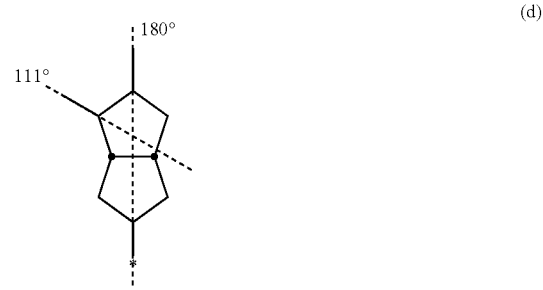

(d)

(e)

-continued (f)
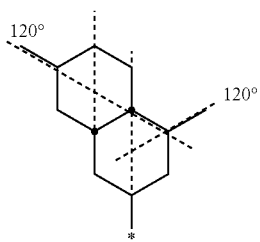

(g)
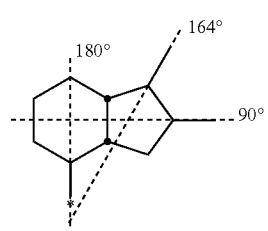

(h)
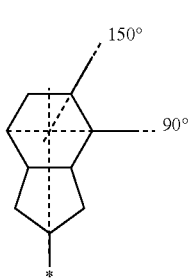

In some instances, for example, a naphthalene system substituted at the 1- and 5-positions as shown in the (e) structure above, a true angle is not formed because there is no geometric intersection between the lines defined by the 1- and 5-position bonds. However, it is reasonable to regard these "parallel" bonds as defining a 180° angle and thus approximating the para-arrangement of a six-membered planar ring.

The term "acyl" means a radical of the general formula —C(=O)—R, wherein —R is hydrogen, hydrocarbyl, amino or alkoxy. "Examples include for example, acetyl (—C(=O)CH$_3$), propionyl (—C(=O)CH$_2$CH$_3$), benzoyl (—C(=O)C$_6$H$_5$). Phenylacetyl (—C(=O)CH$_2$C$_6$H$_5$), carboethoxy (—CO$_2$Et), and dimethylcarbamoyl (—C(=O)N(CH$_3$)$_2$).

The term "alkyl", by itself or as part of another substituent means, unless otherwise stated, a straight, branched or cyclic chain hydrocarbon radical, including di- and multi-radicals, having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

The term "alkenyl" employed alone or in combination with other terms, means, unless otherwise stated, a stable monounsaturated or di-unsaturated hydrocarbon radical straight chain, branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by —CH=CH—CH$_2$—.

Substituted alkyl or alkenyl means alkyl or alkenyl, as defined above, substituted by one, two or three substituents selected from the group consisting of halogen, —OH, —NH$_2$, —N(CH$_3$)$_2$, —CO$_2$H, —CO$_2$($C_1$-$C_4$)alkyl, —CF$_3$, —CONH$_2$, —SO$_2$NH$_2$, —C(=NH)NH$_2$, —CN and —NO$_2$, preferably containing one or two substituents selected from halogen, —OH, NH$_2$, —N(CH$_3$)$_2$, trifluoromethyl and —CO$_2$H, more preferably selected from halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle. Examples of amino groups include: —NH$_2$, methyl amino, diethyl amino, anilino, benzyl amino, piperidinyl, piperazinyl and indolinyl.

The term "carbamyl" means the group —C(=O)NRR', wherein R and R' are independently selected from hydrogen or a hydrocarbyl radical, or wherein R and R' combined form a heterocycle. Examples of carbamyl groups include: —C(=O)NH$_2$ and —C(=O)N(CH$_3$)$_2$.

The term "carboxy($C_1$-$C_3$)alkoxy" means a radical in which the carboxy group —COOH is attached to a carbon of a straight or branched chain alkoxy group containing one to three carbon atoms. The radical thus contains up to four carbon atoms. Examples include: —O(CH$_2$)$_3$CO$_2$H and —O(CH$_2$)$_2$CO$_2$H.

The term "cycloalkyl" refers to ring-containing alkyl radicals. Examples include cyclohexyl, cyclopentyl, cyclopropyl methyl and norbornyl The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S('O)—CH$_3$. Up to two heteroatoms may be consecutive, such as, for example, —CH$_2$—NH—OCH$_3$, or —CH$_2$—CH$_2$—S—S—CH$_3$.

The term "heteroalkenyl" by itself or in combination with another term means, unless otherwise stated, a stable straight or branched chain monounsaturated or di-unsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—

CH=N—OCH$_3$, —CH=CH—N(CH$_3$)—CH$_3$, and —CH$_2$—CH=CH—CH$_2$—SH.

The term "hydroxyalkyl" means an alkyl radical wherein one or more of the carbon atoms is substituted with hydroxy. Examples include —CH$_2$CH(OH)CH$_3$ and —CH$_2$CH$_2$OH.

The terms "halo" or "halogen" by themselves or as part of another substituent mean, unless otherwise stated, a fluorine, chlorine, bromine, or iodine atom, preferably, fluorine, chlorine, or bromine, more preferably, fluorine or chlorine.

The term "di(C$_1$-C$_6$)alkylamino(C$_2$-C$_6$)alkoxy" or "—O (C$_2$-C$_6$)—N((C$_1$-C$_6$)alkyl)$_2$, means (alkyl)$_2$N(CH$_2$)$_z$O— wherein the two alkyl chains connected to the nitrogen atom independently contain from one to six carbon atoms, preferably from one to three carbon atoms, and z is an integer from 2 to 6. Preferably, z is 2 or 3. Most preferably, z is 2, and the alkyl groups are methyl, that is, the group is the dimethylaminoethoxy group, (CH$_3$)$_2$NCH$_2$CH$_2$O—.

The term "(C$_x$-C$_y$)perfluoroalkyl," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$.

The term "phosphonato" means the group —PO(OH)$_2$.

The term "sulfamyl" means the group —SO$_2$NRR', wherein R and R' are independently selected from hydrogen or a hydrocarbyl radical, or wherein R and R' combined form a heterocycle. Examples of sulfamyl groups include: —SO$_2$NH$_2$, —SO$_2$N(CH$_3$)$_2$ and —SO$_2$NH(C$_6$H$_5$). Preferred are —SO$_2$NH$_2$, SO$_2$N(CH$_3$)$_2$ and —SO$_2$NHCH$_3$.

The term "aromatic" refers to a carbocycle or heterocycle having one or more polyunsaturated rings having aromatic character (4n+2) delocalized π (pi) electrons.

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "aryl-(C$_1$-C$_3$)alkyl" means a radical wherein a one to three carbon alkylene chain is attached to an aryl group, e.g., —CH$_2$CH$_2$-phenyl. Preferred is aryl(CH$_2$)— and aryl (CH(CH$_3$))—. The term "substituted aryl-(C$_1$-C$_3$)alkyl" means an aryl-(C$_1$-C$_3$)alkyl radical in which the aryl group is substituted. Preferred is substituted aryl(CH$_2$)—. Similarly, the term "heteroaryl(C$_1$-C$_3$)alkyl" means a radical wherein a one to three carbon alkylene chain is attached to a heteroaryl group, e.g., —CH$_2$CH$_2$-pyridyl. Preferred is heteroaryl (CH$_2$)—. The term "substituted heteroaryl-(C$_1$-C$_3$)alkyl" means a heteroaryl-(C$_1$-C$_3$)alkyl radical in which the heteroaryl group is substituted. Preferred is substituted heteroaryl(CH$_2$)—.

The term "arylene," by itself or as part of another substituent means, unless otherwise stated, a divalent aryl radical. Preferred are divalent phenyl radicals, particularly 1,4-divalent phenyl radicals.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A polycyclic heteroaryl may include one or more rings which are partially saturated. Examples include tetrahydroquinoline and 2,3-dihydrobenzofuryl. For compounds of formula I, the attachment point on ring A or ring B is understood to be on an atom which is part of an aromatic monocyclic ring or a ring component of a polycyclic aromatic which is itself an aromatic ring.

Examples of non-aromatic heterocycles include monocyclic groups such as: Aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-traizolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: Indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofiryl, 1,2-benzisoxazolyl, benzothienyl, particularly 3-, 4-, 5-, 6- and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

The term "heteroarylene," by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from pyridine, piperazine, pyrimidine, pyrazine, furan, thiophene, pyrrole, thiazole, imidazole and oxazole.

For compounds of the present invention, when an aromatic or heteroaromatic ring is attached to a position and the ring comprises a polycyclic ring which is partially saturated, the attachment point on the aromatic or heteroaromatic ring is on a ring atom of an aromatic ring component of the polycyclic ring. For example on the partially saturated heteroaromatic ring, 1,2,3,4-tetrahydroisoquinoline, attachment points would be ring atoms at the 5-, 6-, 7- and 8-positions.

The aforementioned listing of heterocyclyl and heteroaryl moieties is intended to be representative, not limiting.

The term "hydrocarbyl" refers to any moiety comprising only hydrogen and carbon atoms. Preferred heteroaryl groups are (C$_1$-C$_{12}$)hydrocarbyl, more preferred are (C$_1$-C$_7$)hydrocarbyl, most preferred are benzyl and (C$_1$-C$_6$)alkyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

Where a substituent is an alkyl or alkoxy group, the carbon chain may be branched, straight or cyclic, with straight being preferred.

The term "antibody" is intended to encompass not only intact antigen-binding immunoglobulin molecules, but also to include antigen-binding fragments thereof such as Fab, Fab' and F(ab')$_2$ fragments, or any other fragment retaining the antigen-binding ability of an intact antibody.

The term "humanized antibody" refers to an antibody that has its complementary determining regions (CDR's) derived from a non-human species immunoglobulin, and the remainder of the antibody molecule derived from a human immunoglobulin.

The term "chimeric antibody" means an antibody comprising a variable region and a constant region derived from different species.

The term "humanized chimeric antibody" is means a chimeric antibody in which at least the constant region is human-derived.

The term "monospecific polyclonal antibody" means an antibody preparation comprising multiple antibody species having specificity for a single antigen.

The term "monovalent peptidyl moiety" refers to a peptide radical as a substituent on a molecule of formula I. Such a radical has a chemical structure that varies from the structure of the corresponding peptide in that the structural component of the peptide, i.e., an alpha amino group, a sidechain amino group, an alpha carboxyl group or a sidechain carboxyl group, will form a different functionality when bonded to the molecule of which it is to be a substituent. For example, for a peptide as shown below

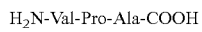

H$_2$N-Val-Pro-Ala-COOH which is a substituent on a compound of formula I, the peptide is coupled to the compound of formula I such that a carboxyl moiety of said peptide is coupled to a free amine moiety on the formula I compound. Elimination of H$_2$O results in the formation of an amide bond. As a practical result, the corresponding monovalent peptidyl substituent is shown to the left of the dotted line in the depiction below of the aforementioned peptide bonded to a compound of formula I:

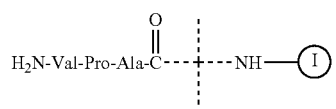

The monovalent peptide moiety may be attached via either an alpha- or a sidechain amino group, or an alpha or sidechain carboxyl group. The attachment point on the peptide moiety will depend on the functionality at the terminus of the bivalent tether group M in a manner that is known to one of skill in the art (see the definition.

Specifically, the peptidyl moiety may be coupled to the M bivalent tether via an alpha amino or a side chain amino group when the M tether terminates in:

—C(=O)—, —C(=S)—, —S(=O)—, or SO$_2$, i.e., when the variable e is zero.

Likewise, the peptidyl moiety may be coupled to the M bivalent tether via an alpha carboxy or a side chain carboxy group when the M tether terminates in:

—C(=O)NR$^5$—, —SO$_2$NR$^5$—, —NR$^5$—, —S— or —O—, i.e., when the variable e (or g) is zero.

The term "effective amount" when used to describe therapy to a patient suffering from a proliferative disorder, refers to the amount of a compound of formula I that inhibits the growth of tumor cells or alternatively induces apoptosis of cancer cells, preferably tumor cells, resulting in a therapeutically useful and selective cytotoxic effect on proliferative cells when administered to a patient suffering from a cancer or other disorder which manifests abnormal cellular proliferation.

As used herein, "ionizing radiation" is radiation of sufficient energy that, when absorbed by cells and tissues, induces formation of reactive oxygen species and DNA damage. This type of radiation includes X-rays, gamma rays, and particle bombardment (e.g., neutron beam, electron beam, protons, mesons and others), and is used for medical testing and treatment, scientific purposes, industrial testing, manufacturing and sterilization, weapons and weapons development, and many other uses. Radiation is typically measured in units of absorbed dose, such as the rad or gray (Gy), or in units of dose equivalence, such as the rem or sievert (Sv). The relationship between these units is given below:

| rad and gray (Gy) | rem and sievert (Sv) |
| --- | --- |
| 1 rad = 0.01 Gy | 1 rem = 0.01 Sv |

The Sv is the Gy dosage multiplied by a factor that includes tissue damage done. For example, penetrating ionizing radiation (e.g., gamma and beta radiation) have a factor of about 1, so 1 Sv=~1 Gy. Alpha rays have a factor of 20, so 1 Gy of alpha radiation=20 Sv.

By "effective amount of ionizing radiation" is meant an amount of ionizing radiation effective in killing, or reducing the proliferation, of abnormally proliferating cells in a subject. As used with respect to bone marrow purging, "effective amount of ionizing radiation" means an amount of ionizing radiation effective in killing, or in reducing the proliferation, of malignant cells in a bone marrow sample removed from a subject.

By "acute exposure to ionizing radiation" or "acute dose of ionizing radiation" is meant a dose of ionizing radiation absorbed by a subject in less than 24 hours. The acute dose may be localized, as in radiotherapy techniques, or may be absorbed by the subject's entire body. Acute doses are typically above 10,000 millirem (0.1 Gy), but may be lower.

By "chronic exposure to ionizing radiation" or "chronic dose of ionizing radiation" is meant a dose of ionizing radiation absorbed by a subject over a period greater than 24 hours. The dose may be intermittent or continuous, and may be localized or absorbed by the subject's entire body. Chronic doses are typically less than 10,000 millirem (0.1 Gy), but may be higher.

By "effective amount of a radioprotective compound" is meant an amount of compound effective to reduce or eliminate the toxicity associated with radiation in normal cells of the subject, and also to impart a direct cytotoxic effect to abnormally proliferating cells in the subject. As used with respect to bone marrow purging, "effective amount of the radioprotective N-aryl (or N-heteroaryl) propene amide compound" means an amount of compound effective to reduce or eliminate the toxicity associated with radiation in bone marrow removed from a subject, and also to impart a direct cytotoxic effect to malignant cells in the bone marrow removed from the subject.

By "at risk of incurring exposure to ionizing radiation" is meant that a subject may advertently (such as by scheduled radiotherapy sessions) or inadvertently be exposed to ionizing radiation in the future. Inadvertent exposure includes accidental or unplanned environmental or occupational exposure.

By "effective amount" of the mitotic phase cell cycle inhibitor or topoisomerase inhibitor is meant an amount of said inhibitor effective in killing or reducing the proliferation of cancer cells in a host animal.

By "effective amount" of the cytoprotective compound is meant an amount of compound effective to reduce the toxicity of the mitotic phase cell cycle inhibitor or topoisomerase inhibitor on normal cells of the animal.

The term "cell cycle" refers to the usual description of cell development in terms of a cycle consisting of a series of phases—interphase and M (mitotic) phase—and the subdivision of interphase into the times when DNA synthesis is proceeding, known as the S-phase (for synthesis phase), and the gaps that separate the S-phase from mitosis. G1 is the gap after mitosis but before DNA synthesis starts, and G2 is the gap after DNA synthesis is complete before mitosis and cell division. Interphase is thus composed of successive G1, s and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

By "mitotic phase cell cycle inhibitor" is meant a chemical agent whose mechanism of action includes inhibition of a cell's passage through any portion of the mitotic (M) phase of the cell cycle. Such agents include, by way of example and not limitation, taxanes, such as paclitaxel and its analogs; vinca alkaloids such as vincristine and vinblastine; colchicine and its derivatives; and naturally occurring macrolides such as rhizoxin, maytansine, ansamitocin P-3, phomopsin A, dolastatin 10 and halichrondin B.

By "topoisomerase inhibitor" is meant a chemical agent whose mechanism of action includes interfering with the function of a topoisomerase.

The topoisomerases constitute a group of enzymes that catalyze the conversion of DNA from one topological form to another by introducing transient breaks in one or both strands of a DNA duplex. Topological isomers are molecules that differ only in their state of supercoiling. Type I topoisomerase cuts one strand of DNA and relaxes negatively supercoiled DNA, but does not act on positively supercoiled DNA. Type II topoisomerase cuts both strands of DNA and increases the degree of negative supercoiling in DNA.

Thus topoisomerase inhibitors are subdivided into inhibitors of topoisomerase I and inhibitors of topoisomerase II. Inhibitors of topoisomerase I include, for example, adriamycin and etoposide. Inhibitors of topoisomerase II include, for example, camptothecin, irinotecan and topotecan.

The term "individual" or "subject", includes human beings and non-human animals. With respect to the disclosed radioprotective and cytoprotective methods, these terms refer, unless the context indicates otherwise, to an organism that is scheduled to incur, or is at risk for incurring, or has incurred, exposure to ionizing radiation or exposure to one or more cytotoxic chemotherapeutic agents.

DETAILED DESCRIPTION OF THE INVENTION

According to the present invention, aryl and heteroaryl propene amides and salts thereof are believed to selectively inhibit proliferation of cancer cells, and kill various tumor cell types without killing (or with reduced killing of) normal cells. Cells are killed at concentrations where normal cells may be temporarily growth-arrested but not killed.

The compounds of the invention are believed to inhibit the proliferation of tumor cells, and for some compounds, induce cell death. Cell death results from the induction of apoptosis. The compounds are believed effective against a broad range of tumor types, including but not limited to the following: ovarian cancer, breast cancer, prostate cancer, lung cancer, renal cancer, colorectal cancer, brain cancer and leukemia.

The compounds are also believed useful in the treatment of non-cancer proliferative disorders, including but not limited to the following: hemangiomatosis in newborn, secondary progressive multiple sclerosis, chronic progressive myelodegenerative disease, neurofibromatosis, ganglioneuromatosis, keloid formation, Pagets Disease of the bone, fibrocystic disease of the breast, uterine fibroids, Peyronie's fibrosis, Dupuytren's fibrosis, restenosis and cirrhosis.

The compounds of the invention are also believed to protect normal cells and tissues from the effects of acute and chronic exposure to ionizing radiation.

Subjects may be exposed to ionizing radiation when undergoing therapeutic irradiation for the treatment of the above proliferative disorders. The compounds are believed effective in protecting normal cells during therapeutic irradiation of abnormal tissues. The compounds are also believed useful in protecting normal cells during radiation treatment for leukemia, especially in the purging of malignant cells from autologous bone marrow grafts with ionizing radiation.

According to the invention, therapeutic ionizing radiation may be administered to a subject on any schedule and in any dose consistent with the prescribed course of treatment, as long as the radioprotectant compound of the invention is administered prior to the radiation. The course of treatment differs from subject to subject, and those of ordinary skill in the art can readily determine the appropriate dose and schedule of therapeutic radiation in a given clinical situation.

In addition, the compounds of the present invention are believed to protect normal cells and tissues from the effects of exposure to cytotoxic agents such as for example, mitotic phase cell cycle inhibitors and topoisomerase inhibitors.

The compounds of the present invention differ from other known cytoprotective agents in that they not only protect normal cells, but are also operationally cytotoxic in tumor cells. In normal cell, the cytoprotective compounds of the invention induce a reversible resting state rendering the normal cells relatively refractory to the cytotoxic effect of mitotic phase cell cycle inhibitors and topoisomerase inhibitors.

Normal human fibroblasts exposed to compounds of the invention in vitro are believed to exhibit transiently reduced replication rates. When the same cells are then exposed to a mitotic phase cell cycle inhibitor such as paclitaxel, the cells are believed to be protected from the toxic effects of the inhibitor. The precise cytoprotective mechanism of action of the aryl and heteroaryl propene amides on normal tissues is unknown. However, based on experimental models, and without wishing to be bound by any theory, these compounds may affect several elements in normal cells inducing a reversible quiescent cell-cycling state in which transit through mitosis, and many of the changes necessary for such passage, are down regulated, inactivated or absent. Tumor cells appear to be refractory to this effect of the compounds and in fact continue cycling with readily activated programmed cell death pathways. According to other possible mechanisms of protection, anticancer agent-induced proinflammatory cytokine release from monocytes or macrophages, activation of JNK-1 death pathway induction, and P34Cdc2 kinase may be rendered innocuous by pre-exposure to compounds of the invention.

In one embodiment of the invention, there is provided a compound according to formula Ib:

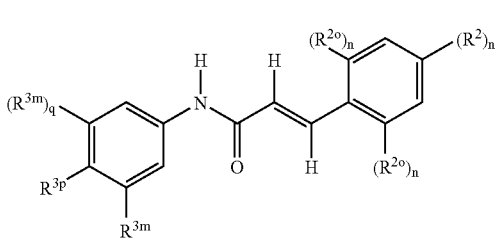

wherein:
$R^1$ is —H;
X is O;
q is 0;
n is 0 or 1, and
the conformation of the olefin double bond is E; and
wherein $R^2$, $R^{2o}$, $R^{3m}$, and $R^{3p}$ are as defined for formula I above.

In a further sub-embodiment of the above described compounds, there is provided a compound, wherein:
$R^{2o}$ is —($C_1$-$C_6$)alkoxy;
$R^2$ is selected from the group consisting of halogen, —($C_1$-$C_6$)alkyl, —($C_1$-$C_6$)alkoxy and —$NR^4_2$; and
n is 0 or 1;
or a salt of such a compound.

In another embodiment of the invention there is provided a compound of formula Ic:

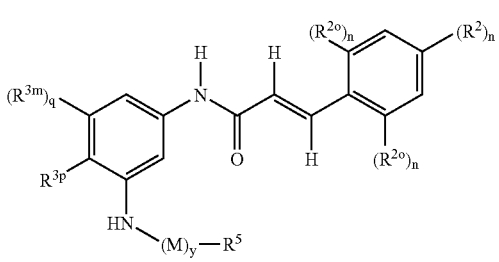

wherein:
$R^2$, $R^{2o}$, $R^{3m}$, $R^{3p}$ and n, M, y and $R^6$ are as defined as for formula I above; or a salt of such a compound.

In a sub-embodiment of the compounds of the invention, there is provided a compound of formula Ic, wherein:
q is 0;
n is 1;
$R^3$, is halogen or —($C_1$-$C_6$)alkoxy;
$R^{2o}$ is —($C_1$-$C_6$)alkoxy; and
$R^2$ is —($C_1$-$C_6$)alkoxy;
or a salt of such a compound.

In a further sub-embodiment of the compounds of the invention, there is provided a compound of formula Ic, wherein:
q is 0;
n is 1;
$R^3$l is halogen or methoxy;
$R^{2o}$ is methoxy; and
$R^2$ is methoxy;
or a salt of such a compound.

Such compounds include, for example, (E)-N-(4-methoxy-3-aminophenyl)-3-(2,4,6-trimethoxyphenyl)-2-propenamide, and salts thereof.

The amino group of amino-substituted aryl and heteroaryl propene amides such as, for example, (E)-N-(4-methoxy-3-aminophenyl)-3-(2,4,6-trimethoxyphenyl)-2-propen-amide may be derivatized in several ways to form additional compounds of the invention.

Such compounds of the invention include, for example:
2-[({5-[(2E)-3-(2,4,6-trimethoxyphenyl)prop-2-enoylamino]-2-methoxyphenyl}amino)sulfonyl]acetic acid;
2-(N-{5-[(2E)-3-(2,4,6-trimethoxyphenyl)prop-2-enoylamino]-2-methoxyphenyl}carbamoyl)acetic acid;
(2E)-N-[3-(amidinoamino)-4-methoxyphenyl]-3-(2,4,6-trimethoxyphenyl)prop-2-enamide;
2-({5-[(2E)-3-(2,4,6-trimethoxyphenyl)prop-2-enoylamino]-2-methoxyphenyl}amino)acetic acid;
(2E)-N-{3-[(3,5-dinitrophenyl)carbonylamino]-4-methoxyphenyl}-3-(2,4,6-trimethoxyphenyl)prop-2-enamide;
(2E)-N-{3-[(3,5-diaminophenyl)carbonylamino]-4-methoxyphenyl}-3-(2,4,6-trimethoxyphenyl)prop-2-enamide;
(2E)-N-[$3$-(2-chloroacetylamino)-4-methoxyphenyl]-3-(2,4,6-trimethoxyphenyl)prop-2-enamide;
(2E)-N-{4-methoxy-3-[2-(4-methylpiperazinyl)acetylamino]-phenyl)-3-(2,4,6-trimethoxyphenyl)prop-2-enamide;
(2E)-N-[4-methoxy-3-(phenylcarbonylamino)phenyl]-3-(2,4,6-trimethoxyphenyl)prop-2-enamide;
(2E)-N-{4-methoxy-3-[(4-nitrophenyl)carbonylamino]phenyl}-3-(2,4,6-trimethoxyphenyl)prop-2-enamide;
(2E)-N-{3-[(4-aminophenyl)carbonylamino]-4-methoxyphenyl}-3-(2,4,6-trimethoxyphenyl)prop-2-enamide;
(2E)-N-{3-[(1Z)-1-aza-2-(4-nitrophenyl)vinyl]4-methoxyphenyl}-3-(2,4,6-trimethoxyphenyl)prop-2-enamide;
(2E)-N-[3- ((2R)-2,6-diaminohexanoylamino)-4-methoxyphenyl]-3-(2,4,6-trimethoxyphenyl)prop-2-enamide;
(2E)-N-[3-((2R)-2-amino-3-hydroxypropanoylamino)-4-methoxyphenyl]-3-(2,4,6-trimethoxyphenyl)prop-2-enamide;
(2E)-N-[3-((2S)-2-amino-3-hydroxypropanoylamino)-4-methoxyphenyl]-3-(2,4,6-trimethoxyphenyl)prop-2-enamide;
(2E)-N-[3- (aminocarbonylamino)-4-methoxyphenyl]-3-(2,4,6-trimethoxyphenyl)prop-2-enamide;
(2E)-N-[4-methoxy-3-(methylamino)phenyl]-3-(2,4,6-trimethoxyphenyl)prop-2-enamide;

(2E)-N-[3-(acetylamino)-4-methoxyphenyl]-3-(2,4,6-tri-methoxyphenyl)prop-2-enamide;
(2E)-N-(3-{[(2,4-dinitrophenyl)sulfonyl]amino}-4-methoxyphenyl)-3-(2,4,6-trimethoxyphenyl)prop-2-enamide;
(2E)-N-(3-{[(2,4-diaminophenyl)sulfonyl]amino}-4-methoxyphenyl)-3-(2,4,6-trimethoxyphenyl)prop-2-enamide;
(2E)-N-{3-[2-(dimethylamino)acetylamino]-4-methoxyphenyl}-3-(2,4,6-trimethoxyphenyl)prop-2-enamide;
2-({5-[(2E)-3-(2,4,6-trimethoxyphenyl)prop-2-enoylamino]-2-methoxyphenyl}amino)propanoic acid;
(2E)-N-(4-methoxy-3-{[4-(4-methylpiperazinyl)phenyl]-carbonylamino}phenyl)-3-(2,4,6-trimethoxyphenyl)prop-2-enamide;
(2E)-N-[3-(2-hydroxyacetylamino)-4-methoxyphenyl]-3-(2,4,6-trimethoxyphenyl)prop-2-enamide;
(2E)-N-[4-methoxy-3-(2-pyridylacetylamino)phenyl]-3-(2,4,6-trimethoxyphenyl)prop-2-enamide;
(N-{5-[(2E)-3-(2,4,6-trimethoxyphenyl)prop-2-enoylamino]-2-methoxyphenyl}carbamoyl)methyl acetate;
(2E)-N-[3-(2-hydroxypropanoylamino)-4-methoxyphenyl]-3-(2,4,6-trimethoxyphenyl)prop-2-enamide;
(2E)-N-{4-methoxy-3-[2-(triethylammonium)acetylamino]-phenyl}-3- (2,4,6-trimethoxyphenyl)-prop-2-enamide;
(2E)-N-(4-methoxy-3-{2-[tris(2-hydroxyethyl)ammonium]-acetyl-amino}phenyl)-3-(2,4,6-trimethoxyphenyl)prop-2-enamide;
(2E)-N-[3-(2-hydroxy-2-methylpropanoylamino)-4-methoxyphenyl]-3-(2,4,6-trimethoxyphenyl)prop-2-enamide;
1-(N-{5-[(2E)-3-(2,4,6-trimethoxyphenyl)prop-2-enoylamino]-2-methoxyphenyl}carbamoyl)-isopropyl acetate;
(2E)-N-[4-methoxy-3-(2,2,2-trifluoroacetylamino)phenyl]-3-(2,4,6-trimethoxyphenyl)prop-2-enamide;
(2E)-N-(4-methoxy-3-{[(trifluoromethyl)sulfonyl]-amino}phenyl)-3-(2,4,6-trimethoxyphenyl)prop-2-enamide;
3-(N-{5-[(2E)-3-(2,4,6-trimethoxyphenyl)prop-2-enoylamino]-2-methoxyphenyl}carbamoyl)propanoic acid;
3-(N-{5-[(2E)-3-(2,4,6-trimethoxyphenyl)prop-2-enoylamino]-2-methoxyphenyl}carbamoyl)propanoyl chloride;
3-{[(N-{5-[(2E)-3-(2,4,6-trimethoxyphenyl)prop-2-enoylamino]-2-methoxyphenyl}carbamoyl)methyl]oxycarbonyl}propanoic acid;
4-(N-{5-[(2E)-3-(2,4,6-trirethoxyphenyl)prop-2-enoylamino]-2-methoxyphenyl}carbamoyl)butanoic acid;
(2E)-N-{4-methoxy-3-[2-(phosphonooxy)acetylamino]phenyl}-3-(2,4,6-trimethoxyphenyl)prop-2-enamide, disodium salt;
4-({5-[(2E)-3-(2,4,6-tiimethoxyphenyl)prop-2-enoylamino]-2-methoxyphenyl}amino)butanoic acid;
3-({5-[(2E)-3-(2,4,6-trimethoxyphenyl)prop-2-enoylamino]-2-methoxyphenyl}amino)propanoic acid;
(2E)-N-[4-methoxy-3-(methoxycarbonylamino)phenyl]-3-(2,4,6-trimethoxyphenyl)prop-2-enamide,
(2E)-N-(4-methoxy-3-{[(4-methoxyphenyl)sulfonyl]amino}-phenyl)-3-(2,4,6-trimethoxyphenyl)prop-2-enamide;
(N-{5-[(2E)-3- (2,4,6-trimethoxyphenyl)prop-2-enoylamino]-2-methoxyphenyl}carbamoyl)ethyl acetate;
methyl 3-(N-{5-[(2E)-3-(2,4,6-trimethoxyphenyl)prop-2-enoylamino]-2-methoxyphenyl}carbamoyl)propanoate;
ethyl 2-(N-{5-[(2E)-3-(2,4,6-trimethoxyphenyl)prop-2-enoylamino]-2-methoxyphenyl}carbamoyl)acetate;
(2E)-N-[4-methoxy-3-(2,2,3,3,3-pentafluoropropanoylamino)-phenyl]-3-(2,4,6-trimethoxyphenyl)prop-2-enamide;
methyl 2-(N-{5-[(2E)-3-(2,4,6-trimethoxyphenyl)prop-2-enoyl-amino]-2-methoxyphenyl}carbamoyl)-2,2-difluoroacetate;
3-(N-{5-[(2E)-3-(2,4,6-trimethoxyphenyl)prop-2-enoylamino]-2-methoxyphenyl}carbamoyl)-2,2,3,3-tetrafluoropropanoic acid;
(2E)-N-[3-(2-aminoacetylamino)-4-methoxyphenyl]-3-(2,4,6-trimethoxyphenyl)prop-2-enamide;
2-(N-{5-[(2E)-3-(2,4,6-trimethoxyphenyl)prop-2-enoylamino]-2-methoxyphenyl}carbamoyl)-2,2-difluoroacetic acid;
(2E)-N-{3-[2-(dimethylamino)-2,2-difluoroacetylamino]-4-methoxy-phenyl}-3-(2,4,6-trimethoxyphenyl)prop-2-enamide; and salts of such compounds.

The general synthesis scheme may be used in two different synthesis strategies to produce compounds derivatized at the aromatic amino group.

The compounds of the invention may be prepared by one of several methods. In the synthesis methods to follow, reference to "Ar" and to the term "aryl" is intended to include substituted and unsubstituted aryl, and also substituted and unsubstituted heteroaryl.

According to General Procedure 1, aryl propene amides are prepared by a novel synthesis, which is depicted in Scheme 1. By this synthetic route, the aryl propene amide, I is assembled via the condensation of an intermediate aromatic malonamide acid IV with an aromatic aldehyde V.

The intermediate aromatic malonamide acid IV is prepared by hydrolysis of the corresponding aromatic malonamide ester III. This hydrolysis is typically performed at elevated temperature in using at least one equivalent of a strong base such as, for example sodium hydroxide or lithium hydroxide. The latter reaction is conducted in a mixed aqueous and organic solvent, the organic solvent being selected from water miscible solvents such as, for example, methanol, ethanol or THF. The intermediate aromatic malonamide ester III is prepared by coupling an aromatic amine H with an alkylmalonyl halide. Several of these alkyl malonyl halide reagents are available commercially, including, for example, ethyl-3-chloro-3-oxoprionate (commonly called ethyl malonyl chloride)[36239-09-5) and methyl 3-chloro-3-oxoproprionate (commonly called methyl malonyl chloride)[37517-81-01 (both available from Aldrich Chemicals). In addition these malonyl chlorides may be synthesized using known methods.

General Procedure 1

Step A: Synthesis of an Alkyl-2(N-Arylaminocarbonyl)acetate

According to Scheme 1, to a solution of an aromatic amine II (10 mmol) and TEA (10 mmol) in dichloromethane(DCM) (50 mL) at room temperature is slowly added a solution of an alkyl malonyl chloride (10 mmol) in dichloromethane. The reaction is stirred for 1 hour. The reaction mixture is filtered and solvent is removed under reduced pressure to yield an oily material.

The crude product is purified by column chromatography to yield an alkyl-2-(N-arylaminocarbonyl)-acetate III.

Step B: Synthesis of 3-Arylamino-3-oxopropanoic acid

The alkyl-2-(N-arylaminocarbonyl)-acetate III is refluxed for 2.5 hours in a solution of sodium hydroxide (9.0 g) in water (90 mL) and ethanol (90 mL). The reaction mixture is subsequently cooled and acidified with HCl to precipitate the crude product acid. The crude 3-arylamino-3-oxopropanoic acid IV is removed by filtration and recrystallized from hot water.

Step C: Condensation of a 3-arylamino-3-oxopropanoic acid (IV) with an aromatic aldehyde (V)

A solution of the arylamino-3-oxopropanoic acid IV (10 mmol), an aromatic aldehyde V (10 mmol) and benzylamine (0.4 mL) is refluxed for 3 hours in glacial acetic acid (10 mL). The solution is then cooled. Cold ether (50 mL) is added. The organic layer is separated and washed with a saturated solution of sodium bicarbonate (30 mL), sodium bisulfite (30 mL) and dilute hydrochloric acid (30 mL). The ether solution is then dried over anhydrous sodium sulfate and evaporated under reduced pressure to yield the corresponding N-aryl-3-aryl-2-propenamide I (E-isomer).

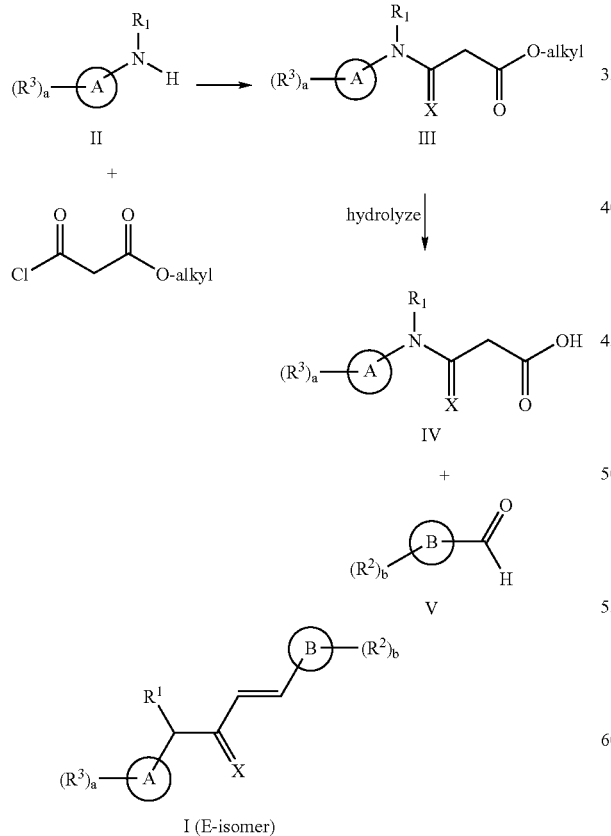

Scheme 1

According to General procedure 2, which is depicted in Scheme 2, a condensation according to the method of Nodia et al, (U.S. Pat. No. 4,337,270) is utilized, relying on the condensation of an intermediate E- or Z-aromatic acryloyl-halide VII, such as for example, a cinnamoyl chloride with an appropriate aromatic amine II, such as for example an aniline. The latter reaction is conducted in a nonprotic solvent in the presence of a base. The same compound may serve as both the nonprotic solvent and the base. Such dual-function solvents include, for example, pyridine, substituted pyridines, trimethylamine, TEA and DIPEA. The entire disclosure of U.S. Pat. No. 4,337,270 is incorporated herein by reference.

The intermediate E- or Z-aromatic acryloylhalide VII is prepared from the corresponding aromatic acrylic acid VI. The aromatic acrylic acid is reacted with a halogenating agent such as for example, thionyl chloride or phosphorous pentachloride to form the intermediate carboxylic acid chloride VII.

General Procedure 2

Condensation of (E) or (Z)- Aromatic Acryloyl Chlorides with Aromatic Amines:

According to Scheme 2, a solution of aromatic amine II (10 mmol) in pyridine (75 mL) is reacted with an (E) or (Z)-aromatic acryloyl halide VII (10 mmol) for 4 to 6 hours at 80° C. The reaction mixture is cooled and poured into ice water (IL) and concentrated hydrochloric acid (100 mL) is added. The precipitated product is separated by filtration and crystallized to yield a pure N-aryl-3-aryl-2-propenamide I. This synthesis is depicted in Scheme 2 below.

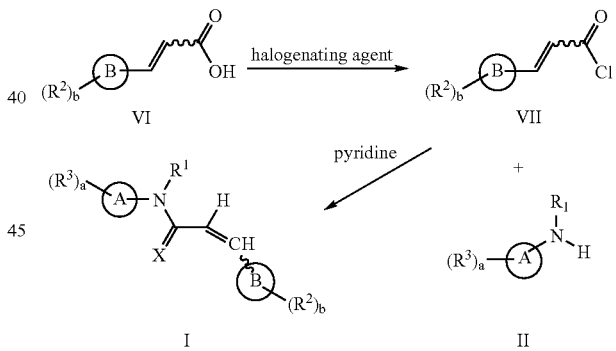

Scheme 2

According to General Procedure 3, the aromatic acrylamide I is prepared by coupling the corresponding aromatic acrylic acid VI with an aromatic amine II using an amide coupling reagent such as HATU, DIC or DCC.

Aromatic acrylic acids of general formula VI are synthetically accessible. The trans- or E-aromatic acrylic acids are easily prepared via the Heck reaction (U.S. Pat. No. 3,988,358) wherein palladium catalysis allows reaction of an alkyl acrylate ester with an iodo or bromo-substituted aromatic ring. A similar coupling reaction may be useful in the preparation of the cis- or Z-aromatic propene amides, wherein an isolable stannane acrylate is prepared from a 2-bromoacrylate ester of the Z-conformation. (*Organic Reactions*, Volume 50, "The Stille Reaction", 1997) The stannane reagent should retain the Z conformation and couple the acrylate moiety to a bromo, iodo or pseudohalogen-substituted aromatic ring with retention of the Z-stereochemistry.

General Procedure 3

Condensation of (E) or (Z)-Aromatic Acrylic Acids with Aromatic Amines:

According to Scheme 3, to a solution of an aromatic acrylic acid VI (10 mmol) in DCM (10 mL), is added an aromatic amine II (10 mmol) and DIPEA (5 mmol). This mixture is stirred at room temperature for 24 hours. The reaction progress is monitored by TLC. After the reaction is complete, DCM (25 mL) is added to the reaction mixture, and the organic layer is separated and washed with saturated sodium bicarbonate (15 mL), dilute HCl (15 mL) and water (30 mL). The organic layer is then dried (magnesium sulfate) and concentrated under reduced pressure to yield the crude N-aryl-3-arylprop-2-enamide I, which is subsequently purified by recrystallization.

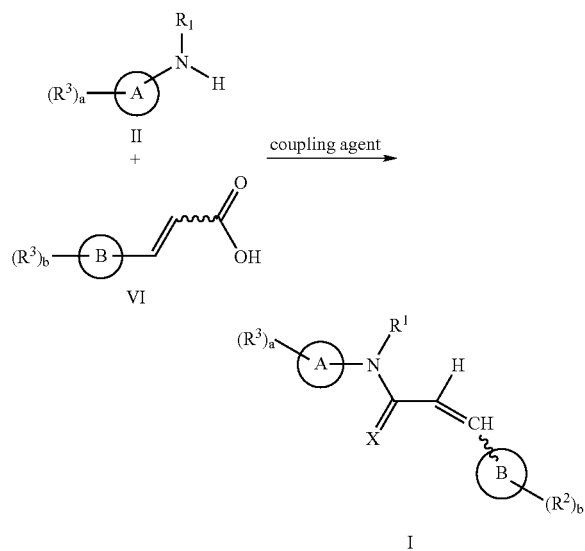

Some functional groups on the aromatic rings, in particular aromatic amine nitrogens are further derivatizeable. Derivatives of aromatic amino groups which are useful in the present invention include, for example: acylation to form carboxamide, carbamate and urea derivatives; sulfonylation to form sulfonamides, sulfonyl ureas and sulfamoyl esters; imine formation for formation of imines and for alkylation or arylation (or heteroarylation) via reductive amination; alkylation to form mono- or di-alkylamino derivatives, palladium catalyzed cross coupling to form N-aryl (or N-heteroaryl) derivatives by coupling with aromatic halides or aromatic pseudo halides such as aromatic triflates. Derivatives may also include conjugates to biological molecules such as antibodies to yield macro molecules capable of being directed to a desired site of action thereby reducing or precluding side effects associated with interaction of a drug prepared from a compound of the present invention with tissues and cells which are not proliferating abnormally.

The synthetic schemes shown above depict three synthetic strategies for preparing aryl propene amides of the invention. In addition to the amides prepared in Schemes 1-3 above, compounds of the present invention include thioamides of formula I wherein X is S. Thioamides of the present invention may be prepared according to procedures referenced in Fieser 13, 38; 15, 37 and 16, 37, by reacting the amide compounds of formula I with 2,4-bis(4-methoxyphenyl)-1,3-dithia-2,4-diphosphetane-2,4-disulfide (Lawesson's reagent) according to Scheme 4, below.

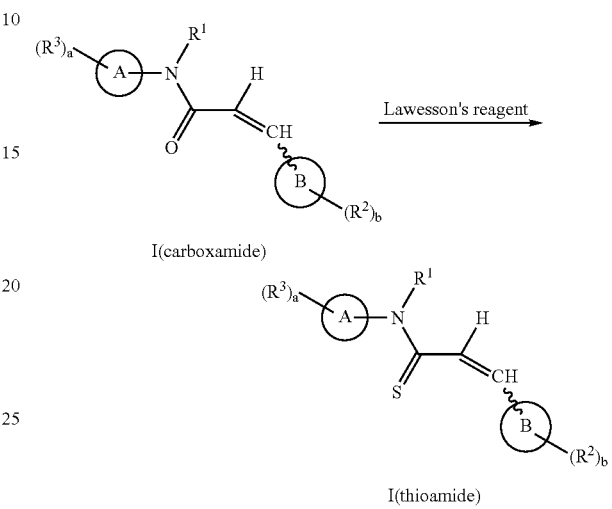

The synthetic Schemes 1-3 shown above reflect a convergent synthesis strategy. Thus A-ring and B-ring components may be synthesized and elaborated separately prior to coupling to form the target aryl propene amides. The convergent synthetic schemes shown above allow for arrangement of the assembly steps of the aryl propene amide backbone and of derivatization of aromatic amine substituents (or other derivatizable functionalities) to accommodate functional group sensitivity and/or to allow for diversity elements arising from derivatization of aromatic amines to be introduced either before or after the assembly of the aryl propene amide backbone via the coupling reactions of Schemes 1-3.

To synthesize a derivative of an A-ring amine substituent on a compound of formula I, the starting aromatic amine component II would have two amine substituents of approximately equal reactivity. Therefore, one of the amine substituents must be protected with a protecting group or otherwise rendered unreactive for either the amide coupling to make the propene amide backbone, or for the derivatization of the amine substituent. One approach to this differentiation of two aromatic amine groups is to replace one of the amine groups with a nitro. The nitro group performs the same function as a protecting group in this synthesis because it "masks" the reactive amino group during a first reaction, and on reduction to the amine, can participate in the second reaction. More specifically, the nitro group is unreactive to the amide coupling and is generally unreactive to all of the amine derivatizations desired for synthesis of compounds of the invention. Of equal importance, the nitro group can readily be reduced to generate an aromatic amine when needed. Reduction of the aromatic nitro group can be done, for example, via catalytic hydrogenation. Catalytic hydrogenation provides the capability to selectively reduce the aromatic nitro group without reducing the olefin or other functionality in the intermediate.

A simple illustration of the flexibility of the assembly and derivatization of an aromatic amino substituent on the A-ring of a compound of formula I is depicted in Scheme 5, in which a 3-acetamido-4-methoxy derivative is prepared via both strategies. In Scheme 5, the first starting A-ring synthon is 3-nitro-4-methoxy aniline [577-72-0]. This starting material allows for (step 1a) coupling to form the propene amide; (step 2a) reduction of the 3-nitro group and (step 3a) acetylation of the 3-amino group.

The second starting material is 2-methoxy-5-nitroaniline [99-59-2]. This starting material allows for (step 1b) acetylation of the 3-amino group; (step 2b) reduction of the 3-nitro group to the amino; and (step 3b) coupling to form the propene amide. This dual strategy is useful to afford facile and efficient diversification of either the B-ring aryl propene while keeping an elaborated A-ring aniline constant, or making numerous derivatives of an A-ring amine substituent as a final step while keeping the B-ring aryl propene constant. The dual synthesis routes depicted in Scheme 5 show an acetylation reaction for illustration purposes. Each of the two synthesis routes will allow for a broad range of derivatization of an amino substitution of ring A of compounds of formula I. In addition, though the scheme is shown specifically for 2-methoxy-5-nitroaniline [99-59-2] and 3-nitro-4-methoxy aniline [577-72-0], the aromatic amine derivatizations and synthetic routes may be employed with starting materials of formula SM-1 and SM-2 below,

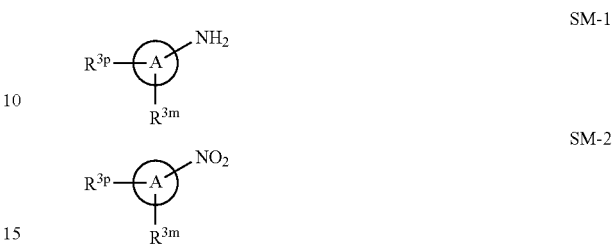

wherein in intermediate SM-1, $R^{3m}$ is —$NO_2$ and in SM-2, $R^{3m}$ is —$NH_2$ (i.e. $R^{3m}$ is formula (i), m is 0, $R^4$ is —H and $R^5$ is —$R^4$=—H).

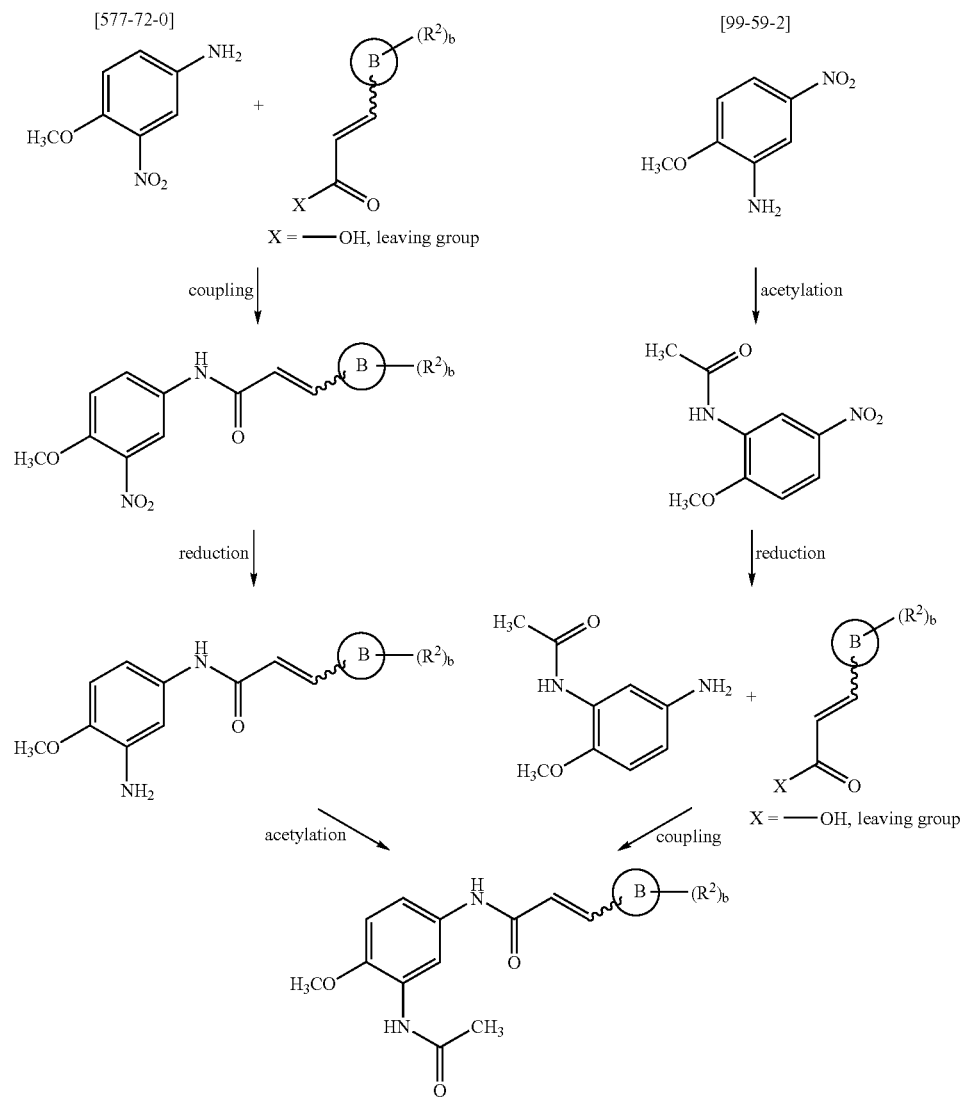

Therefore, according to one embodiment of the invention, a process is provided for preparing a compound of formula Ic:

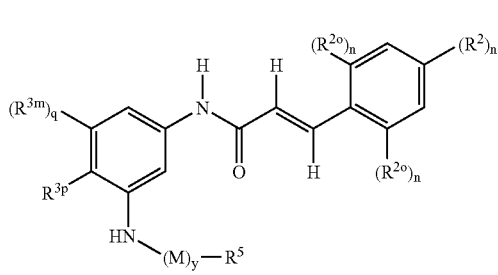

Ic or a salt thereof, comprising:

reacting an aromatic amino compound of formula Id

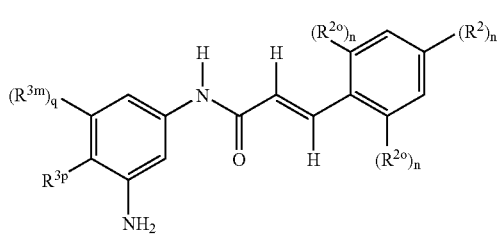

Id with an electrophilic compound of formula VIII:

R$^5$-L        VIII wherein R$^5$ comprises an electrophilic reactive center selected from the group consisting of:

(a) an alkyl moiety having a leaving group;

(b) an aryl or heteroaryl halide or aryl or heteroaryl pseudo halide;

(c) a carboxylic acid activated with a leaving group;

(d) a sulfonic acid activated with a leaving group;

(e) a carbamic acid moiety activated with a leaving group;

(f) a cyanate moiety;

(g) an aldehyde or ketone moiety, or a hydrate thereof or a ketal or acetal thereof;

(h) a carboxylic acid moiety and an amide coupling reagent; or (i) the intermediate product of a thiourea moiety and 2-chloro-1-methyl pyridinium iodide; to form a compound of formula Ic.

Thus, Table 4 below shows examples of the derivatizations which may be made of a compound of the present invention which has an amino substituent on the A ring.

TABLE 4

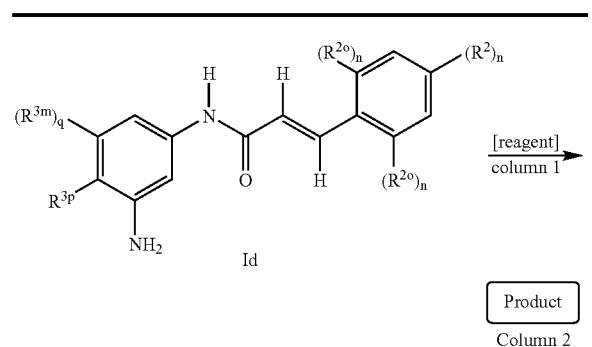

Id

Product
Column 2

| Reagents | Products |
|---|---|
| Activated (A) carboxylic or (B) carbamic acids; including carboxylic acids or amino acids in combination with amide coupling reagents, to form compounds of formula A1 and B1 respectively. | 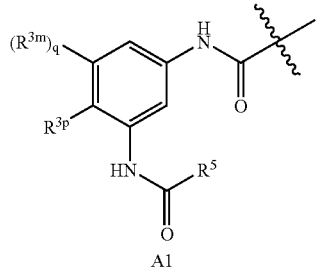 A1 <br> 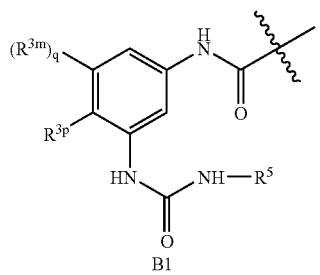 B1 |
| Activated (C) sulfonic or (D) sulfamic acids forming compounds of formula C1 and D1 respectively. | 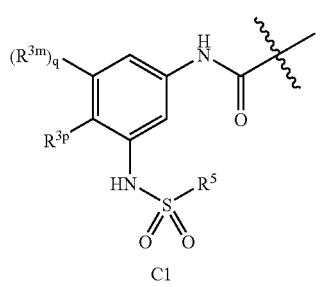 C1 <br> 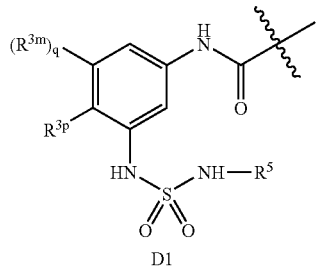 D1 |

TABLE 4-continued

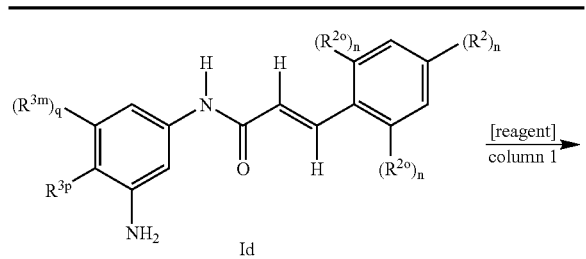

Id

[reagent] column 1 → Product Column 2

| Reagents | Products |
|---|---|
| Aryl or heteroaryl halide or pseudohalide (E) with Pd or Ni catalyst, forming compounds of formula E1. | E1 |
| Alkyl moiety with a leaving group (F), forming alkyl amine F1 | F1 |
| Aldehyde or ketone moiety (G): A. formation of substituted imine G1. B. reductive amination to form substituted amine G2. | G1 G2 |

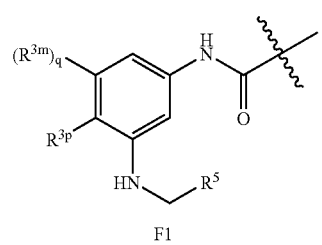

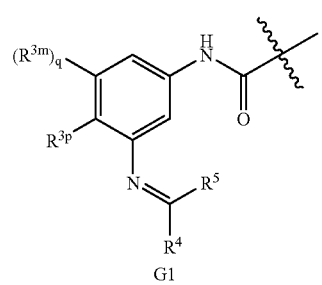

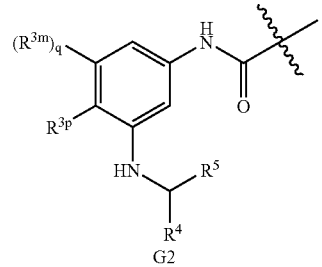

TABLE 4-continued

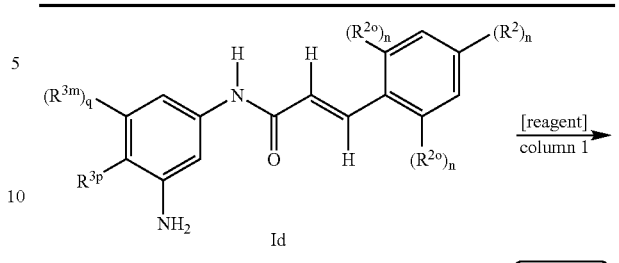

Id

[reagent] column 1 → Product Column 2

| Reagents | Products |
|---|---|
| Reagent product of a substituted thiourea and a 1-methyl or 1-phenyl-2-halopyridinium salt, (H) reacting to form the guanidine derivative H1 | H1 |

For product example formulas shown in Table 4 above, the B-ring portion of the molecule, shown in Formula Id remains unchanged under the reaction conditions. Also functional groups designated by $R^2$, $R^{2o}$, $R^{3m}$, $R^{3p}$, n and q are as defined for Formula Id above. The chemistry depicted in Table 4 above is intended to be exemplary and not exclusive of additional derivatizations of aromatic amines of formula Id or of derivatizations of other aromatic amines of formula I. In addition, the derivatizations shown above may be done on intermediates of formula SM-1

Reaction of compounds of formula I or Id with unactivated carboxylic acids of formula A to form carboxamides may be done for example at ambient temperature using a coupling agent such as, for example DIC. Suitable solvents include for example polar aprotic solvents such as dimethyl formamide (MF). The reaction also incorporates an acid scavenger such as for example a tertiary amine to consume acid formed in the reaction. This reaction may also be performed using reagents on solid support, such as for example a carbodiimide bonded to a polystyrene bead. The tertiary amine acid scavenger may likewise be a polystyrene bead-bound reagent.

The carboxylic acid used in the above reaction may be an amino acid (a natural amino acid, a synthetic amino acid or a peptide fragment. Amino acid reagents in the above reaction will be protected at the alpha amino, sidechain amino, sidechain carboxy or any other functionality which would not be stable to the coupling reaction conditions. Suitable amine protecting groups include benzyl, CBZ and FMOC.

Reaction of compounds of formula I or Id with activated carboxylic acid or carbamic acid functionalities of formula A to form amides or formula A1 and ureas of formula B1 respectively, may be done, for example at ambient temperature. Activation of carbamic or carboxylic acids is by replacement of the —OH group of a carboxy with a leaving group such as a halide. This preparation may be done, for example by halogenating the carboxylic or carbamic acid. A common reagent for performing this reaction is thionyl chloride for synthesis of acid chlorides or carbamoyl chlorides. Bromides and fluorides may also be prepared using such reagents as thionyl bromide or hexafluoro acetone respectively. Other leaving groups include mixed anhydrides which may be prepared by chemistry known in the art.

Similarly, sulfonamides of formula C1 may be prepared by reacting activated sulfonic acids formula C, particularly sulfonyl chlorides with compounds of formula I, Id or SM-1. The reaction may be done at ambient temperature using an acid scavenger as described above.

Reaction of compounds of formula I, Id or SM-1 with aryl or heteroaryl halides of formula E to make the corresponding diaryl amine of formula E1, may be done using a transition metal catalyst, particularly a palladium catalyst such as for example tetrakis triphenylphosphinopalladium. The aromatic halogen compound is preferably an aromatic bromide, however iodides and chlorides are also useful. The reaction may be done in a dry solvent including for example such solvents as toluene, THF and DMF. The reaction is done in the presence of a base such as for example cesium carbonate or potassium tert-butoxide.

Reaction of compounds of formula I, Id or SM-1 with aldehydes or ketones of formula G to form the imine of formula G1 may be done using acid catalysis and using methods that remove water as it is formed in the reaction. A suitable acid catalyst is toluene sulfonic acid. Suitable conditions for removing water formed in the reaction include molecular sieves and azeotropic removal via performance of the reaction in a solvent that forms a low-boiling azeotrope with water. Such solvents include toluene and chloroform.

In a variation of the imine formation, a reductive amination may be done as an alternative method of preparing alkyl derivatives of the formula I and Id aromatic amines of formula G2. In this procedure, a reducing agent is added to the reaction mixture with the aromatic amine of formula I or Id and the aldehyde or ketone. Suitable reducing conditions will favor reduction of the product imine selectively over the starting aldehyde or ketone. Suitable conditions include for example, reduction with sodium cyanoborohydride under acidic conditions.

Reaction of aromatic amines of formula I, Id or SM-1 to form guanidine derivatives of formula H1 may be done via reaction with a reagent H, formed by reacting a thiourea, such as N,N'-bis-(tert-butoxycarbonyl)thiourea with a 1-methyl or 1-phenyl-2-halopyridinium salt, particularly 2-chloro-1-methylpyridinium iodide.

Thus in other embodiments of the present invention, there are provided compounds of formula A1, formula B1, formula C1, formula D1, formula E1, formula F1, formula G1, formula G2 and formula H1, wherein:

$R^2$, $R^{2o}$, n, $R^{3p}$, $R^{3m}$ and q are as defined for formula Id above;

or salts of such compounds.

Preparation of Id as an Intermediate for Derivatization of the 3-Amino Group

In a further embodiment thereof, there is provided a process for preparing a compound of formula Id or a salt thereof:

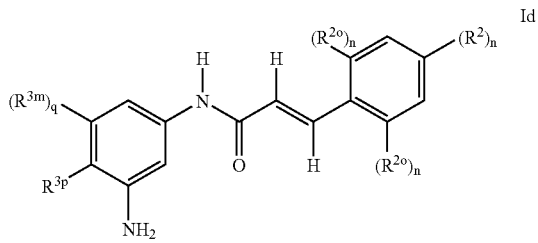

Id wherein $R^2$, $R^{2o}$, $R^{3m}$, $R^{3p}$ and n are defined as for formula I above; comprising:

chemically reducing a compound of formula Ie (E conformation):

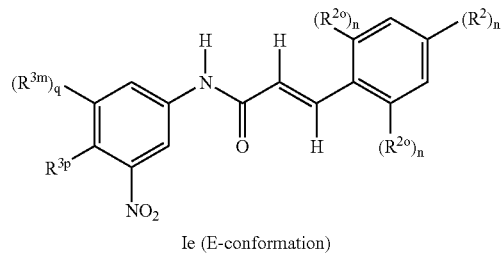

Ie (E-conformation)

to form a compound of formula Id or a salt of such a compound.

Preparation of the 3-Nitro Intermediate Ie by Three Different Routes

A. Preparation of Ie Via Coupling an Aromatic Aldehyde with a Malonyl Anilide

In a further embodiment thereof, there is provided a process for preparing a compound of formula Ie or a salt thereof:

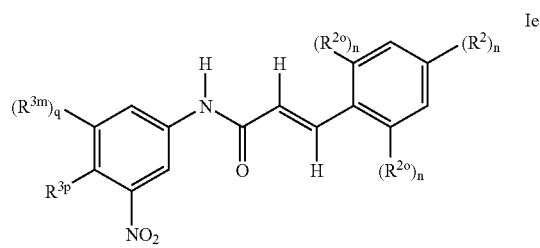

Ie wherein $R^2$, $R^{2o}$, $R^{3m}$, $R^{3p}$, q and n are defined as for formula I above; and wherein the olefin double bond is in the E conformation; comprising:

(1) coupling a compound of formula IIb:

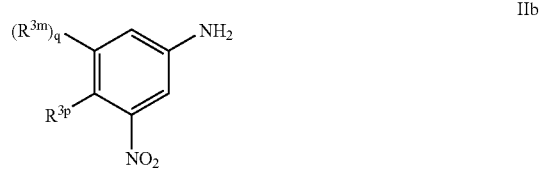

IIb with an alkyl ester of a malonic acid halide:

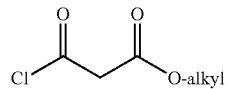

to yield a carboxylic ester compound of formula IIIb:

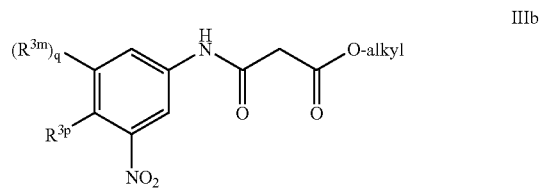

IIIb (2) hydrolyzing the carboxylic ester compound of formula IIIb to form a carboxylic acid compound of formula IVb; and

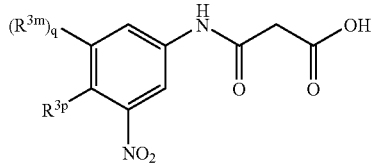

IVb (3) coupling of the carboxylic acid compound of formula IVb with an aromatic aldehyde of formula V:

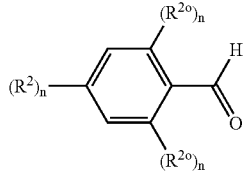

Vb in an acidic solvent or solvent mixture, particularly, glacial acetic acid at elevated temperature to form a compound of formula Ie or a salt of such a compound.

The alkyl ester of a malonic acid halide employed as a reagent in step 1 of the above preparation of a compound of formula Ic preferably comprises a $(C_1-C_{10})$alkyl ester, more preferably a $(C_1-C_5)$alkyl ester, most preferably a commercially available reagent such as for example the methyl or ethyl ester of malonic acid chloride.

B. Preparation of Ie Via Coupling an Aromatic Amine with an Aryl Propene Acid Halide.

In another embodiment thereof, there is provided a process for preparing a compound of formula Ie or a salt thereof:

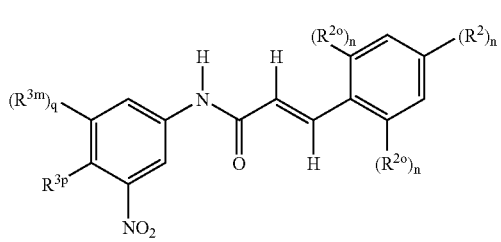

Ie wherein $R^2$, $R^{2o}$, $R^{3m}$, $R^{3p}$, q and n are defined as for formula I above; comprising:

(1) halogenating a carboxylic acid of formula VIb with a halogenating agent:

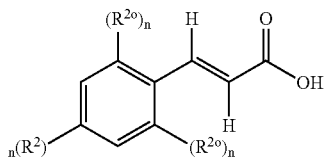

VIb to form an acid halide of formula VIIb:

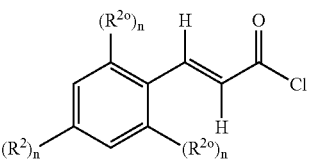

VIIb (2) coupling the acid halide VIIb to an aromatic amino compound of formula IIb

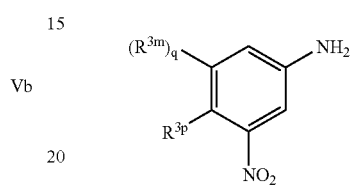

IIb to form an amide compound of formula Ie or a salt of such a compound.

C. Preparation of Ie Via Coupling an Aromatic Amine with an Aryl Propene Acid.

In another embodiment of the invention, there is provided a process for preparing a compound of formula Ie or a salt thereof:

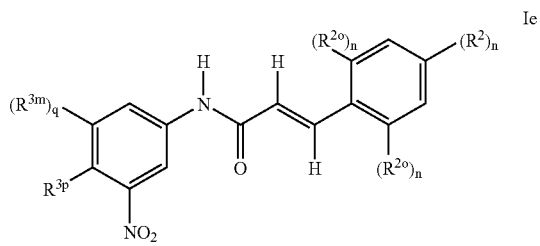

Ie wherein $R^2$, $R^{2o}$, $R^{3m}$, $R^{3p}$, q and n are defined as for formula I above; comprising:

reacting an aromatic amino compound of formula IIb

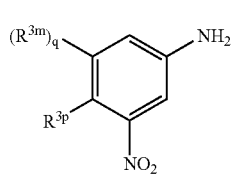

IIb with a carboxylic acid compound of formula VIb:

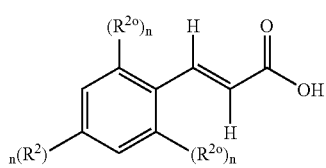

VIb and an amide coupling agent, to form a compound of formula Ie or a salt of such a compound.

Preparation of a Compound of Formula Ic Via Derivatization of a Nitro Aniline Followed by Reduction of the Nitro Group to an Amino Group and Coupling to an Aryl Propene Acid.

In another embodiment of the invention, there is provided a process for preparing a compound of formula Ic or a salt thereof:

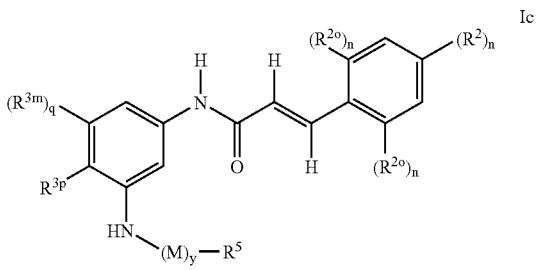

wherein $R^2$, $R^{2o}$, $R^{3m}$, $R^{3p}$, q, n, M, y and $R^5$ are defined as for formula I above; comprising (1) reacting an aromatic amine of formula IX

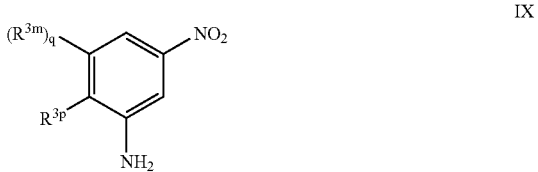

with an electrophilic compound of formula VIII:

wherein L comprises an electrophilic reactive center selected from the group consisting of:

(a) an alkyl moiety having a leaving group;
(b) an aryl or heteroaryl halide or aryl or heteroaryl pseudo halide;
(c) a carboxylic acid activated with a leaving group;
(d) a sulfonic acid activated with a leaving group;
(e) a carbamic acid moiety activated with a leaving group;
(f) a cyanate moiety;
(g) an aldehyde or ketone moiety, or a hydrate thereof or a ketal or acetal thereof;
(h) a carboxylic acid moiety and an amide coupling reagent; or
(i) the intermediate product of a thiourea moiety and 2-chloro-1-methyl pyridinium iodide; to form a compound of formula IXa:

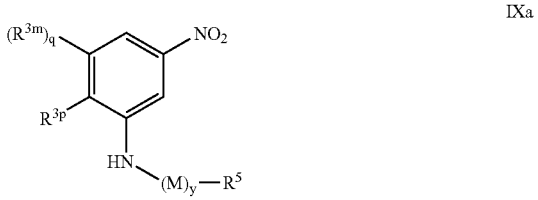

(2) optionally protecting the —NH-$(M)_y$-$R^5$ moiety;

(3) chemically reducing said nitro compound of formula IXa to form the aromatic amine IXb:

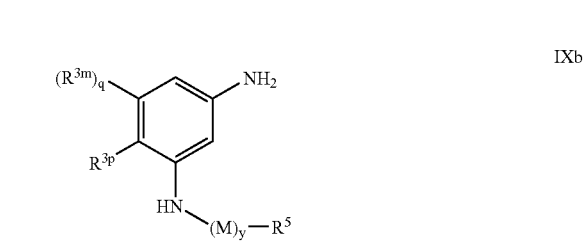

(3) reacting aromatic amine IXb with a carboxylic acid compound of formula VIb:

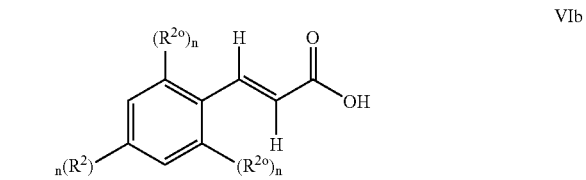

and an amide coupling agent; and (5) optionally removing said protecting group to form a compound of formula Ic; or a salt of such a compound.

The —NH-$(M)_y$-$R^5$ moiety is optionally protected by a suitable protecting group bonded to the nitrogen atom of the —NH-$(M)_y$-$R^5$ moiety. A suitable protecting group is one which prevents the nitrogen of the —NH-$(M)_y$-$R^5$ moiety from reacting under the reaction conditions of succeeding steps 3 and 4. Suitable protecting groups include, for example, benzyl and substituted benzyl, CBZ, BOC and FMOC groups.

Preparation of a Compound of Formula Ic Via Coupling a 3-Amino Malonyl Anilide (Derivatized at the 3-Amino) with an Aromatic Aldehyde In a further embodiment of the invention, there is provided a process for preparing a compound of formula Ic or a salt thereof:

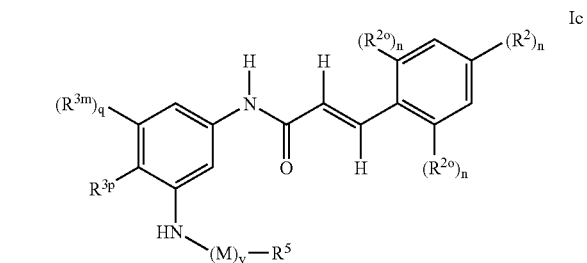

wherein $R^2$, $R^{2o}$, $R^{3m}$, $R^{3p}$, q, n, M, y and $R^5$ are defined as for formula I above; and wherein the olefin double bond is in the E conformation; comprising:

(1) coupling a compound of formula IXb:

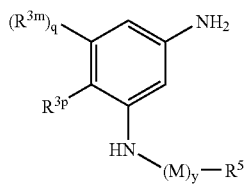

IXb wherein the —NH-(M)$_y$-R$^5$ moiety is optionally protected with a protecting group;
with an alkyl ester of a malonic acid halide:

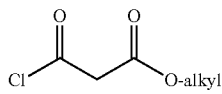

to yield a carboxylic ester compound of formula IXc:

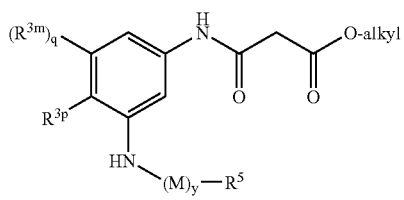

IXc (2) hydrolyzing of the carboxylic ester compound of formula IXc to form a carboxylic acid compound of formula IXd;

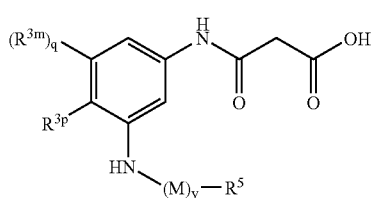

IXd (3) coupling of the carboxylic acid compound of formula IVb with an aromatic aldehyde of formula Vb:

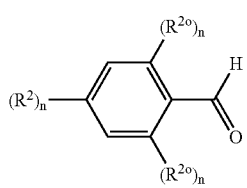

Vb in an acidic solvent or an acidic solvent mixture, particularly glacial acetic acid at elevated temperature; and
(4) optionally removing said protecting group to form a compound of formula Ic; or a salt of such a compound.

The —NH-(M)$_y$-R$^5$ moiety is optionally protected as described in the above preparation of a compound of formula Ic via derivatization of a nitro aniline followed by reduction of the nitro group to an amino group and coupling to an aryl propene acid.

The alkyl ester of a malonic acid halide employed as a reagent in step 1 of the above preparation of a compound of formula Ic preferably comprises a (C$_1$-C$_{10}$)alkyl ester, more preferably a (C$_1$-C$_5$)alkyl ester, most preferably a commercially available reagent such as for example the methyl or ethyl ester of malonic acid chloride.

Preparation of a Compound of Formula Ic Via Coupling a 3-Amino Aniline (Optionally Protected) with an Aryl Propene Acid Halide In another embodiment thereof, there is provided a process for preparing a compound of formula Ic or a salt thereof:

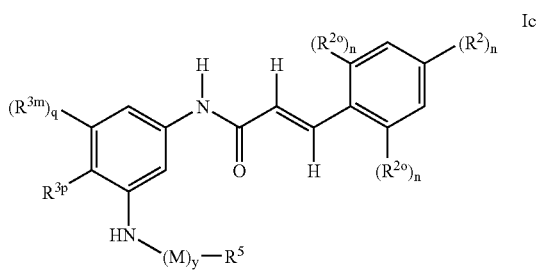

Ic wherein R$^2$, R$^{2o}$, R$^{3m}$, R$^{3p}$, q, n, M, y and R$^5$ are defined as for formula I above:
comprising:
(1) halogenating a carboxylic acid of formula VIb with a halogenating agent:

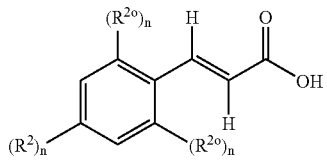

VIb to form an acid halide of formula VIIb:

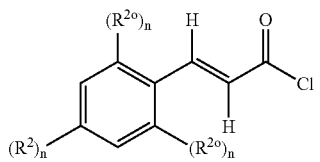

VIIb (2) coupling the acid halide VIIb to an aromatic amino compound of formula IXb

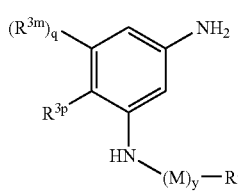

IXb wherein the —NH-(M)$_y$-R$^5$ moiety is optionally protected with a protecting group; and
(3) optionally removing said protecting group to form an amide compound of formula Ic; or a salt of such a compound.

The —NH-$(M)_y$-$R^5$ moiety is optionally protected as described in the two above preparations of a compound of formula Ic.

Preparation of Thioamide Compounds of Formula Is

In another embodiment of the invention, there is provided a process for preparing a compound of formula Is or a salt thereof,
comprising:
reacting a compound of formula Ic:

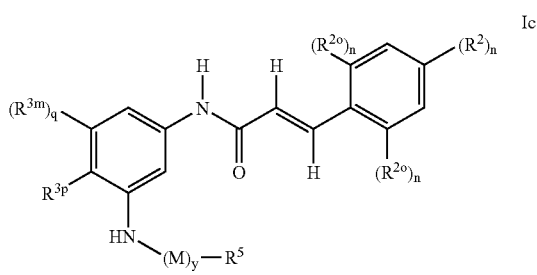

wherein $R^2$, $R^{2o}$, $R^{3m}$, $R^{3p}$, q, n, M, y and $R^5$ are defined as for formula I above;
with 2,4-bis(4-methoxyphenyl)-1,3-dithia-2,4-diphosphetane-2,4-disulfide,
to form a compound of formula Is.

Halides which may comprise a leaving group component of the electrophilic functionality $R^5$-L are preferably chloro, bromo or iodo. Suitable leaving groups also include sulfonate esters such as tosylate, nosylate, mesylate and triflate. The term "pseudo halide" refers to a moiety, such as a triflate or mesylate, which behaves like a halide in palladium or nickel-catalyzed amination reactions.

Carboxylic acid moieties which may comprise the electrophilic functionality $R^6$-L include, for example, amino acid residues bearing optional protecting groups on any alpha-amino functionality, sidechain amino functionality, alpha carboxylic acid functionality, sidechain carboxylic acid functionality or other sidechain functionalities that require a protecting group. Such amino acids may be naturally occurring amino acids or synthetic amino acids including amino acids of either R- or S-absolute configuration.

Following the aforesaid processes of coupling compounds: of formula IXb to compounds of formulae VIb or VIIb, of formula IXd to compounds of formula Vb, or of compounds of formula Id to compounds of formula VIII, any protecting groups used in the synthesis of a compound of formula I are optionally removed.

The compounds of the present invention may take the form of salts. The term "salts", embraces salts commonly used to form alkali metal salts and to form addition salts of free acids or free bases. The term "pharmaceutically-acceptable salt" refers to salts which possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, beta-hydroxybutyric, salicyclic, galactaric and galacturonic acid. Examples of pharmaceutically unacceptable acid addition salts include perchlorates and tetrafluoroborates.

Suitable pharmaceutically acceptable base addition salts of compounds of the invention include for example, metallic salts made from calcium, magnesium, potassium, sodium and zinc or organic salts made from N,N'-dibenzylethylenediamine, chloroprocaine, choline, diethanqlamine, ethylenediamine, meglumine (N-methylglucamine) and procaine. Examples of pharmaceutically unacceptable salts include lithium salts and cyanate salts. All of these salts may be prepared by conventional means from the corresponding aryl or heteroaryl propene amide by reacting, for example, the appropriate acid or base with the compound of formula I.

It will be understood that when compounds of the present invention contain one or more chiral centers, the compounds may exist in, and may be isolated as pure enantiomeric or diastereomeric forms or as racemic mixtures. The present invention therefore includes any possible enantiqmers, diastereomers, racemates or mixtures thereof of the compounds of the invention which are biologically active in the treatment of cancer or other proliferative disease states.

It is understood that due to chemical properties (i.e., resonance lending some double bond character to the C—N bond) of restricted rotation about the amide bond linkage (as illustrated below) it is possible, to observe separate rotamer species and even, under some circumstances, to isolate such species. It is further understood that certain structural elements, including steric bulk or substituents on the amide nitrogen, may enhance the stability of a rotamer to the extent that a compound may be isolated as, and exist indefinitely as a single stable rotamer. The present invention therefore includes any possible stable rotamers of formula I which are biologically active in the treatment of cancer or other proliferative disease states.

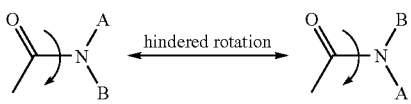

The compounds of the invention may be administered to individuals (mammals, including animals and humans) afflicted with cancer.

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's fibrosis, Dupuytren's fibrosis, restenosis and cirrhosis.

The compounds of the invention are further believed useful in the protection of normal cells from the cytotoxic and genetic effects of exposure to radiation, in individuals who have incurred, who will in the future incur and who are at risk for incurring exposure to ionizing radiation.

In addition, the compounds of the invention are believed useful in protecting individuals from the cytotoxic side effects of chemotherapeutic agents, particularly mitotic phase cell cycle inhibitors and topoisomerase inhibitors, used in the treatment of cancer and other proliferative disorders.

For treating proliferative disorders, for providing cytoprotection from the cytotoxic and genetic effects of ionizing radiation and for providing cytoprotection from cytotoxic effects of chemotherapeutic agents, the specific dose of compound according to the invention to obtain therapeutic benefit will, of course, be determined by the particular circumstances of the individual patient including, the size, weight, age and sex of the patient. Also determinative will be the nature and stage of the disease (or cell damage) and the disease aggressiveness (or dose of ionizing radiation or chemotherapeutic agent), and the route of administration. For example, a daily dosage of from about 0.05 to about 50 mg/kg/day may be utilized. Higher or lower doses are also contemplated.

For radioprotective administration, the compounds of the invention should be administered far enough in advance of the therapeutic radiation such that the compound is able to reach the normal cells of the subject in sufficient concentration to exert a radioprotective effect on the normal cells. The pharmacokinetics of specific compounds may be determined by means known in the art and tissue levels of a compound in a particular individual may be determined by conventional analyses.

The compound may be administered as much as about 24 hours, preferably no more than about 18 hours, prior to administration of the radiation. In one embodiment, the therapy is administered at least about 6-12 hours before administration of the therapeutic radiation. Most preferably, the compound is administered once at about 18 hours and again at about 6 hours before the radiation exposure. One or more aryl or heteroaryl propene amides may be administered simultaneously, or different aryl or heteroaryl propene amides may be administered at different times during the treatment.

Where the therapeutic radiation is administered in serial fashion, it is preferable to intercalate the administration of one or more radioprotective compounds within the schedule of radiation treatments. As above, different radioprotective compounds of the invention may be administered either simultaneously or at different times during the treatment. Preferably, an about 24-hour period separates administration of the radioprotective compound and the therapeutic radiation. More preferably, the administration of the radioprotective compound and the therapeutic radiation is separated by about 6 to 18 hours. This strategy will yield significant reduction of radiation-induced side effects without affecting the anticancer activity of the therapeutic radiation.

For example, therapeutic radiation at a dose of 0.1 Gy may be given daily for five consecutive days, with a two-day rest, for a total period of 6-8 weeks. One or more aryl or heteroaryl propene amides may be administered to the subject 18 hours previous to each round of radiation. It should be pointed out, however, that more aggressive treatment schedules, i.e., delivery of a higher dosage, is contemplated according to the present invention due to the protection of the normal cells afforded by the radioprotective compounds. Thus, the radioprotective effect of the compound increases the therapeutic index of the therapeutic radiation, and may permit the physician to safely increase the dosage of therapeutic radiation above presently recommended levels without risking increased damage to the surrounding normal cells and tissues.

The radioprotective compounds of the invention are further useful in protecting normal bone marrow cells from radiologic treatments designed to destroy hematologic neoplastic cells or tumor cells which have metastasized into the bone marrow. Such cells include, for example, myeloid leukemia cells. The appearance of these cells in the bone marrow and elsewhere in the body is associated with various disease conditions, such as the French-American-British (FAB) subtypes of acute myelogenous leukemias (AML), chronic myeloid leukemia (CML), and acute lymphocytic leukemia (ALL).

CML, in particular, is characterized by abnormal proliferation of immature granulocytes (e.g., neutrophils, eosinophils, and basophils) in the blood, bone marrow, spleen, liver, and other tissues and accumulation of granulocytic precursors in these tissues. The subject who presents with such symptoms will typically have more than 20,000 white blood cells per microliter of blood, and the count may exceed 400,000. Virtually all CML patients will develop "blast crisis", the terminal stage of the disease during which immature blast cells rapidly proliferate, leading to death.

Other subjects suffer from metastatic tumors, and require treatment with total body irradiation (TBI). Because TBI will also kill the subject's hematopoietic cells, a portion of the subject's bone marrow is removed prior to irradiation for subsequent reimplantation. However, metastatic tumor cells are likely present in the bone marrow, and reimplantation often results in a relapse of the cancer within a short time.

Subjects presenting with neoplastic diseases of the bone marrow or metastatic tumors may be treated by removing a portion of the bone marrow (also called "harvesting"), purging the harvested bone marrow of malignant stem cells, and reimplanting the purged bone marrow. Preferably, the subject is treated with radiation or some other anti-cancer therapy before the autologous purged bone marrow is reimplanted.

Thus, the invention provides a method of reducing the number of malignant cells in bone marrow, comprising the steps of removing a portion of the subject's bone marrow, administering an effective amount of at least one radioprotective compound according to the present invention and irradiating the treated bone marrow with a sufficient dose of ionizing radiation such that malignant cells in the bone marrow are killed. As used herein, "malignant cell" means any uncontrollably proliferating cell, such a tumor cell or neoplastic cell. The radioprotective compounds protect the normal hematopoietic cells present in the bone marrow from the deleterious effects of the ionizing radiation. The compounds also exhibit a direct killing effect on the malignant cells. The number of malignant cells in the bone marrow is significantly reduced prior to reimplantation, thus minimizing the occurrence of a relapse.

Preferably, each aryl or heteroaryl propene amide is administered in a concentration from about 0.25 to about 100 micromolar; more preferably, from about 1.0 to about 50 micromolar; in particular from about 2.0 to about 25 micromolar. Particularly preferred concentrations are 0.5, 1.0 and 2.5 micromolar and 5, 10 and 20 micromolar. Higher or lower concentrations may also be used.

The radioprotective compounds may be added directly to the harvested bone marrow, but are preferably dissolved in an organic solvent such as dimethylsulfoxide (DMSO). Pharmaceutical formulations of aryl and heteroaryl propene amides such as are described in more detail below may also be used.

Preferably, the radioprotective compound is added to the harvested bone marrow about 20 hours prior to radiation exposure, preferably no more than about 24 hours prior to radiation exposure. In one embodiment, the radioprotective compound is administered to the harvested bone marrow at least about 6 hours before radiation exposure. One or more compounds may be administered simultaneously, or different compounds may be administered at different times. Other dosage regimens are also contemplated.

If the subject is to be treated with ionizing radiation prior to reimplantation of the purged bone marrow, the subject may be treated with one or more radioprotective compounds prior to receiving the ionizing radiation dose, as described above.

A subject may also be exposed to ionizing radiation from occupation or environmental sources, as discussed in the background section. For purposes of the invention, the source of the radiation is not as important as the type (i.e., acute or chronic) and dose level absorbed by the subject. It is understood that the following discussion encompasses ionizing radiation exposures from both occupational and environmental sources.

Subjects suffering from effects of acute or chronic exposure to ionizing radiation that are not immediately fatal are said to have remediable radiation damage. Such remediable radiation damage can reduced or eliminated by the compounds and methods of the present invention.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01 Gy) and about 5000 millirem (0.05 Gy) over a period greater than 24 hours, or a localized dose of 15,000 millirem (0.15 Gy) to 50,000 millirem (0.5 Gy) over a period greater than 24 hours.

The invention therefore provides a method for treating individuals who have incurred remediable radiation damage from acute or chronic exposure to ionizing radiation, comprising reducing or eliminating the cytotoxic effects of radiation exposure on normal cells and tissues by administering an effective amount of at least one radioprotective compound. The compound is preferably administered in as short a time as possible following radiation exposure, for example between 0-6 hours following exposure.

Remediable radiation damage may take the form of cytotoxic and genotoxic (i.e., adverse genetic) effects in the subject. In another embodiment, there is therefore provided a method of reducing or eliminating the cytotoxic and genotoxic effects of radiation exposure on normal cells and tissues, comprising administering an effective amount of at least one radioprotective compound prior to acute or chronic radiation exposure. The compound may be administered, for example about 24 hours prior to radiation exposure, preferably no more than about 18 hours prior to radiation exposure. In one embodiment, the compound is administered at least about 6 hours before radiation exposure. Most preferably, the compound is administered at about 18 and again at about 6 hours before the radiation exposure. One or more radioprotective compounds may be administered simultaneously, or different radioprotective compounds may be administered at different times.

When multiple acute exposures are anticipated, the radioprotective compounds of the invention may be administered multiple times. For example, if fire or rescue personnel must enter contaminated areas multiple times, radioprotective compounds of the invention may be administered prior to each exposure. Preferably, an about 24-hour period separates administration of the compound and the radiation exposure. More preferably, the administration of radioprotective compounds and the radiation exposure is separated by about 6 to 18 hours. It is also contemplated that a worker in a nuclear power plant may be administered an effective amount of a radioprotective compound of the invention prior to beginning each shift, to reduce or eliminate the effects of exposure to ionizing radiation.

If a subject is anticipating chronic exposure to ionizing radiation, the radioprotective compound may be administered periodically throughout the duration of anticipated exposure. For example, a nuclear power plant worker or a soldier operating in a forward area contaminated with radioactive fallout may be given the radioprotective compound every 24 hours, preferably every 6-18 hours, in order to mitigate the effects of radiation damage. Likewise, the radioprotective compound may be periodically administered to civilians living in areas contaminated by radioactive fallout until the area is decontaminated or the civilians are removed to a safer environment.

For providing cytoprotection from cytotoxic effects of chemotherapeutic agents, the schedule of administration of the cytotoxic drug, ie., mitotic phase cell cycle inhibitor or topoisomerase inhibitor, can be any schedule with the stipulation that the aryl or heteroaryl propene amide is administered prior to the cytotoxic drug. The cytoprotective compound should be administered far enough in advance of the cytotoxic drug such that the former is able to reach the normal cells of the patient in sufficient concentration to exert a cytoprotective effect on the normal cells. Again, individual drug pharmacokinetics and blood levels of a specific drug in a specific patient are factors that may be determined by methods known in the art.

In one embodiment, the cytoprotective compound is administered at least about 4 hours before administration of the cytotoxic drug. The compound may be administered as much as about 48 hours, preferably no more than about 36 hours, prior to administration of the cytotoxic drug. Most preferably, the compound is administered about 24 hours before the cytotoxic drug. The compound may be administered more or less than 24 hours before the cytotoxic effect, but the protective effect of the compounds is greatest when administered about 24 hours before the cytotoxic drug. One or more cytotoxic drugs may be administered. Similarly, one or more of the aryl or heteroaryl propene amides may be combined.

Where the cytotoxic drug or drugs is administered in serial fashion, it may prove practical to intercalate cytoprotective compounds of the invention within the schedule with the caveat that a 4-48 hour period, preferably a 12-36 hour period, most preferably a 24 hour period, separates administration of the two drug types. This strategy will yield partial to complete eradication of cytotoxic drug side effects without affecting anticancer activity.

For example, the mitotic inhibitor may be given daily, or every fourth day, or every twenty-first day. The aryl or heteroaryl propene amide may be given 24 hours previous to each round of inhibitor administration, both as a cytoprotective agent and as an antitumor agent.

The compounds of the invention may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical, subcutaneous or sublingual administration. Also contemplated within the scope of the invention is the instillation of drug in the body of the patient in a controlled formulation, with systemic or local release of the drug to occur at a later time. For anticancer use, the drug may be localized in a depot for controlled release to the circulation, or local site of tumor growth.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The practice of the invention is illustrated by the following non-limiting examples. Representative compounds are listed in Table 5.

EXAMPLE 1

(E)-N-(4-Methoxyphenyl)-3-(2,4,6-trimethoxyphenyl)-2-propen-amide

A solution of 4-methoxyphenylamino-3-oxoprpanoic acid and 2,4,6-trimethoxy benzaldehyde was reacted according to General Procedure 1. The title compound, melting point 198-200° C, was thereby obtained in 78% yield.

NMR (DMSO-d6), δ 3.78 (s, 3H), 3.86 (s, 6H), 3.88 (s, 3H), 6.13 (s, 2H), 6.85 (d, 1H vinylic), 6.88-7.56 (m, aromatic), 8.12 (d, 1H vinylic, J=16.0 Hz).

EXAMPLE 2

(E)-N-(4-Methophenyl)-3-(2,6-dimethoxypheyl)-2-propenamide

A solution of 4-methoxyphenylamino-3-oxoprpanoic acid and 2,6-dimethoxy benzaldehyde was reacted according to General Procedure 1. The title compound, melting point 203-204° C., was thereby obtained in 63% yield.

NMR (DMSO-d6), δ 3.80 (s, 3H), 3.90 (s, 6H), 7.0 (d, 1H vinylic, J=15.5 Hz), 6.57-7.57 (m, aromatic), 8.17 (d, 1H vinylic, J=15.5 Hz).

EXAMPLE 3

(E)-N-(4-Methoxy-3-nitropheneyl-3-(3,4,5-trimethoxphenyl-2-propenamide

A solution of 4-methoxy-3-nitroaniline and 3,4,5-trimethoxy cinnamic acid was reacted according to General Procedure 3. The title compound, melting point 186-189° C., was thereby obtained in 35% yield.

NMR (DMSO-d6), δ 3.84 (s, 3H), 3.90 (s, 9H), 7.2 (d, 1H vinylic, J=16.0 Hz), 7.37-8.20 (m, aromatic).

EXAMPLE 4

(E)-N-(4-Methoxy-3-aminophenyl)-3-(3,4,5-trimethoxyphenyl)-2-propenamide

A solution of N-(4-methoxy-3-nitrophenyl)-3-(3,4,5-trimethoxyphenyl)-2-propenamide (Example 3) (1.3 mmol) in acetone/water (10:5) was heated to 50° C. After 30 minutes, sodium hydrosulfite ($Na_2S_2O_4$) (26.3 mmol) was added slowly. The resulting mixture was heated at reflux for one hour and then cooled to room temperature. Water was added to the cooled reaction mixture. The product was isolated by extraction with ethyl acetate. The organic layer washed with 10% aqueous $NaHCO_3$ and then dried over anhydrous $Na_2SO_4$. The solvent was removed under reduced pressure. The crude product thereby obtained was recrystallized from 2-propanol to yield the title compound, melting point 202-204° C., in 32% yield.

NMR (DMSO-d6) δ 3.82 (s, 3H), 3.88 (s, 6H), 6.45 (d, 1H vinylicJ=15.5 Hz), 6.70-7.45 (m, aromatic), 7.60 (d, 1H vinylicJ=15.5 Hz).

EXAMPLE 5

(E)-N-(4-methoxy-3-nitrophenyl)-3-(2,4,6-trimethoxyphenyl-2-propenamide

A solution of 4-methoxy-3-nitrophenylamino-3-oxopropanoic acid and 2,4,6-trimethoxy benzaldehyde was reacted according to General Procedure 1. The title compound, melting point 138-140° C., was thereby obtained in 58% yield.

NMR (DMSO-d6), δ 3.84 (s, 3H), 3.86 (s, 6H), 3.92 (s,3H), 6.18 (s, 2H), 7.12 (d, 1H vinylic), 6.94-8.17 (m, aromatic).

EXAMPLE 6

(E)-N-(4-methoxy-3-aminophenyl)-3-(2,4,6-trimethoxyphenyl)-2-propenamide

A solution of N-(4-methoxy-3-nitrophenyl)-3-(2,4,6-trimethoxyphenyl)-2-propenamide (example 5) (1.3mmol) in acetone/water (10:5) was heated to 50° C. After 30 min, sodium hydrosulfite (Na$_2$S$_2$O$_4$) 26.3 mmol) was added slowly. The resulting mixture was heated at reflux (50° C.) for one hour. The mixture was then cooled to room temperature and water was added. The product was isolated by extraction with ethyl acetate. The organic layer washed with 10% aqueous NaHCO$_3$ and then dried over anhydrous Na$_2$SO$_4$. The solvent was removed under reduced pressure. The crude product thereby obtained was recrystallized from 2-propanol to yield the title compound, melting point 92-94° C., in 48% yield.

NMR (DMSO-d6) δ 3.82 (s, 3H), 3.88 (s, 6H), 6.13 (s, 2H), 6.45 (d, 1H vinylic, J=15.5 Hz), 6.70-7.45 (m, aromatic), 7.60 (d, 1H vinylic J=15.5 Hz).

EXAMPLE 7

(E)-N-(4-Methoxy-3-nitrophenyl)-3-(2,3,4,5,6-pentafluorophenyl)-2-propenamide

A solution of 4-methoxy-3-nitrophenylamino-3-oxopropanoic acid and 2,3,4,5,6-pentafluorobenzaldehyde was reacted according to General Procedure 1. The title compound, melting point 265-266° C., was thereby obtained in 48% yield.

NMR (DMSO-d6), δ 3.80 (s, 3H), 7.25 (d, 1H vinylic), 7.60 (d, 1H vinylic), 7.20-7.73 (m, aromatic).

EXAMPLE 8

(E)-N-(4-Methoxy-3-nitrophenyl)-3-(3-fluoro-4-nitrophenyl)-2-propenamide

A solution of 4-methoxy-3-nitrophenylamino-3-oxopropanoic acid and 3-fluoro-4-nitrobenzaldehyde was reacted according to General Procedure 1. The title compound, melting point 263-265° C., was thereby obtained in 57% yield.

NMR (DMSO-d6), δ 3.78 (s, 3H), 3.80 (s, 6H), 7.10 (d, 1H vinylic), 7.62 (d, 1H vinylic), 7.20-7.85 (m, aromatic).

EXAMPLE 9

(E)-N-(4-Methoxy-3-aminophenyl)-3-(3-fluoro-4-aminophenyl)-2-propenamide

A solution of N-(4-methoxy-3-nitrophenyl)-3-(3-fluoro-4-nitropheny)-2-propenamide (Example 8) (1.3 mmol) in acetone-water (10:5) was reacted according to the procedure as described in the Example 6. The title compound, melting point 170-172° C., was thereby obtained in 47% yield.

NMR (DMSO-d6) δ 3.84 (s, 3H), 5.10 (s, 2H), 5.35 (s, 2H), 6.90 (d, 1H vinylic), 7.60 (d, 1H vinylic), 6.70-7.45 (m, aromatic).

EXAMPLE 10

(E)-N-(4-Methoxy-3-trifluoroacetamidophenyl)-3-(2,4,6-trimethoxyphenyl)-2-propenamide A solution of trifluoroacetic anhydride (20 mmol) and (E)-N-(4-methoxy-3-aminophenyl)-3-(2,4,6-trimethoxyphenyl)-2-propenamide (10 mmol) (Example 6) in dry DCM (25 mL) was stirred for 2 hours at ambient temperature. Then, the reaction mixture was concentrated under vacuum and the crude product obtained was purified by washing with diethyl ether to yield the desired product in 43% yield.

EXAMPLE 11

(E)-N-(3-Hydoxy-4-methoxyphenyl)-3-(2,4,6-trimethoxyphenyl)-2-propenamide

A solution of 3-hydroxy-4-methoxyphenylamino-3-oxopropanoic acid and 2,4,6-trimethoxybenzaldehyde was reacted according to General Procedure 1. The title compound, melting point 188-189° C., was thereby obtained in 52% yield.

NMR (DMSO-d6), δ 3.82 (s, 3H), 3.84 (s, 6H), 3.94 (s, 3H), 6.12 (s 2H), 7.18 (d, 1H vinylic), 7.64 (d,1H vinylic), 7.10-7.87 (m, aromatic).

EXAMPLE 12

(E)-N-(4-Bromophenyl)-3-(3-methoxy-4fluorophenyl)-2-propenamide

A solution of 4-bromophenylamino-3-oxopropanoic acid and 3-methoxy-4-fluorobenzaldehyde was reacted according to General Procedure 1. The title compound, melting point 163-165° C., was thereby obtained in 52% yield.

NMR (DMSO-d6), δ 3.80 (s, 3H), 7.0 (d, 1H vinylic), 7.68 (d 1H vinylic), 7.25-7.88 (m, aromatic).

EXAMPLE 13

(E)-N-(4-Bromophenyl)-3-(3-cyano-4-fluorophenyl)-2-propenamide

A solution of 4-bromophenylamino-3-oxopropanoic acid and 3-cyano-4-fluorobenzaldehyde was reacted according to General Procedure 1. The title compound, melting point 205-210° C., was thereby obtained in 57% yield.

NMR (DMSO-d6), 5 7.15 (d, 1H vinylic), 7.72 (d 1H vinylic), 7.25-8.10 (m, aromatic).

EXAMPLE 14

(E)-N-(4-Bromophenyl)-3-(3-carboxy-4-fluorophenyl)-2-propenamide (E)-N-(4-Bromophenyl)-3-(3-cyano-4-fluorophenyl)-2-propenamide(Example 13) (1 gm) was dissolved in acetic acid (10 mL). Aqueous sulfuric acid (50%, 10 mL) was then slowly added to the acetic acid solution. The resulting solution was refluxed for 3 hours, then cooled and poured into cold water. The resulting solid precipitate was collected by filtration and purified by column chromatography over silica to yield 32% of the desired product.

EXAMPLE 15

Effect of Aryl and Heteroaryl Propene Amides on Tumor Cell Lines

The effect of the aromatic acrylamides on normal fibroblasts and on tumor cells was determined by the assay described by Latham et al.,*Oncogene* 12:827-837 (1996). Normal diploid lung human fibroblasts (HFL-1) or tumor cells (BT20(breast cancer), DLD1 (colorectal cancer), DU145 (prostate cancer and K562 (chronic myelogenous leukemia )) were plated in 6-well dishes at a cell density of 1.0×10$^5$cells per 35-mm$^2$ well. The plated cells were treated 24 hours later with a compound of the invention, dissolved in DMSO at multiple concentrations ranging from 100 nM to 10 µM. The total number of viable cells was determined 96 hours later by trypsinizing the wells and counting the number of viable cells, as determined by trypan blue exclusion, using a hemacytometer. Normal HFL cells were treated with the same compounds under the same conditions of concentration and time. The normal cells displayed growth inhibition but no appreciable cell death.

Representative examples of activities of compounds of the invention in cell lines: BT20(breast cancer), DLD1 (colorectal cancer), DU145 (prostate cancer and K562 (chronic myelogenous leukemia ) are listed in Table 5.

TABLE 5

| Example # | Structure | BT20 | DU145 | K562 | DLD1 |
|---|---|---|---|---|---|
| 1 | 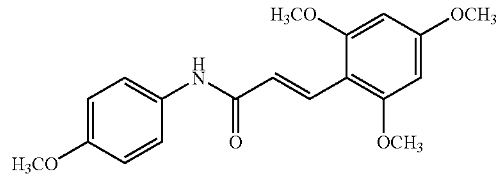 | +++ | +++ | +++ | +++ |
| 2 | 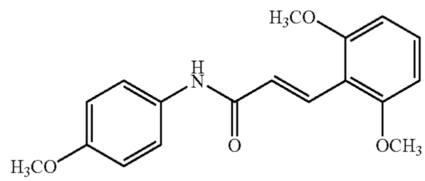 | + | + | + | + |
| 3 | 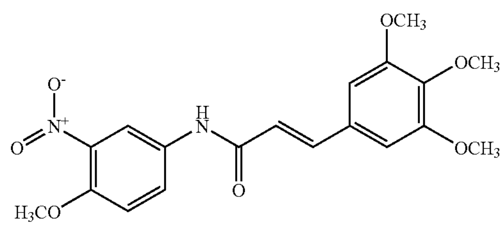 | NT | NT | NT | NT |
| 4 | 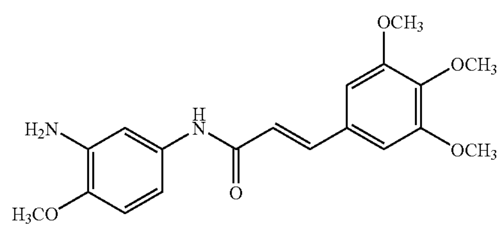 | + | + | + | + |
| 5 | 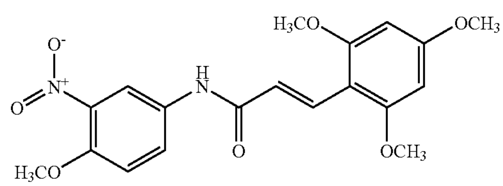 | NT | NT | NT | NT |
| 6 | 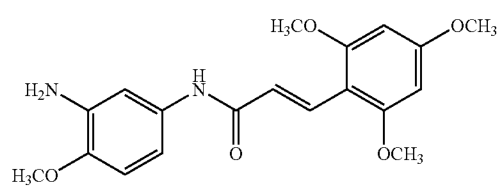 | +++ | +++ | +++ | +++ |
| 7 | 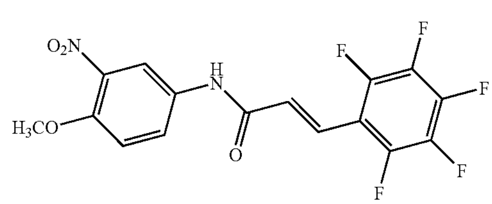 | ++ | ++ | ++ | ++ |

TABLE 5-continued
| Example # | Structure | BT20 | DU145 | K562 | DLD1 |
|---|---|---|---|---|---|
| 8 | 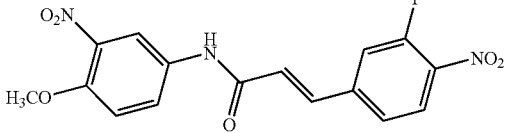 | NT | NT | NT | NT |
| 9 | 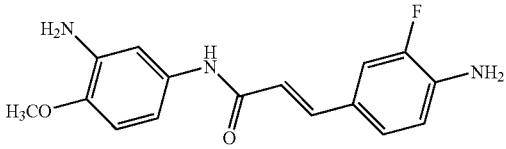 | ++ | ++ | ++ | ++ |
| 10 | 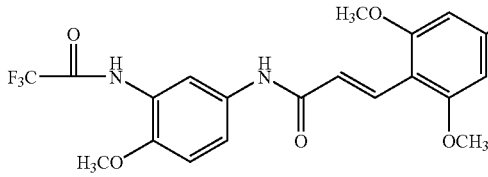 | +++ | +++ | +++ | +++ |
| 11 | 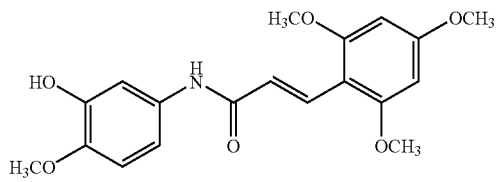 | ++++ | ++++ | ++++ | ++++ |
| 12 | 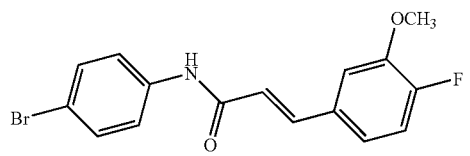 | ++ | ++ | ++ | ++ |
| 13 | 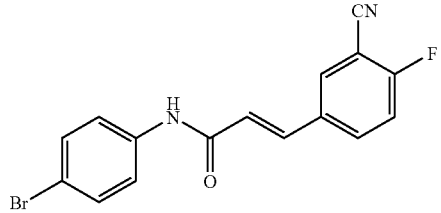 | ++ | ++ | ++ | ++ |
| 14 | 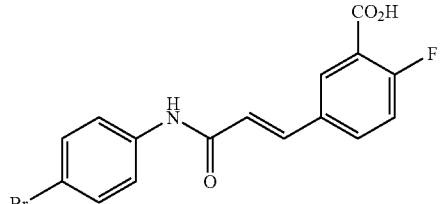 | NT | NT | NT | NT |
+ denotes activity at >10 μM;
++ denotes activity at 10 μM;
+++ denotes activity at 100 nM;
++++ denotes activity at <100 nm;
NT = not tested.

EXAMPLE 16

Induction of Apoptosis in Tumor Cells

The following assay demonstrates the apoptotic activity of the compounds of the invention against tumor cells.

The caspases and the ICE-family proteases are cysteine proteases which are activated during apoptosis (Patel et al., FASEB 10:587-597, 1996). The cleavage of poly(ADP-ribose) polymerase (PARP), which is a target of caspase-3, apopain, and several other activated proteases, is a widely used and accepted marker for apoptosis (Nicholson et al., Nature 376(6533):37-43, 1995; Lippke et al., *J. Biol. Chemistry* 271:1825, 1996).

For this assay, BT20 cells, an estrogen receptor negative breast carcinoma, and HFL-1 cells, normal lung fibroblasts, are treated with a compound according to the present invention at a final concentration of 20 µM in DMSO for 96 hours. The cells are then lysed in RIPA buffer and 100 µg of total cellular protein from each sample is resolved on a 10% SDS-polyacrylamide gel. The proteins are then Western blotted onto PROTRAN filter paper (S/S) and the filter is then probed with antibody (Boehringer Mannheim) specific for PARP. This antibody recognizes both the 116 kDa full length PARP and the 83 kDa cleaved product. The assay will show whether the test compound specifically activates caspases in the treated breast carcinoma cell line and not in the normal cell line. The western blot will show whether only the test compound-treated BT20 cells displayed the presence of the 83 kDa PARP cleavage product. The HFL-1 cells treated in a similar manner as controls, will show no cleavage of the full length PARP. BT20 cells treated with DMSO as a control for the same amount of time will also show no activation of the apoptotic pathway. These results will show that the compounds of the invention selectively kill cancer cells by activating the apoptotic pathway as indicated by the activation of the cysteine proteases, a molecular marker for apoptosis. Cells which are not tumorigenic will not undergo apoptosis but may become growth arrested at concentrations significantly higher than the concentration necessary for tumor cell death.

EXAMPLE 17

Radioprotective Effects of Aryl and Heteroaryl Propene Amides on Cultured Normal Cells The radioprotective effects of compounds of the invention are evaluated on cultured normal cells as follows:

HFL-1 cells, which are normal diploid lung fibroblasts, are plated into 24 well dishes at a cell density of 3000 cells per 10 $mm^2$ in DMEM completed with 10% fetal bovine serum and antibiotics. The test compounds are added to the cells 24 hours later in select concentrations from 2.5 µM and 10.0 µM, inclusive, using DMSO as a solvent. Control cells are treated with DMSO alone. The cells are exposed to the test compound or DMSO for 24 hours.

The cells are then irradiated with 10 Gy of ionizing radiation (IR) using a J. L. Shepherd Mark I, Model 30-1 Irradiator equipped with $^{137}$cesium as a source. After irradiation, the medium on the test and control cells is removed and replaced with fresh growth medium without the test compounds or DMSO. The irradiated cells are incubated for 96 hours and then duplicate wells are trypsinized and replated onto 100 $mm^2$ tissue culture dishes. The replated cells are grown under normal conditions with one change of fresh medium for 2 weeks. The number of colonies from each 100 $mm^2$ culture dish, which represents the number of surviving cells, may be determined by staining the dishes as described below.

In order to visualize and count the colonies derived from the clonal outgrowth of individual protected cells, the medium is removed and the plates are washed one time with room temperature phosphate buffered saline. The cells are stained with a 1:10 diluted Modified Geimsa staining solution (Sigma) for 20 minutes. The stain is removed, and the plates are washed with tap water. The plates are air-dried, the number of colonies from each plate is counted and the average from duplicate plates is determined. Radioprotective activity of x-fold protection is determined by dividing the average number of colonies from the test plates by the average number of colonies counted on the control plates.

EXAMPLE 18

Protection of Mice from Radiation Toxicity by Pre-Treatment with Aryl and Heteroaryl Propene Amides C57 black mice age 10-12 weeks (Taconic) are divided into treatment groups of 10 mice each and given intraperitoneal injections of 200 micrograms of an aryl or heteroaryl propene amide dissolved in DMSO (a 10 mg/Kg dose, based on 20 g mice). The injections are given 18 and 6 hours before irradiation with 8 Gy gamma radiation. A control group of 10 animals receives 8 Gy gamma radiation alone. Mortality of control and experimental groups is assessed for 40 days after irradiation.

EXAMPLE 19

Radioprotective Effect of Aryl and Heteroaryl Propene Amides in Mice when Given After Radiation Exposure C57 B6/J mice age 10-12 weeks (Taconic) are divided into treatment groups and one control group of 10 mice each. Each treatment group receives intraperitoneal injections of 200 micrograms of a radioprotective compound of the invention dissolved in DMSO (a 10 mg/Kg dose, based on 20 g mice) 15 minutes after irradiation with 8 Gy gamma radiation. The control group receives 8 Gy gamma radiation alone. Mortality of control and treatment groups are assessed for 40 days after irradiation.

EXAMPLE 20

Effect of Exposure to Ionizing Radiation on Normal and Malignant Hematopoietic Progenitor Cell Growth After Pretreatment with Aryl and Heteroaryl Propene Amides The effect of ionizing radiation on normal and malignant hematopqietic progenitor cells which are pretreated with aryl and heteroaryl propene amides is investigated by assessing cloning efficiency and development of the pretreated cells after irradiation.

To obtain hematopoietic progenitor cells, human bone marrow cells (BMC) or peripheral blood cells (PB) are obtained from normal healthy, or acute or chronic myelogenous leukemia (AML, CML), volunteers by Ficoll-Hypaque density gradient centrifugation, and are partially enriched for hematopoietic progenitor cells by positively selecting CD34$^+$ cells with immunomagnetic beads (Dynal A. S., Oslo, Norway). The CD34$^+$ cells are suspended in supplemented alpha medium and incubated with mouse anti-HPCA-I antibody in 1:20 dilution, 45 minutes, at 4° C. with gentle inverting of tubes. Cells are washed 3× in supplemented alpha medium, and then incubated with beads coated with the Fc fragment of goat anti-mouse IgG1 (75 μL of immunobeads/$10^7$ CD34$^+$ cells). After 45 minutes of incubation (4° C.), cells adherent to the beads are positively selected using a magnetic particle concentrator as directed by the manufacturer.

$2 \times 10^4$ CD34$^+$ cells are incubated in 5 mL polypropylene tubes (Fisher Scientific, Pittsburgh, Pa.) in a total volume of 0.4 mL of Iscove's modified Dulbecco's medium (IMDM) containing 2% human AB serum and 10 mM Hepes buffer. A compound of the invention, for example (E)-N-(4-methoxyphenyl)-3-(2,4,6-trimethoxyphenyl)-2-propenamide or (E)-N-(4-methoxy-3-aminophenyl)-3-(2,4,6-triiethoxyphenyl)-2-propenamide, at three different concentrations (2.5 μM, 5.0 μM and 10.0 μM) in DMSO is added separately to the cells. Control cells receive DMSO alone. The cells are incubated for 20-24 hours and irradiated with 5 Gy or 10 Gy of ionizing radiation. Immediately after irradiation, the medium is removed and replaced with fresh medium without the test compound or DMSO. Twenty-four hours after irradiation, the treatment and control cells are prepared for plating in plasma clot or methylcellulose cultures. Cells ($1 \times 10^4$ CD34$^+$ cells per dish) are not washed before plating.

Assessment of the cloning efficiency and development of the treated hematopoietic progenitor cells are carried out essentially as reported in Gewirtz et al., *Science* 242, 1303-1306 (1988), the entire disclosure of which is incorporated herein by reference.

EXAMPLE 21

Bone Marrow Purging with Ionizing Radiation After Pretreatment with an Aryl or Heteroaryl Propene Amide Bone marrow is harvested from the iliac bones of a subject under general anesthesia in an operating room using standard techniques. Multiple aspirations are taken into heparinized syringes. Sufficient marrow is withdrawn so that the subject will be able to receive about $4 \times 10^8$ to about $8 \times 10^8$ processed marrow cells per kg of body weight. Thus, about 750 to 1000 mL of marrow is withdrawn. The aspirated marrow is transferred immediately into a transport medium (TC-199, Gibco, Grand Island, N.Y.) containing 10,000 units of preservative-free heparin per 100 mL of medium. The aspirated marrow is filtered through three progressively finer meshes to obtain a cell suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure is carried out as follows. Cells in the buffy coat preparation are adjusted to a cell concentration of about $2 \times 10^7$/mL in TC-199 containing about 20% autologous plasma. A compound of the invention; for example 2.5 to 10 micromolar of either (E)-N-(4-methoxyphenyl)-3-(2,4,6-trimethoxyphenyl)-2-propen-amide or (E)-N-(4-methoxy-3-aminophenyl)-3-(2,4,6-trimethoxyphenyl)-2-propenamide in DMSO is added to the transfer packs containing the cell suspension and incubated in a 37° C. water bath for 20-24 hours with gentle shaking. The transfer packs are then exposed to 5-10 Gy ionizing radiation. Recombinant human hematopoietic growth factors, e.g., rH IL-3 or rH GM-CSF, may be added to the suspension to stimulate growth of hematopoietic neoplasms and thereby increase their sensitivity to ionizing radiation.

The cells may then either be frozen in liquid nitrogen or washed once at 4° C. in TC-199 containing about 20% autqlogous plasma. Washed cells are then infused into the subject. Care must be taken to work under sterile conditions wherever possible and to maintain scrupulous aseptic techniques at all times.

EXAMPLE 22

Protection of Normal Human Fibroblasts from Paclitaxel Cytotoxicity by Aryl and Heteroaryl Propene Amides HFL-1 cells are plated at a cell density of $1.0 \times 10^5$ per well 24 hours prior to drug addition. Cells are pretreated with a cytoprotective compound of formula I (2.0 μM) for 8 hours and then exposed to paclitaxel (250 μM). Other cells are treated with paclitaxel alone, or both agents simultaneously. Cells are enumerated by Trypan blue exclusion using a hematocytometer 96 hours after exposure to paclitaxel. Cytoprotective activity may be compared by comparing the number of viable cells following treatment with a cytoprotective compound of the invention and paclitaxel, divided by the number of viable cells remaining after treatment with paclitaxel alone.

EXAMPLE 23

Protection of Normal Human Fibroblasts from Anticancer Agent Cytotoxicity

HFL-1 cells are plated at a cell density of $1.0 \times 10^5$ in 1 mL of medium. Twenty-four hours following plating, 2.0 μM of a cytoprotective compound of the invention was added to the medium. Following a 24-hour preincubation with the cytoprotective compound, the various cytotoxic agents (selected from the list below) are added to the cells.

The number of viable cells is determined by Trypan blue exclusion using a hematocytometer 96 hours after exposure to cytotoxic agent. The "Protection Ratio" is the number of viable cells following treatment with a cytoprotective compound of the invention and cytotoxic agent, divided by the number of viable cells remaining after treatment with cytotoxic agent alone. A protection ratio of 2 or more is considered highly significant, while a protection ratio of 1.5-2 is considered less significant.

| Drug | Therapeutic concentration (μM) | Mechanism of Action |
|---|---|---|
| paclitaxel | 0.25 | antimitotic |
| vincristine | 0.25 | antimitotic |
| camptothecin | 0.5 | topoisomerase I inhibitor |
| etoposide | 3.0 | topoisomerase II inhibitor |
| mitoxantrone | 0.3 | topoisomerase II inhibitor |
| doxorubicin | 0.4 | topoisomerase II inhibitor |
| 5-fluorouracil | 20 | DNA antimetabolite |
| cisplatin | 5.0 | alkylating agent |

EXAMPLE 24

Protection of Normal Human Fibroblasts from Vincristine Cytotoxicity by Aryl Propene Amides HFL-1 cells are treated with 0-250 µM vincristine and, optionally, a 2.0 µM preparation of a compound of the invention, either 24 hours before or after vincristine treatment, or simultaneously with vincristine treatment. Cell viability is assessed 96 hours after the addition of vincristine.

EXAMPLE 25

Protection of Mice From Paclitaxel Toxicity Using Aryl and Heteroaryl Propene Amides ICR female mice age 10-12 weeks (Taconic) are divided into the following treatment groups and receive intraperitoneal injections of 50 mg/Kg a compound of the invention, dissolved in DMSO and/or 150 mg/kg paclitaxel (Taxol, Sigma Chemical Co.) dissolved in DMSO. The compound of formula I is given 24 hours before paclitaxel, 4 hours before paclitaxel, or simultaneously with paclitaxel. Control animals receive paclitaxel alone or a compound of the invention alone. Mortality is assessed 48 and 144 hours after paclitaxel injection.

EXAMPLE 26

Antitumor and Cytoprotection Assay of Aryl and Heteroaryl Propene Amides

A. Antitumor Assay

The aryl and heteroaryl propene amides may be tested for antitumor activity as follows:

A panel of the following human carcinoma cell lines is plated at a cell density of $1.0 \times 10^5$ cells per well in six culture plates: prostate tumor cell line DU-145; breast tumor cell line BT20; chronic myelogenous leukemia cell line K562; and colorectal carcinoma cell line DLD-1. The compounds are added to the cultures at a final concentration of 2.5 µM, and 96 hours later the total number of viable cells is determined by counting the number of viable cells, as determined by Trypan blue exclusion, using a hematocytometer. The activity of each compound is determined by comparing the viable cell number of treated to untreated controls.

B. Cytoprotection Assay

The cytoprotective activity of the compounds may be determined as follows:

Normal human HFL-1 cells are plated at a cell density of $1.0 \times 10^5$ cells per well in culture plates. A cytoprotective compound of the invention is added 24 hours later at a final concentration of 2.0-10 µM. The time of addition of the cytoprotective compound is designated as time zero. Paclitaxel (250 nM) is added at either time zero, or 24 hours after time zero. The total number of viable cells is determined, as described above, after 96 hours of paclitaxel treatment. A cytoprotective compound is deemed to be active if the number of viable cells following the combination treatment is higher than the number of cells after treatment with paclitaxel alone.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound selected from the group consisting of: (E)-N-(4-methoxy-3-nitrophenyl)-3-(3,4,5-trimethoxyphenyl)-2-propenamide;
   (E)-N-(4-methoxy-3-aminophenyl)-3-(3,4,5-trimethoxyphenyl)-2-propenamide;
   (E)-N-(4-methoxy-3-nitrophenyl)-3-(2,3,4,5,6-pentafluorophenyl)-2-propenamide;
   (E)-N-(4-methoxy-3-nitrophenyl)-3-(3-fluoro-4-nitrophenyl)-2-propenamide;
   (E)-N-(4-methoxy-3-aminophenyl)-3-(3-fluoro-4-aminophenyl)-2-propenamide;
   (E)-N-(4-methoxy-3-nitrophenyl)-3-(2,4,6-trimethoxyphenyl)-2-propenamide;
   (E)-N-(4-methoxy-3-aminophenyl)-3-(2,4,6-trimethoxyphenyl)-2-propenamide;
   (2E)-N-[4-methoxy-3-(2,2,2-trifluoroacetylamino)phenyl]-3-(2,4,6-trimethoxyphenyl)prop-2-enamide; and salts of such compounds.

2. The compound (E)-N-(3-hydroxy-4-methoxyphenyl)-3-(2,4,6-trimethoxyphenyl)-2-propenamide, or a salt thereof.

3. A compound selected from the group consisting of: 2-({5-[(2E)-3-(2,4,6-trimethoxyphenyl)prop-2-enoylamino]-2-methoxyphenyl}amino)acetic acid; 2-({5-[(2E)-3-(2,4,6-trimethoxyphenyl)prop-2-enoylamino]-2-methoxyphenyl}amino)propanoic acid; 4-({5-[(2E)-3-(2,4,6-trimethoxyphenyl)prop-2-enoylamino]-2-methoxyphenyl}amino)butanoic acid; 3-({5-[(2E)-3-(2,4,6-trimethoxyphenyl)prop-2-enoylamino]-2-methoxyphenyl}amino)propanoic acid; and salts of such compounds.

4. A pharmaceutical composition comprising a pharmaceutically acceptable carrier and at least one compound according to claim 1, 2, or 3.

5. A method of treating an individual for a cancer selected from breast cancer, prostate cancer, lung cancer and colorectal cancer comprising administering to said individual an effective amount of at least one compound selected from the group consisting of: (E)-N-(4-methoxy-3-aminophenyl)-3-(3,4,5-trimethoxyphenyl)-2-propenamide;
   (E)-N-(4-methoxy-3-nitrophenyl)-3-(2,3,4,5,6-pentafluorophenyl)-2-propenamide;
   (E)-N-(4-bromophenyl)-3-(3-methoxy-4-fluorophenyl)-2-propenamide;
   (E)-N-(4-bromophenyl)-3-(3-cyano-4-fluorophenyl)-2-propenamide;
   (E)-N-(4-methoxy-3-aminophenyl)-3-(3-fluoro-4-aminophenyl)-2-propenamide;
   (E)-N-(4-methoxyphenyl)-3-(2,4,6-trimethoxyphenyl)-2-propenamide;
   (E)-N-(4-methoxyphenyl)-3-(2,6-dimethoxyphenyl)-2-propenamide;
   (E)-N-(3-hydroxy-4-methoxyphenyl)-3-(2,4,6-trimethoxyphenyl)-2-propenamide;
   (E)-N-(4-methoxy-3-aminophenyl)-3-(2,4,6-trimethoxyphenyl)-2-propenamide;
   (2E)-N-[4-methoxy-3-(2,2,2-trifluoroacetylamino)phenyl]-3-(2,4,6-trimethoxyphenyl)prop-2-enamide; and salts thereof.

6. A method of selectively inducing apoptosis of tumor cells selected from the group of tumors consisting of breast, prostate, lung, and colorectal tumors in an individual afflicted with cancer comprising administering to said individual an effective amount of at least one compound selected from the group consisting of: (E)-N-(4-methoxy-3-aminophenyl)-3-(3,4,5-trimethoxyphenyl)-2-propenamide;

(E)-N-(4-methoxy-3-nitrophenyl)-3-(2,3,4,5,6-pentafluorophenyl)-2-propenamide;
(E)-N-(4-bromophenyl)-3-(3-methoxy-4-fluorophenyl)-2-propenamide;
(E)-N-(4-bromophenyl)-3-(3-cyano-4-fluorophenyl)-2-propenamide;
(E)-N-(4-methoxy-3-aminophenyl)-3-(3-fluoro-4-aminophenyl)-2-propenamide;
(E)-N-(4-methoxyphenyl)-3-(2,4,6-trimethoxyphenyl)-2-propenamide;
(E)-N-(4-methoxyphenyl)-3-(2,6-dimethoxyphenyl)-2-propenamide;
(E)-N-(3-hydroxy-4-methoxyphenyl)-3-(2,4,6-trimethoxyphenyl)-2-propenamide;
(E)-N-(4-methoxy-3-aminophenyl)-3-(2,4,6-trimethoxyphenyl)-2-propenamide;
(2E)-N-[4-methoxy-3-(2,2,2-trifluoroacetylamino)phenyl]-3-(2,4,6-trimethoxyphenyl)prop-2-enamide; and salts thereof.

* * * * *